(12) United States Patent
Chuang et al.

(10) Patent No.: US 10,462,391 B2
(45) Date of Patent: Oct. 29, 2019

(54) DARK-FIELD INSPECTION USING A LOW-NOISE SENSOR

(71) Applicant: KLA-Tencor Corporation, Milpitas, CA (US)

(72) Inventors: Yung-Ho Alex Chuang, Cupertino, CA (US); David L. Brown, Los Gatos, CA (US); Devis Contarato, San Carlos, CA (US); John Fielden, Los Altos, CA (US); Daniel I. Kavaldjiev, San Jose, CA (US); Guoheng Zhao, Palo Alto, CA (US); Jehn-Huar Chern, Morgan Hill, CA (US); Guowu Zheng, San Jose, CA (US); Donald W. Pettibone, San Jose, CA (US); Stephen Biellak, Sunnyale, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 110 days.

(21) Appl. No.: 15/210,056

(22) Filed: Jul. 14, 2016

(65) Prior Publication Data

US 2017/0048467 A1 Feb. 16, 2017

Related U.S. Application Data

(60) Provisional application No. 62/205,309, filed on Aug. 14, 2015.

(51) Int. Cl.
*H04N 5/335* (2011.01)
*G01N 21/95* (2006.01)
(Continued)

(52) U.S. Cl.
CPC ............ *H04N 5/335* (2013.01); *H04N 5/2256* (2013.01); *H04N 5/347* (2013.01);
(Continued)

(58) Field of Classification Search
CPC ...... H04N 5/378; H04N 5/3745; H04N 5/335; H04N 5/347; H04N 5/3765; H04N 5/351;
(Continued)

(56) References Cited

U.S. PATENT DOCUMENTS 3,870,917 A 3/1975 Cuny
3,947,707 A 3/1976 Shannon et al.
(Continued)

FOREIGN PATENT DOCUMENTS

EP 0602983 A1 6/1994
EP 0746871 A1 12/1996
(Continued)

OTHER PUBLICATIONS

U.S. Appl. No. 61/720,700—Certified Copy corres to PCT/EP2013/071080, pp. 1-44.
(Continued)

*Primary Examiner* — Taeho Jo
(74) *Attorney, Agent, or Firm* — Bever, Hoffman & Harris, LLP

(57) ABSTRACT

An inspection system and methods in which analog image data values (charges) captured by an image sensor are binned (combined) before or while being transmitted as output signals on the image sensor's output sensing nodes (floating diffusions), and in which an ADC is controlled to sequentially generate multiple corresponding digital image data values between each reset of the output sensing nodes. According to an output binning method, the image sensor is driven to sequentially transfer multiple charges onto the output sensing nodes between each reset, and the ADC is controlled to convert the incrementally increasing output signal after each charge is transferred onto the output sensing node. According to a multi-sampling method, multiple charges are vertically or horizontally binned (summed/
(Continued)

combined) before being transferred onto the output sensing node, and the ADC samples each corresponding output signal multiple times. The output binning and multi-sampling methods may be combined.

21 Claims, 21 Drawing Sheets

(51) Int. Cl.
| | |
|---|---|
| *G06T 7/00* | (2017.01) |
| *H04N 5/225* | (2006.01) |
| *H04N 5/347* | (2011.01) |
| *H04N 5/378* | (2011.01) |
| *H04N 5/3745* | (2011.01) |
| *H04N 5/376* | (2011.01) |
| *G01N 21/956* | (2006.01) |

(52) U.S. Cl.
CPC .............. *G01N 21/9501* (2013.01); *G01N 2021/95676* (2013.01); *H04N 5/378* (2013.01); *H04N 5/3745* (2013.01); *H04N 5/3765* (2013.01)

(58) Field of Classification Search
CPC ....... H04N 5/2256; G01N 2021/95676; G01N 21/9501; G01N 21/8851; G01N 21/956
USPC ........................................................ 250/365
See application file for complete search history.

(56) References Cited

U.S. PATENT DOCUMENTS

| | | | |
|---|---|---|---|
| 4,099,198 A | 7/1978 | Howorth et al. | |
| 4,210,922 A | 7/1980 | Shannon | |
| 4,275,326 A | 6/1981 | Houtkamp | |
| 4,348,690 A | 9/1982 | Jastrzebski et al. | |
| 4,467,189 A | 8/1984 | Tsuchiya | |
| 4,555,731 A | 11/1985 | Zinchuk | |
| 4,760,031 A | 7/1988 | Janesick | |
| 5,054,683 A | 10/1991 | Haisma et al. | |
| 5,120,949 A | 6/1992 | Tomasetti | |
| 5,144,630 A | 9/1992 | Lin | |
| 5,227,313 A | 7/1993 | Gluck et al. | |
| 5,315,126 A | 5/1994 | Field | |
| 5,376,810 A | 12/1994 | Hoenk et al. | |
| 5,428,392 A | 6/1995 | Castro et al. | |
| 5,563,702 A | 10/1996 | Emery et al. | |
| 5,717,518 A | 2/1998 | Shafer et al. | |
| 5,719,069 A | 2/1998 | Sparks | |
| 5,731,584 A | 3/1998 | Beyne et al. | |
| 5,742,626 A | 4/1998 | Mead et al. | |
| 5,760,899 A | 6/1998 | Eismann | |
| 5,852,322 A | 12/1998 | Speckbacher | |
| 5,940,685 A | 8/1999 | Loomis et al. | |
| 5,999,310 A | 12/1999 | Shafer et al. | |
| 6,013,399 A | 1/2000 | Nguyen | |
| 6,162,707 A | 12/2000 | Dinh et al. | |
| 6,201,601 B1 | 3/2001 | Vaez-Iravani et al. | |
| 6,271,916 B1 | 8/2001 | Marxer et al. | |
| 6,278,119 B1 | 8/2001 | Nikzad et al. | |
| 6,285,018 B1 | 9/2001 | Aebi et al. | |
| 6,297,879 B1 | 10/2001 | Yang et al. | |
| 6,307,586 B1 | 10/2001 | Costello | |
| 6,346,700 B1 | 2/2002 | Cunningham et al. | |
| 6,362,484 B1 | 3/2002 | Beyne et al. | |
| 6,373,869 B1 | 4/2002 | Jacob | |
| 6,403,963 B1 | 6/2002 | Nikzad et al. | |
| 6,535,531 B1 | 3/2003 | Smith et al. | |
| 6,545,281 B1 | 4/2003 | McGregor et al. | |
| 6,608,676 B1 | 8/2003 | Zhao et al. | |
| 6,711,283 B1 | 3/2004 | Soenksen | |
| 6,837,766 B2 | 1/2005 | Costello | |
| 7,005,637 B2 | 2/2006 | Costello et al. | |
| 7,039,157 B2 | 5/2006 | Fujii et al. | |
| 7,126,699 B1 | 10/2006 | Wihl et al. | |
| 7,130,039 B2 | 10/2006 | Vaez-Iravani et al. | |
| 7,136,159 B2 | 11/2006 | Tsai et al. | |
| 7,141,791 B2 | 11/2006 | Masnaghetti et al. | |
| 7,283,166 B1 | 10/2007 | Billman | |
| 7,321,468 B2 | 1/2008 | Herkommer et al. | |
| 7,345,825 B2 | 3/2008 | Chuang et al. | |
| 7,352,457 B2 | 4/2008 | Kvamme et al. | |
| 7,432,517 B2 | 10/2008 | Botma et al. | |
| 7,446,474 B2 | 11/2008 | Maldonado et al. | |
| 7,465,935 B2 | 12/2008 | Urano et al. | |
| 7,525,649 B1 | 4/2009 | Leong et al. | |
| 7,528,943 B2 | 5/2009 | Brown et al. | |
| 7,586,108 B2 | 9/2009 | Nihtianov et al. | |
| 7,609,309 B2 | 10/2009 | Brown et al. | |
| 7,714,287 B1 | 5/2010 | James et al. | |
| 7,741,666 B2 | 6/2010 | Nozaki et al. | |
| 7,750,280 B2 | 7/2010 | Hwang et al. | |
| 7,791,170 B2 | 9/2010 | Chiang et al. | |
| 7,800,040 B2 | 9/2010 | Blacksberg et al. | |
| 7,813,406 B1 | 10/2010 | Nguyen et al. | |
| 7,838,833 B1 | 11/2010 | Lent et al. | |
| 7,875,948 B2 | 1/2011 | Hynecek et al. | |
| 7,928,382 B2 | 4/2011 | Hatakeyama et al. | |
| 7,952,633 B2 | 5/2011 | Brown et al. | |
| 7,985,658 B2 | 7/2011 | Lei et al. | |
| 8,017,427 B2 | 9/2011 | Manabe | |
| 8,138,485 B2 | 3/2012 | Nihtianov et al. | |
| 8,309,443 B2 | 11/2012 | Tanaka et al. | |
| 8,450,820 B2 | 5/2013 | Nanver et al. | |
| 8,455,971 B2 | 6/2013 | Chen et al. | |
| 8,513,587 B2 | 8/2013 | Wang et al. | |
| 8,629,384 B1 | 1/2014 | Biellak et al. | |
| 8,754,972 B2 | 6/2014 | Brown et al. | |
| 8,755,417 B1 | 6/2014 | Dribinski | |
| 8,873,596 B2 | 10/2014 | Dribinski et al. | |
| 8,891,079 B2 | 11/2014 | Zhao et al. | |
| 8,929,406 B2 | 1/2015 | Chuang et al. | |
| 9,055,246 B2 | 6/2015 | Tay | |
| 9,077,862 B2 | 7/2015 | Brown et al. | |
| 9,131,175 B2 * | 9/2015 | Kondou .............. H04N 5/3696 |
| 9,282,271 B2 | 3/2016 | Hashimoto et al. | |
| 9,601,299 B2 | 3/2017 | Chuang et al. | |
| 2001/0017344 A1 | 8/2001 | Aebi | |
| 2003/0222579 A1 | 12/2003 | Habib et al. | |
| 2004/0021061 A1 | 2/2004 | Bijkerk | |
| 2004/0056279 A1 | 3/2004 | Niigaki et al. | |
| 2004/0227070 A1 | 11/2004 | Bateman et al. | |
| 2005/0167575 A1 | 8/2005 | Benz et al. | |
| 2005/0196059 A1 | 9/2005 | Inoue et al. | |
| 2005/0224842 A1 | 10/2005 | Toyama et al. | |
| 2005/0264148 A1 | 12/2005 | Maldonado et al. | |
| 2006/0054778 A1 | 3/2006 | Suhling | |
| 2006/0055321 A1 | 3/2006 | Maldonado et al. | |
| 2006/0069460 A1 | 3/2006 | Smith et al. | |
| 2006/0170324 A1 | 8/2006 | MacHuca et al. | |
| 2006/0188869 A1 | 8/2006 | Zeskind et al. | |
| 2007/0002465 A1 | 1/2007 | Chuang et al. | |
| 2007/0034987 A1 | 2/2007 | Costello et al. | |
| 2007/0064135 A1 | 3/2007 | Brown et al. | |
| 2007/0103769 A1 | 5/2007 | Kuwabara | |
| 2007/0291810 A1 | 12/2007 | Luo et al. | |
| 2008/0044932 A1 | 2/2008 | Samoilov et al. | |
| 2008/0173903 A1 | 7/2008 | Imai et al. | |
| 2008/0315092 A1 | 12/2008 | Kley | |
| 2008/0315121 A1 | 12/2008 | Nihtianov et al. | |
| 2009/0021717 A1 | 1/2009 | Nihtianov et al. | |
| 2009/0091752 A1 | 4/2009 | Terasawa et al. | |
| 2009/0125242 A1 | 5/2009 | Choi et al. | |
| 2009/0128912 A1 | 5/2009 | Okada et al. | |
| 2009/0168152 A1 | 7/2009 | Gelernt et al. | |
| 2009/0180176 A1 | 7/2009 | Armstrong et al. | |
| 2009/0190015 A1 * | 7/2009 | Bechtel .............. H04N 5/2355 348/302 |
| 2009/0322903 A1 | 12/2009 | Hashimoto et al. | |
| 2010/0102213 A1 | 4/2010 | Garris | |
| 2010/0148667 A1 | 6/2010 | Niigaki et al. | |
| 2010/0188655 A1 | 7/2010 | Brown et al. | |

(56) References Cited

U.S. PATENT DOCUMENTS

| | | |
|---|---|---|
| 2010/0194956 A1 | 8/2010 | Yuan et al. |
| 2010/0208979 A1 | 8/2010 | Abbott et al. |
| 2010/0301437 A1 | 12/2010 | Brown et al. |
| 2011/0073982 A1 | 3/2011 | Armstrong et al. |
| 2011/0101219 A1 | 5/2011 | Uchiyama et al. |
| 2011/0116077 A1 | 5/2011 | Chuang et al. |
| 2011/0168886 A1 | 7/2011 | Shadman et al. |
| 2011/0169116 A1 | 7/2011 | Nanver et al. |
| 2011/0234790 A1 | 9/2011 | True |
| 2011/0256655 A1 | 10/2011 | Nikzad et al. |
| 2011/0261354 A1 | 10/2011 | Sinfield et al. |
| 2011/0291109 A1 | 12/2011 | Wraback et al. |
| 2012/0012811 A1 | 1/2012 | Deflumere et al. |
| 2012/0012957 A1 | 1/2012 | Larsen et al. |
| 2012/0038809 A1 | 2/2012 | Lee et al. |
| 2012/0081684 A1 | 4/2012 | Den Oef et al. |
| 2012/0132823 A1 | 5/2012 | Menge et al. |
| 2012/0160993 A1 | 6/2012 | Nevet et al. |
| 2012/0170021 A1 | 7/2012 | Walsh |
| 2012/0228485 A1 | 9/2012 | Iwakiri et al. |
| 2012/0268722 A1 | 10/2012 | Nihtianov et al. |
| 2013/0009042 A1* | 1/2013 | Bechtel .......... H04N 3/155 250/208.1 |
| 2013/0015324 A1 | 1/2013 | Park et al. |
| 2013/0016346 A1 | 1/2013 | Romanovsky et al. |
| 2013/0017205 A1 | 1/2013 | Giaccia et al. |
| 2013/0056843 A1 | 3/2013 | Lee et al. |
| 2013/0077086 A1 | 3/2013 | Chuang et al. |
| 2013/0082241 A1 | 4/2013 | Kub et al. |
| 2013/0088706 A1 | 4/2013 | Chuang et al. |
| 2013/0148112 A1 | 6/2013 | Chuang et al. |
| 2013/0176552 A1 | 7/2013 | Brown et al. |
| 2013/0264481 A1 | 10/2013 | Chern et al. |
| 2013/0270663 A1 | 10/2013 | Lin et al. |
| 2013/0313440 A1 | 11/2013 | Chuang et al. |
| 2013/0320211 A1 | 12/2013 | Park et al. |
| 2013/0341504 A1 | 12/2013 | Neill et al. |
| 2014/0151552 A1 | 6/2014 | Jiang et al. |
| 2014/0158864 A1 | 6/2014 | Brown et al. |
| 2014/0203386 A1 | 7/2014 | Bui et al. |
| 2014/0204427 A1 | 7/2014 | Nakazawa et al. |
| 2014/0226140 A1 | 8/2014 | Chuang et al. |
| 2014/0246595 A1 | 9/2014 | Menge et al. |
| 2014/0291493 A1 | 10/2014 | Chuang et al. |
| 2014/0305367 A1 | 10/2014 | Chuang et al. |
| 2014/0362203 A1 | 12/2014 | Delaney et al. |
| 2015/0007765 A1 | 1/2015 | Dribinski |
| 2015/0022699 A1* | 1/2015 | Shimada .......... H04N 5/3696 348/273 |
| 2015/0136956 A1* | 5/2015 | Yin .......... H01L 27/14609 250/208.1 |
| 2015/0177159 A1* | 6/2015 | Brown .......... G01N 21/8851 250/208.1 |
| 2015/0237282 A1* | 8/2015 | Shimada .......... H04N 5/23258 348/297 |
| 2015/0256778 A1* | 9/2015 | Kusaka .......... G03B 13/36 348/302 |
| 2015/0294998 A1 | 10/2015 | Nihtianov et al. |
| 2015/0304580 A1* | 10/2015 | Wang .......... H04N 5/378 348/302 |
| 2015/0358571 A1* | 12/2015 | Dominguez Castro .......... H04N 5/345 348/308 |
| 2015/0365610 A1* | 12/2015 | Dominguez Castro .......... H04N 5/345 348/308 |
| 2016/0037110 A1 | 2/2016 | Choi et al. |
| 2016/0050383 A1 | 2/2016 | Grauer et al. |
| 2016/0056606 A1 | 2/2016 | Chuang et al. |
| 2016/0097727 A1 | 4/2016 | Vazhaeparambil et al. |
| 2016/0142653 A1* | 5/2016 | Cho .......... H04N 5/353 348/296 |
| 2016/0269657 A1* | 9/2016 | Nishihara .......... G01J 1/44 |
| 2017/0195596 A1* | 7/2017 | Vogelsang .......... H04N 5/347 |
| 2017/0201698 A1 | 7/2017 | Parks et al. |

FOREIGN PATENT DOCUMENTS

| | | |
|---|---|---|
| EP | 1939917 A2 | 7/2008 |
| EP | 2346094 A1 | 7/2011 |
| JP | H08241977 A | 9/1996 |
| JP | H10171965 A | 6/1998 |
| JP | 2002033473 | 1/2002 |
| JP | 2004031452 A | 1/2004 |
| JP | 2007086108 A | 4/2007 |
| JP | 2009117454 A | 5/2009 |
| KR | 100688497 B1 | 3/2007 |
| KR | 100826407 B1 | 5/2008 |
| RU | 2297070 C2 | 4/2007 |
| WO | 9532518 A1 | 11/1995 |
| WO | 9617372 A1 | 6/1996 |
| WO | 2007035858 A2 | 3/2007 |
| WO | 2008121232 A1 | 10/2008 |
| WO | 2011091159 A1 | 7/2011 |
| WO | 2014067754 A2 | 5/2014 |

OTHER PUBLICATIONS

Allen et al., Work Function, Photoelectric Threshold, and Surface . . . ; Physical Review, vol. 127, No. 1, Jul. 1, 1962, pp. 150-158.

Armstrong, Carter M.The Quest for the Ultimate Vacuum Tube, Spectrum IEEE, Dec. 2015, 4 pgs.

Ding, MengField Emission from Silicon, MIT 2001, 277 pgs.

Fowler, R. H., et al, Electron Emission in Intense Electric Fields, Mar. 31, 1928, 9 pgs.

Fu et al., Optimizing GaN photocathode structure for higher . . . ; Optik, vol. 123, No. 9, May 2012, pp. 756-768.

Hecht, Optics, Fourth Edition, India: Pearson Education Pte, Ltd. 2004.

Hecht, Optics, Second Edition, Adelphi University, 1987, Addison-Wesley Publishing Company, Inc., 3 pages.

Henderson, Brian S., Study of Negative Electron Affinity . . . , Dept. of Physics, Rice Univ., Aug. 7, 2009, 18 pgs.

Howorth et al., Transmission silicon photoemitters . . . , Jrnl of Physics D: Applied Physics, vol. 9, No. 5, Apr. 1, 1976, pp. 785-794.

ISR and Written Opinion dated Mar. 31, 2014 for PCT/US2013/074124.

Janesick, James R., Scientific Charge-Coupled Devices, SPIE Press, 2001, pp. 556-561.

KLA-Tencor Coporation, filed U.S. Appl. No. 62/059,368, filed Oct. 3, 2014 and entitled "183nm Laser and Inspection System".

Koike, AkifumiField Emitter Equipped With a Suppressor to Control Emission Angel, IEEE Electron Device Letters, vol. 34, No. 5, May 2013, 3 pgs.

Martinelli, Ramon U., Infrared Photoemission from Silicon, Applied Physics Letters, vol. 16, No. 7, Apr. 1, 1970, pp. 261-262.

Martinelli, Ramon U., Reflection and Transmission Secondary Emission . . . , Applied Physics Letters, vol. 17, No. 8, Oct. 15, 1970, pp. 313-314.

Nagao, Masayoshi, Cathode Technologies for Field Emission Displays, IEEJ Trans 2006; 1:171-178, 8 pgs.

Nagao, MasayoshiFabrication of a Field Emitter Array with a Built-In Einzel Lens, JJAP 48 (2008) 06FK02, 4 pgs.

Nanver et al., Pure-Boron Chemical-Vapor-Deposited Layers: a New Material for Silicon Device Processing, 18th IEEE International Conference on Advanced Thermal Processing of Semiconductors (RTP), Sep. 28, 2010-Oct. 1, 2010, pp. 136-139.

Nanver, Silicon Photodiodes for Low Penetration Depth Beams such as DUV/VU/EUV Light and Low-Energy Electrons, Advances in Photodiodes, G. Betta, ed., Mar. 22, 2011, pp. 205-224, www.intechopen.com.

Neo, YoichiroElectron Optical Properties of Microcolumn with Field Emitter, JJAP 52 (2013) 036603, 5 pgs.

Rakhshandehroo, M.R. et al, Fabrication of a self-aligned silicon field emission . . . , JVSTB, 16, 765 (1998); doi: 10.1116/1,589900, 6 pgs.

(56) References Cited

OTHER PUBLICATIONS

Rakhshandehroo, M.R. et al, Field emission from gated Si emitter tips with precise . . . , JVSTB, 15, 2777 (1997); doi: 10.1116/1.589726, 6 pgs.
Raoult, Efficient generation of narrow-bandwidth . . . , Jul. 15, 1998, vol. 23, No. 14, Optics Letters, pp. 1117-1119.
Sarubbi et al., Chemical Vapor Deposition of α-Boron Layers on Silicon for Controlled Nanometer-Deep p+n Junction Formation, J. Electron. Mat., vol. 39, No. 2, Feb. 2010, pp. 162-173.
Sarubbi et al., Pure boron-doped photodiodes . . . IEEE, Sep. 15, 2008, pp. 278-281.
Sato, T., et al, Fabrication and characterization of HfC coated . . . , J. Vac. Sci. Technol. B 2194), published Jul. 31, 2003, 5 pgs.
Serbun Pavel et al, Stable field emission of single B-doped . . . , JVSTB, 31, 02B101 (2013); doi: 10.1116/1.4765088, 7 pgs.
Sobieski, Stanley, Intensified Charge Coupled Devices for Ultra Low Light Level Imaging, NASA, Goddard Space Flight Center, SPIE vol. 78 (1976) Low Light Level Devices, pp. 73-77.
Tobin, Kenneth W., Inspection in Semiconductor Manufacturing, Webster's Encyclopedia of Electrical and Electronic Engineering, vol. 10, pp. 242-262, Wiley & Sons, NY, NY, 1999.
Utsumi, TakaoVacuum Microelectrnoics: What's New and Exciting, IEEE vol. 38, No. 10, Oct. 1991, 8 pgs.
Xiaogian, Fu, Higher Quantum Efficiency by Optimizing . . . 978-1-4244-6644-3/10 IEEE, pp. 234-235.
ON Semiconductor, Application Note entitled "Binning Mode Operation for Full Frame CCD Sensors",12 pages, Oct. 2014.

\* cited by examiner

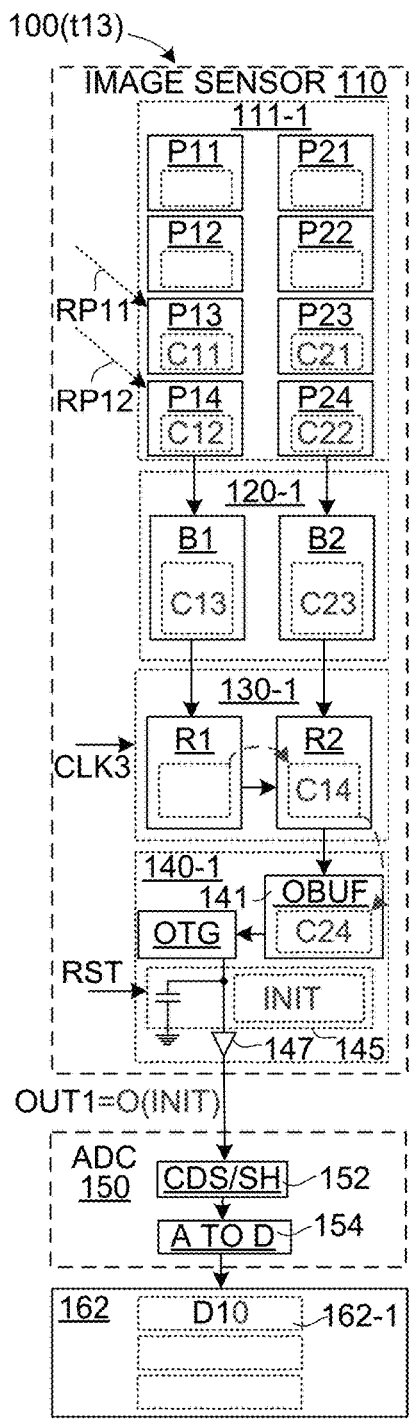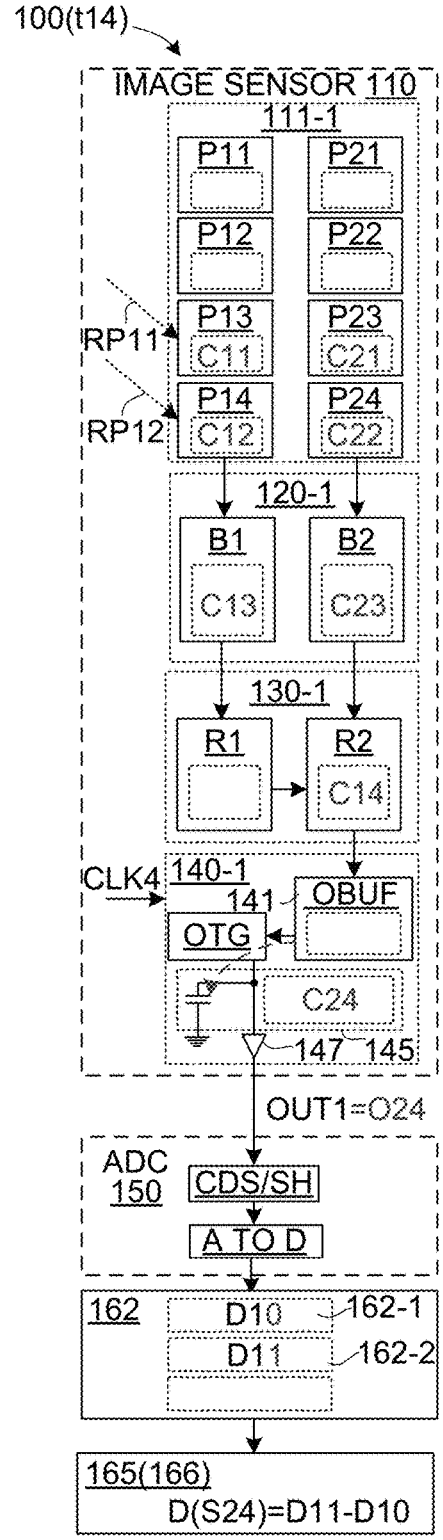
FIG. 2(D)      FIG. 2(E)

DARK-FIELD INSPECTION USING A LOW-NOISE SENSOR

RELATED APPLICATIONS

The present application claims priority to U.S. Provisional Application Ser. No. 62/205,309, filed Aug. 14, 2015.

The present application is related to U.S. patent application Ser. No. 14/273,424 (now U.S. Pat. No. 9,347,890), entitled "A Low-Noise Sensor and an Inspection System Using a Low-Noise Sensor", filed by Brown et al. on May 8, 2014, U.S. patent application Ser. No. 13/792,166, entitled "BACK-ILLUMINATED SENSOR WITH BORON LAYER", filed by Chern et al. on Mar. 10, 2013, U.S. patent application Ser. No. 13/710,315, entitled "ELECTRON-BOMBARDED CHARGE-COUPLED DEVICE AND INSPECTION SYSTEMS USING EBCCD DETECTORS", filed by Chuang et al. on Dec. 10, 2012, U.S. patent application Ser. No. 14/096,911, entitled "METHOD AND APPARATUS FOR HIGH SPEED ACQUISITION OF MOVING IMAGES USING PULSED ILLUMINATION", filed by Brown et al. on Dec. 4, 2013 which claims priority to U.S. Provisional Application 61/735,427, filed by Brown et al. on Dec. 10, 2012, U.S. Pat. No. 8,624,971, entitled "TDI SENSOR MODULES WITH LOCALIZED DRIVING AND SIGNAL PROCESSING CIRCUITRY FOR HIGH SPEED INSPECTION", filed by Brown et al. on Oct. 7, 2009, U.S. Published Patent Application 2011/0073982, entitled "INSPECTION SYSTEM USING BACK SIDE ILLUMINATED LINEAR SENSOR", filed by Armstrong et al. on May 25, 2007, U.S. Pat. No. 7,607,309 B2, entitled "Continuous clocking of TDI sensors", issued to Brown et al. on Oct. 27, 2009, U.S. Pat. No. 7,952,633, entitled "APPARATUS FOR CONTINUOUS CLOCKING OF TDI SENSORS", issued to Brown et al. on May 31, 2011, and U.S. Pat. No. 8,754,972 B2, entitled "INTEGRATED MULTI-CHANNEL ANALOG FRONT END AND DIGITIZER FOR HIGH SPEED IMAGING APPLICATIONS", issued to Brown et al. on Jun. 17, 2014. All these applications and patents are incorporated by reference herein.

BACKGROUND OF THE DISCLOSURE

Field of the Disclosure

The present application relates to image sensors suitable for sensing radiation at visible, ultraviolet (UV), deep UV (DUV), vacuum UV (VUV), extreme UV (EUV), X-ray wavelengths, and for sensing electrons, and to methods for operating such image sensors. The sensors are particularly suitable for use in dark-field inspection systems including those used to inspect photomasks, reticles, and semiconductor wafers.

Related Art

The integrated circuit industry requires inspection tools with increasingly higher sensitivity to detect ever smaller defects and particles whose sizes may be smaller than 20 nm. Those same inspection tools need to be capable of detecting large defects such as scratches and water marks, which may have dimensions ranging from less than 1 µm to multiple mm, and of measuring the wafer surface roughness or haze which may have a peak-to-valley amplitude of a few nm or less than 1 nm.

Small particles, small defects, low contrast defects and low-amplitude roughness scatter light only very weakly. In order to detect small defects or particles on photomasks, reticles, and semiconductor wafers, low-noise sensors are required. Sources of sensor noise include dark current within the sensor, readout noise in the sensor, noise in the electronics that amplifies and digitizes the sensor output signal(s), and noise from external electronics including drivers and controllers that gets coupled into the signal.

Typically inspection systems used in the semiconductor industry are designed to inspect a large area (such as the entire surface of a 300 mm or 450 mm diameter silicon wafer) very quickly, in some cases in one minute or less. Thus the time spent collecting the signal from any one small area of the article being inspected, such as the area corresponding to a single pixel on the sensor, must be very short, in many cases much less than 1 ms.

Increasing the intensity of the light used to illuminate the article being inspected can increase the signal level relative to the noise. However high power densities from the illumination are not only expensive to generate, but they also can degrade the optics of the inspection system and may damage the article being inspected.

An important limitation of prior art CCD sensors and driving circuits can be appreciated by studying FIG. 20. This figure illustrates the timing of the signal readout from a CCD. 1110 represents the output voltage of the sensor as a function of time. 1101 represents the sensor output voltage reset clock voltage as a function of time. The vertical axis represents voltage in arbitrary units and the horizontal axis represents time. The vertical scalings of the output voltage 1110 and the reset clock voltage 1101 are not necessarily equal. The vertical offset in the figure between the output voltage 1110 and the reset clock voltage 1101 is simply for clarity and does not imply that one voltage must be more positive or more negative than the other.

The reset clock 1101 resets the output voltage 1110 so that the signal for the next pixel can be output. When the reset clock 1101 is high (positive) as shown at 1102, the output charge from the prior pixel is discharged so that the output signal settles down to the reset level shown as 1115. Voltage 1110 illustrates several practical issues that can degrade the signal-to-noise ratio and accuracy of the output signal of CCD image sensors, particularly when the sensor is operated at high speed as is required for inspection and metrology applications in semiconductor and related industries. When the reset clock 1101 switches from a low voltage to a high voltage as shown at 1103, some of that voltage swing is coupled to the output signal because the reset transistor is necessarily physically located on the CCD adjacent to the output sensing node. This coupling destabilizes the output signal as shown at 1112. Furthermore when the reset clock goes low as shown at 1104, that high-to-low transition is similarly coupled to the output signal and destabilizes the output signal as shown at 1114. After some time, the output signal settles down and stabilizes at the reset level shown as 1115. When the charge from a pixel is transferred to the output, the voltage decreases from the reference level (because the signal comprises electrons and is, hence, a negative charge) to a level such as 1117. In FIG. 20, level 1117 represents the voltage corresponding to a saturated pixel, i.e. maximum signal, and level 1119 represents the voltage corresponding to a signal level that is significantly less than the maximum. Although not shown, typically there will be some settling time after the transition from the reference level 1115 to the signal level such as 1117 or 1119.

In FIG. 20, the signal in the first pixel is proportional to the difference between voltages 1117 and 1115, and the signal in the second pixel is proportional to the difference between voltages 1115 and 1119. Usually, Correlated Double Sampling (CDS) is used to measure the difference between the reference voltage 1115 and the signal voltage such as 1117 and 1119. Correlated Double Sampling is a well-known technique and is described, for example, by J. R. Janesick, "Scientific Charge-Coupled Devices", SPIE Press, 2001, pp. 556-561.

As can be appreciated from FIG. 11, when the signal needs to be read out at high speed, such as a speed of about 10 MHz or more, there is only a short time for the output voltage 1110 to settle to the reference voltage 1115 and the signal voltages such as 1117 and 1119. For example at 50 MHz, the total time for one pixel is 20 ns. The reset clock pulses must necessarily be much shorter than this with rise and fall times of, at most, 1-2 ns. Such short pulses with fast rise and fall times necessarily cause significant destabilization of the output signal. Only a few ns are available for the output voltage to settle. In some cases, the signal may not have enough time to fully stabilize, leading to analog image data values (captured charges) having low signal-to-noise ratios due, in part, to this reset clock noise component. In the case of un-patterned (bare) or monitor wafer inspection, read noise from an imaging sensor may be the limiting system noise source. That is, higher resolution sampling (a smaller effective pixel size) by the imaging sensor, can, in some cases, unnecessarily reduce system performance.

Therefore, a need arises for an image sensor capable of detecting low light levels at high speed with high spatial resolution and high signal-to-noise ratio, yet overcoming the above disadvantages.

SUMMARY OF THE DISCLOSURE

The present invention is directed to an inspection system and method in which analog image data values captured by an image sensor are binned (combined) before or while being transmitted as output signals on the image sensor's output sensing nodes (also referred to as floating diffusions), and in which an analog-to-digital converter (ADC) is controlled to sequentially generate two or more corresponding digital image data values between each reset of the image sensor's output sensing node (i.e., during each cycle of the sensor's reset clock signal). The present invention is particularly beneficial during the inspection of un-patterned (bare) wafers, where very low surface scatter from the un-patterned wafer produces minimal background noise, so signal-to-noise ratios are largely determined by sensor noise characteristics. The present inventors recognized that the very low surface scatter and low background noise produces analog image data values (i.e., charges captured by the pixels) that may be binned (summed together/combined) before or in the image sensor's output sensing node such that charges from multiple pixels can be simultaneously converted by the ADC, whereby an image sensor capable of performing the higher resolution imaging required for bare wafer inspection (i.e., wafers with no film on their surface) can also be utilized to perform high speed lower resolution imaging preferred, for example, for inspecting wafers with films on their surface. The inventors also recognized that the accuracy of the image data could be significantly improved by increasing the number of digital image data values generated by the ADC between each reset of the image sensor's output buffers. That is, by reducing the ratio of reset clock noise components (i.e., noise generated each time the output buffer is reset) to digital image data values generated by the ADC, the signal-to-noise ratio of image data generated during high speed un-patterned wafer inspection could be greatly improved. By combining charge binning with reduced reset clock noise, the present invention facilitates low resolution/high speed inspection operations capable of detecting low light levels at high speed with high signal-to-noise ratios in a way that facilitates bare wafer inspections while avoiding the drawbacks of prior art approaches. Moreover, because the present invention effectively re-tasks image sensors that are otherwise capable of high-resolution inspection operations typically required for post-processing wafers, the present invention facilitates multi-purpose inspection systems that can be utilized for a wide range of inspection operations, thereby allowing a user to select between inspection speed and sensitivity as required.

The present invention is described with reference to exemplary sample inspection methods (embodiments) that utilize various approaches for driving (i.e., controlling by way of clock, reset and control signals) an image sensor such that multiple analog image data values (i.e., charges captured by the image sensor's pixels) are systematically transferred and binned (i.e., summed together and simultaneously stored) before and/or in the image sensor's output sensing node during each cycle of an reset clock signal, and also utilize various approaches for generating multiple digital data values during each cycle of the reset clock signal.

According to an output binning process (first exemplary embodiment of the invention), the image sensor is driven to sequentially (i.e., one at a time) transfer analog image data values onto the image sensor's output sensing node between each reset, whereby the charge stored on the output sensing node incrementally increases with each analog image data values transfer. In addition, the ADC is driven to convert analog output signals generated in accordance with the progressively increasing stored charge after each analog image data value is transferred onto the output sensing node, thereby generating at least some digital data values that are free from the reset clock noise component described above. In one embodiment, a shift register is utilized to transfer the analog image data signals onto the output sensing node according to timing set by shift register clock signals, as the shift register clock signals are generated at a higher frequency than the reset clock signal such that multiple analog image data values are transferred onto the output sensing node during each cycle of the reset clock signal. Downstream digital signal processing is then utilized, for example, to calculate final (e.g., CDS) image values by way of determining a difference between each sequentially generated analog output signals.

According to a multi-sampling embodiment of the invention, the effect of output buffer reset noise is reduced by way of vertically and/or horizontally binning multiple captured charges before shifting the combined charges onto the output sensing node, then sampling the corresponding image sensor output signal multiple times (i.e., controlling the ADC to generate multiple "duplicate" digital image data values for the same corresponding analog output signal associated with a given combined charge). Vertically binning may be performed by transferring two or more rows of analog image data values onto pixel buffers before transferring the summed signals to a shift register. Horizontal binning may be performed by transferring two or more analog image data values from the shift register into an output buffer before transferring the combined charge in the output buffer to the output sensing node. If the background signal level is low enough relative to the full well capacity of the output buffer, horizontal and vertical binning may be used at the same time. Because the multiple (duplicate) digital image data values are generated while the same combined charge is present in the output buffer, similar to the output binning process mentioned above, the multi-sampling process generates multiple digital data values during each cycle of the reset clock signal. The duplicate digital image data values are then averaged using downstream data processing, thereby effectively reducing the noise below that of any independent measurement (since the noise always has a component that is uncorrelated between samples). That is, the multi-sampling process utilizes time gained during horizontal and/or vertical binning of the analog image data values (captured charges) to sample each sensor output node signal multiple times, whereby noise influences are reduced without slowing down system operations, for example, by way of averaging the duplicated digital data values.

In yet another exemplary embodiment, the output binning and multi-sampling processes described above may be utilized together (i.e., by utilizing vertical binning before progressive transfer to the output sensing node, and/or performing multi-sampling of each analog output value generated in accordance with the output binning process). In all of the exemplary embodiments, binning of image data is utilized to reduce electronic noise in ways that facilitate detecting low light levels at high speed with high spatial resolution and high signal-to-noise ratio while overcoming the disadvantages associated with prior art approaches used for high-speed bare wafer inspection operations.

An exemplary inspection system is described that includes the modifications mentioned above. This inspection system includes an illumination source, optics, and a detector. The optics are configured to direct and focus radiation from the illumination source onto a sample. The sample is supported by a stage, which moves relative to the optics during the inspection. The detector is configured to receive reflected or scattered radiation from the sample, wherein the optics are further configured to collect, direct, and focus the reflected or scattered radiation onto the detector. The detector includes one or more image sensors driven in the manner described herein. In one embodiment, at least one image sensor is a time delay integration (TDI) sensor. The TDI sensor converts the detected radiation into electrical charges. The electrical charges are shifted within the sensor in synchrony with the motion of the stage. In another embodiment, the image sensor is a line sensor. The line sensor converts the detected radiation into electrical charges. In another embodiment, the image sensor is reconfigurable such that multiple pixels can be read out independently. The pixel sensor converts the detected radiation into electrical charges. In any embodiment, the methods and circuits described below are used to improve the signal-to-noise ratio of the signal.

The exemplary inspection system may include one or more illumination paths that illuminate the sample from different angles of incidence and/or different azimuth angles and/or with different wavelengths and/or polarization states. The exemplary inspection system may include one or more collection paths that collect radiation reflected or scattered by the sample in different directions and/or are sensitive to different wavelengths and/or to different polarization states. The exemplary inspection system may include a TDI sensor with readout circuits on two sides that are used to read out two different signals simultaneously. The exemplary inspection system may include an electron-bombarded image sensor.

An exemplary method of inspecting a sample utilizing one of the inspection systems mentioned above is described. The method includes directing and focusing radiation from an illumination source onto the sample. The sample is supported by a stage, which moves relative to the optics during the inspection. The method further includes using optics to collect, direct, and focus radiation reflected or scattered by the sample onto a detector. The detector includes one or more image sensors. In one embodiment, at least one image sensor is a time-delay integration (TDI) sensor. The TDI sensor converts the detected radiation into an electrical charge. The method further includes shifting electrical charges within the sensor in synchrony with the motion of the stage. In another embodiment, at least one image sensor is a line sensor. The line sensor converts the detected radiation into an electrical charge. In both embodiments, charges from more than one pixel may be accumulated in an output buffer of the image sensor before being read out by way of an output sensing node. In another embodiment, at least one image sensor is a pixel sensor that converts radiation into an electrical charge. The pixel sensor comprises an output sensing node configured to accumulate charges from multiple radiation detections. In both cases, an ADC is driven to generate multiple digital data values during each cycle of the reset clock signal utilized to reset the image sensor's output sensing node.

Circuits for controlling, driving and/or reading out a time-delay integration image sensor, a line sensor, or a pixel sensor with an output in each pixel are described. The circuits comprise a generator that generates clock and reset waveforms that reduce the noise coupled into the sensor output and allow the signal from multiple pixels, or multiple readings of the same pixel, to be accumulated in the sensing node of the image sensor before being read out.

Methods for controlling, driving and/or reading out a time-delay integration image sensor, a line sensor, or a pixel sensor with an output in each pixel are described. These methods include generating clock and reset waveforms that reduce the noise coupled into the sensor output and allow the signal from multiple pixels, or multiple readings of the same pixel, to be accumulated in the sensing node of the image sensor before being read out.

BRIEF DESCRIPTION OF THE DRAWINGS

FIGS. 2(A), 2(B), 2(C), 2(D), 2(E), 2(F) and 2(G) are partial block diagrams depicting the inspection system of FIG. 1 during sample inspection using a single pixel processing.

DETAILED DESCRIPTION OF THE DRAWINGS

The present invention relates to an improvement in sensors and the circuits and methods for driving, controlling and/or reading out sensors for semiconductor inspection systems. The following description is presented to enable one of ordinary skill in the art to make and use the invention as provided in the context of a particular application and its requirements. Various modifications to the preferred embodiments will be apparent to those with skill in the art, and the general principles defined herein may be applied to other embodiments. Therefore, the present invention is not intended to be limited to the particular embodiments shown and described, but is to be accorded the widest scope consistent with the principles and novel features herein disclosed.

Figure 1:
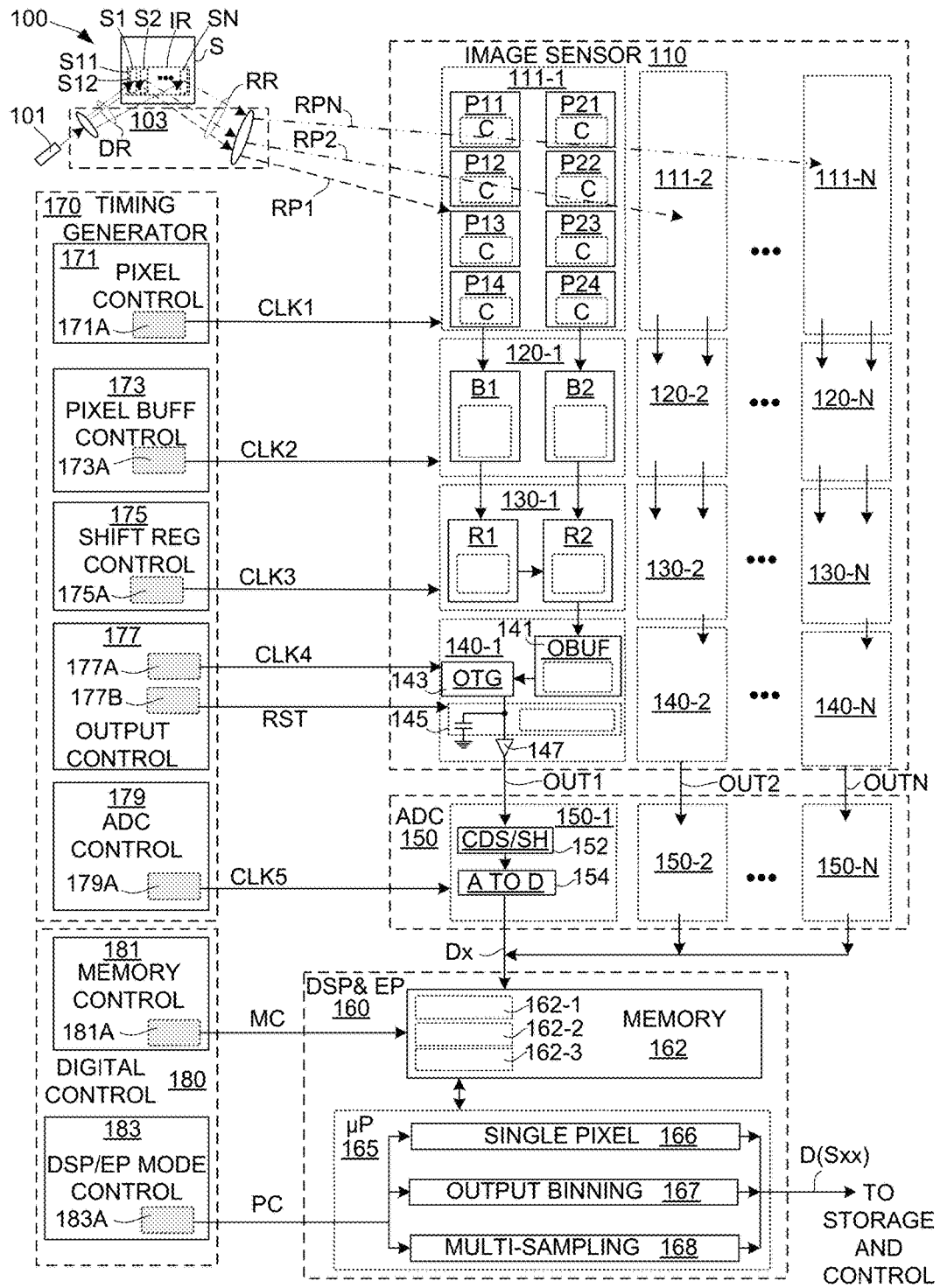
FIG. 1 is a block diagram depicting a simplified inspection system for inspecting a sample using an image sensor and an ADC according to an exemplary generalized embodiment of the present invention.

FIG. 1 is a block diagram depicting a simplified system 100 for inspecting a sample S using an image sensor 110 and an analog-to-digital converter (ADC) 150 according to a generalized embodiment of the present invention. System 100 includes a radiation source 101 (e.g., a laser) and an optical system 103 configured to direct radiation DR onto sample S, and configured to direct received (e.g., reflected) radiation RR from an imaged region IR of sample 100 onto image sensor 110. As explained below, image sensor 110 generates analog output signals OUT1 to OUTN that are converted into digital image data values Dx by ADC 150. System 100 also includes digital signal processing (DSP) and external processing (EP) circuit 160 that receive and processes digital image data values Dx in the manner described below in order to generate final image data values D(Sxx), timing generator circuit 170 that generates clock, reset and control signals utilized to control the operations of image sensor 110 and ADC 150, and digital control circuit 180 utilized to generate other control signals utilized to control ADC 150 and DSP/EP circuit 160. Those skilled in the art will recognize that the operation of system 100, which is described below with reference to certain exemplary embodiments, is greatly simplified herein for brevity.

Referring to the upper portion of FIG. 1, image sensor 110 includes multiple pixels arranged in pixel groups 111-1 to 111-N, and optical system 103 is configured such that portions of received radiation RR received from sections S1 to SN of imaged region IR are directed onto corresponding pixel groups 111-1 to 111-N of image sensor 110. Each pixel group includes an associated group of pixels disposed in multiple rows and multiple columns. For example, pixel group 111-1 includes pixels P11 to P24, where pixels P11 and P21 define (form) an associated top row of four rows, and pixels P11, P12, P13 and P14 are disposed in a leftmost column of two columns. Note that image sensor group 111-1 is depicted as including four rows and two columns merely to simplify the following description—in a practical image sensor useful in high-speed inspection application, each pixel group would typically comprise between two and 16 columns, and between one row (i.e., as in a line sensor) and a few thousand rows. The pixels of pixel groups 111-1 to 111-N are configured in cooperation with optical system 103 to capture and store corresponding analog image data values (charges) having values (charge amounts) determined by the amount of radiation received from a corresponding section of imaged region IR during each imaging operation performed by system 100. For example, at a given moment when imaged region IR is oriented relative to sample S as shown in FIG. 1, each pixel P11 to P24 of pixel group 111-1 captures and stores an image data value (charge C) received by way of radiation portion RP1 from a corresponding imaged region section S1 (e.g., the portion of sample S disposed in the leftmost portion of imaged region IR), thereby causing each pixel P11 to P24 to capture and store a corresponding charge C in the manner described below. At the same time, the pixels of pixel group 111-2 store image data received by way of radiation portion RP2 from a corresponding imaged region section S2, which is adjacent to section S1. In this way, radiation received from each section S1 to SN of imaged region IR is thereby captured by a corresponding pixel group 111-1 to 111-N of image sensor 110 such that the pixels of image sensor 110 capture image data from the entire portion of sample S disposed within imaged region IR. Similarly, each pixel of each pixel group stores image data received from a corresponding sub-section of each imaged region section.

Figure 1A:
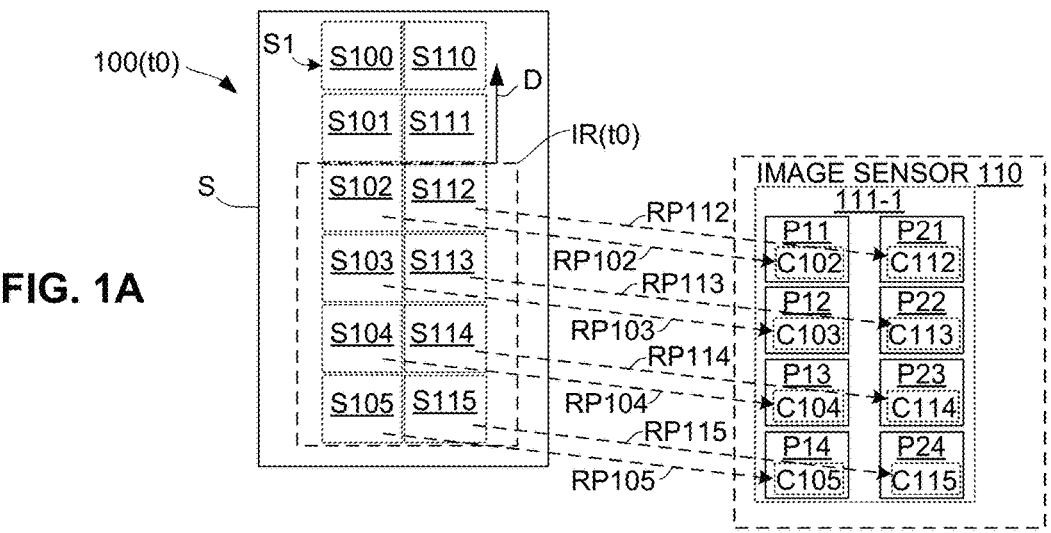
FIGS. 1A, 1B and 1C are partial block diagrams depicting simplified image capture and image transfer operations performed by the inspection system of FIG. 1 during a sample inspection operation according to an exemplary embodiment of the present invention.

Referring to FIG. 1A, pixels P11 to P24 of pixel group 111-1 receive corresponding light portions RP102 to RP115 reflected/emitted from corresponding sub-sections of section S1 of sample S, whereby each pixel receives and stores a corresponding charge C102 to C115 having an amount determined by the amount of radiation received during a given time period. For example, pixel P11 captures received radiation portion RP102 from sub-section S102 of sample S, and generates/stores a corresponding charge C102. Similarly, pixel P21 generates/stores charge C112 in accordance with a radiation amount associated with radiation portion R112 received from sub-section S112, pixel P12 generates/stores charge C103 generates/stores charge C103 in accordance with radiation portion R103 received from sub-section S103, etc.

According to a presently preferred embodiment, system 100 performs scanning-type inspection operations during which the sample S is translated relative to optical system 103 and image sensor 110. The charges stored in image sensor 110 are shifted in a coordinated manner such that captured image data from sample S is transferred along the columns of pixels of image sensor 110 in coordination with a scanning movement of sample S. The coordinated movement of sample S and the charges stored in image sensor 110 during image capture and image data transfer operations is depicted in a simplified form in FIGS. 1A to 1C, which respectively show portions of system 100 at sequential times t0, t1 and t2 (indicated by "100(t0)", "100(t1)" and "100(t2)" in FIGS. 1A to 1C, respectively). Each of these figures shows an enlarged section S1 of sample S and pixel group 111-1 of image sensor 110 (other portions of sample S and system 100 are omitted for brevity). For explanatory purposes, section S1 is divided into sub-sections S100 to S115, which correspond to adjacent minute regions of sample S.

FIG. 1A shows system 100 at an initial time t0 when the optical system (not shown) is positioned relative to sample S such that imaged region IR(t0) encompasses sub-sections S102 to S115 of section S1. As explained above, at this time radiation from sections S102 to S115 is directed to pixel group 111-1 by way of radiation (light) portions RP102 to RP115, whereby pixels P11 to P24 respectively capture/store charges C102 to C115 based on the amount of received light from sub-sections S102 to S115.

Figure 1B:
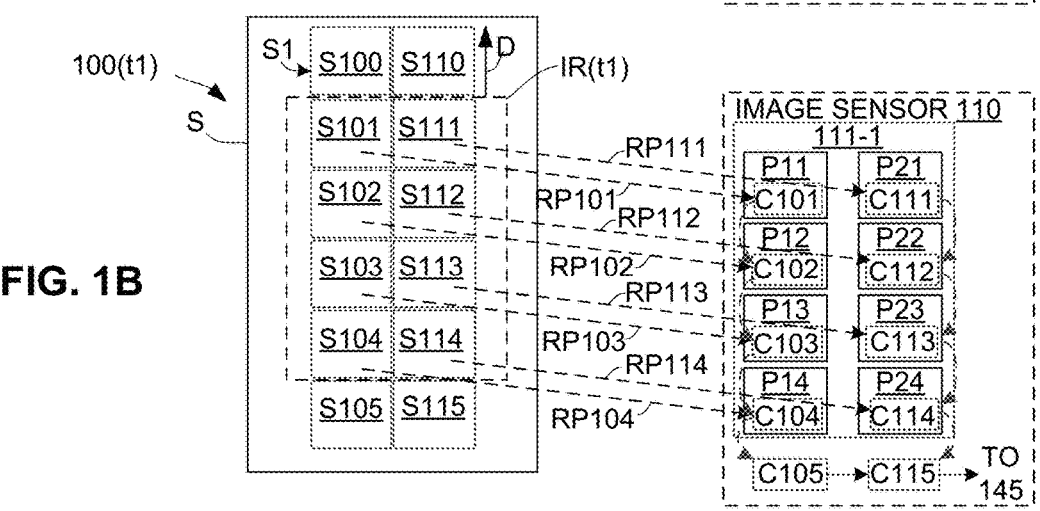

FIG. 1B shows system 100(t1) after movement of sample S relative to the optical system (not shown) causes imaged region IR(t1) to move incrementally upward (i.e., in direction D) relative to sample S, whereby imaged region IR(t1) encompasses sub-sections S101 to S114 of section S1. This relative motion may be achieved, for example, by moving sample S in a downward direction in FIG. 1A while keeping the optical systems and sensor stationary. Referring to the right side of FIG. 1B, at the same time imaged region IR is moved incrementally in direction D, and image sensor 110 is simultaneously driven (i.e., controlled by way of clock, reset and other control signals described below) such that the analog image data values (i.e., charges C102 to C115) are generated and systematically transferred from pixels P11 to P24 toward output sensing node 145. Specifically, as imaged region IR(t1) shifts to encompass sub-sections S101 to S114, image sensor 110 is driven to shift charges C102 to C115 downward, whereby charges C102 to C114 are shifted from pixels P11-P23 to pixels P12-P24 (as indicated by the curved dashed arrows in FIG. 1B), and charges C105 and C115 are shifted out of pixel group 111-1 for transfer to output sensing node 145 in the manner described below. Note that the downward shifting of charges C102 to C114 is coordinated with the movement of imaged region IR(t1) such that each of these charges continues to be influenced by radiation received from the same sub-section of sample S as at time t0. That is, charge C102, which is now stored in pixel P12, is influenced by radiation portion RP102 transmitted from sub-section S102. Note also that sub-sections 101 and 111, which are effectively added to imaged region IR(t1), transmit radiation portions RP101 and RP111, respectively, that are transmitted by way of the optical system (not shown) to pixels P11 and P12.

Figure 1C:
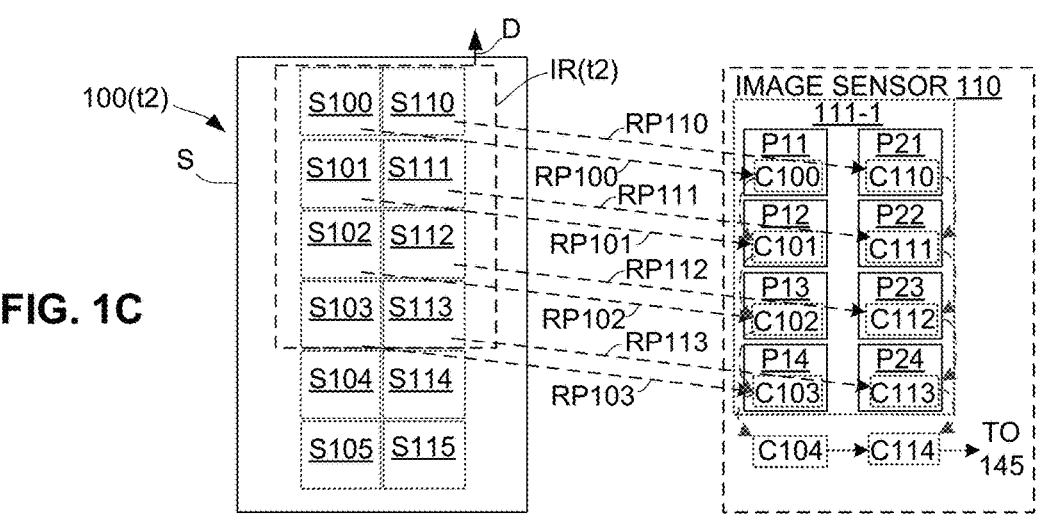

FIG. 1C shows system 100(t2) after an additional incremental movement in direction D of the imaged region IR of sample S relative to the optical system (not shown) causes imaged region IR(t2) encompass sub-sections S100 to S113 of section S1. Similar to that shown in FIG. 1B, image sensor 110 is driven to systematically transfer charges C101 to C113 downward from pixels P11 to P24, and to transfer charges C104 and C114 out of pixel group 111-1 for transmission on output sensing node 145. By continuously driving image sensor 110 in coordination with movement of the optical system relative to the sample in the manner described above with reference to FIGS. 1A to 1C, analog image data is continuously captured during the scanning-type inspection operation performed by system 100.

Referring again to FIG. 1, image sensor 110 also includes optional pixel buffers 120-1 to 120-N, shift registers 130-1 to 130-N and output circuits 140-1 to 140-N configured to transfer analog image data values captured by the pixels to output sensing node 145 for transmission to ADC 150. Note that each of these circuits is described in accordance with the two columns in each pixel group of the simplified embodiment. Thus, pixel buffers 120-1 to 120-N respectively include two charge storage cells B1 and B2 that receive and buffer (temporarily store) one row of analog image data values transferred in parallel from pixel groups 111-1 to 111-N. Similarly, shift registers 130-1 to 130-N include two storage cells R1 and R2 respectively configured to receive and buffer analog image data values transferred in parallel from buffers 120-1 to 120-N, and configured to shift the analog image data values in series to associated output circuits 140-1 to 140-N. Each output circuit (e.g., output circuit 140-1) may include an optional output buffer 141 configured to receive and buffer analog image data values received from an associated shift register (e.g., shift register 130-1), and also includes an output transfer gate 143, output sensing node 145, and an output driver 147 configured to generate an associated analog output signals OUT1 to OUTN using known techniques. The operations of optional pixel buffers 120-1 to 120-N, shift registers 130-1 to 130-N and output circuits 140-1 to 140-N are described in greater detail below.

ADC 150 includes multiple analog-to-digital converter units 150-1 to 150-N that respectively convert analog output signals OUT1 to OUTN into corresponding digital output values Dx that are then transferred to DSP/EP circuit 160. As indicated by unit 150-1, each unit 150-1 to 150-N includes a correlated double sampling and sample-and-hold circuits (CDS/SH) 152 configured to pass a corresponding analog output signal (e.g., output signal OUT1) to a converter circuit 154.

DSP/EP circuit 160 includes a memory circuit 162 including multiple digital registers (e.g., registers) 162-1 TO 162-3 configured to receive and store digital image data values Dx for processing by way of microprocessor (μP) 165. According to an aspect of the present invention, microprocessor 165 is configured to perform one or more data processing operations according to output binning process 167 described below with reference to FIGS. 3(A) to 3(I), and multi-sampling process 168 described below with reference to FIGS. 4(A) to 4(I). In one embodiment, timing generator 170 and digital control circuit 180 are configured such that system 100 is selectively reconfigurable by way of operator commands to perform during a given time period one of a conventional (single pixel) process 166, which is described below with reference to FIGS. 2(A) to 2(G), or one of output binning process 167 and multi-sampling process 168, which are described below with reference to FIGS. 3(A) to 4(I). For purposes of graphically depicting the reconfigurable functionality of system 100, the functional circuitry of timing generator 170 is depicted using a pixel control circuit 171, a pixel buffer control circuit 173, output circuit control circuit 177, and a ADC control circuit 179, and digital control circuit 180 is depicted to include a memory control circuit 181 and a DSP/EP mode control circuit 183. These various circuits are depicted as being reconfigurable by way of user-supplied control data that cause timing generator 170 to generate clock signals CLK1 to CLK5 and reset clock signal RST, and cause digital control circuit 180 to generate memory control signal MC and processor control signal PC in a manner that controls image sensor 110, ADC 150 and DSP/EP circuit 160 such that these circuits operate in accordance with a selected one of single pixel process 166, output binning process 167 and multi-sample process 168 during the given time period (note that blocks 166-168 in FIG. 1 are graphical depictions of alternative operating software programs executed by processor 165, and are not intended to represent separate hardware). For example, pixel control circuit 171 generates two or more clock signals CLK1 that control the image capture and charge shifting operations of pixel groups 111-1 to 111-N in accordance with mode control data stored in memory location 171A. In a similar manner, pixel buffer control circuit 173 generates clock signals CLK2 that control the charge buffering operations of buffer circuits 120-1 to 120-N according to mode control data stored in memory location 173A, shift register control circuit 175 generates clock signals CLK3 that control the operation of shift register circuits 130-1 to 130-N according to mode control data stored in memory location 175A, output control circuit 177 generates output circuit clock signal CLK4 and reset clock signal RST that control the operation of output control circuits 140-1 to 140-N according to mode control data stored in memory locations 177A and 177B, and ADC control circuit 179 generates clock signals CLK5 that controls the timing of analog-to-digital conversion operations of ADC circuits 150-1 to 150-N according to mode control data stored in memory location 179A. Similarly, digital control circuit 180 controls digital data storage and transfer operations of memory circuit 162 in accordance with control data stored in memory location 181A, and mode control circuit 183 controls the operations performed by microprocessor 165 in accordance with mode control data stored in memory location 183A, whereby final image data values D(Sxx) are generated in accordance with one of processes 166 to 168 that is determined by the mode control data value stored in memory location 183A. Each of the clock, reset and control signals is generated according to the corresponding currently-stored control data such that image sensor 110, ADC 150 and DSP/EP 160 operate in the manner described below. Those skilled in the art will recognize that the various control circuits and control signals depicted in FIG. 1 are greatly simplified for purposes of description, and that the functions and control signals utilized in the description below are utilized solely for purposes of describing the present invention, and are not intended to limit the appended claims unless otherwise specified in the claims.

According to an aspect of the present invention, ADC 150 is controlled such that two or more analog image data values are converted to digital image data values during each cycle of reset clock signal RST (i.e., between each reset of output sensing node 145 of each output circuit 140-1 to 140-N). Referring to pixel group 111-1 in FIG. 1, analog image data values C11 to C24 are respectively generated in pixels P11 to P24, and are then systematically transferred to output sensing node 145 for transmission to ADC 150 as analog output signal OUT1, and ADC 150 converts analog output signals OUT1 to digital data values Dxx that are stored in memory 162 for further processing by DSP/EP 160. As described below with reference to FIGS. 2(A) to 2(G), when system 100 is configured to perform conventional single pixel processing (block 166 in FIG. 1), each analog image data value C11 to C24 is individually transferred to output buffer 141 and from output buffer 141 to output sensing node 145 for conversion to a corresponding digital image data value by ADC 150-1 between each reset of output sensing node 145 (i.e., output sensing node 145 is reset to an initial value (reset charge state) by reset clock signal RST after each analog image data value C11 to C24 is transmitted as output signal OUT1). In contrast, when system 100 is configured to perform either output binning process 167 (as described below with reference to FIGS. 3(A) to 3(D)) or multi-sampling process 168 (as described below with reference to FIGS. 4(A) to 4(I)), output sensing node 145 is utilized to selectively simultaneously sum (store) two or more analog image data values, and ADC 150-1 is controlled to generate two or more digital image values during each cycle of reset clock signal RST, whereby system 100 optimized for detecting low light levels at high speed with high spatial resolution and high signal-to-noise ratio, thereby overcoming the disadvantages of conventional approaches.

The present invention will now be described with reference to simplified exemplary embodiments utilizing partial block diagrams showing portions of inspection system 100 (FIG. 1). Specifically, FIGS. 2(A) to 2(G) depict inspection operations performed by inspection system 100 when configured to perform single pixel processing 166, FIGS. 3(A) to 3(D) depict systematic shifting of analog image charges from image sensor 110 to ADC 150 when system 100 is configured to perform output binning process 167, and FIGS. 4(A) to 4(F) depict systematic shifting of analog image charges from image sensor 110 to ADC 150 when system 100 is configured to perform multi-sampling processing 168. During the inspection operation associated with each example, sample S is moved and light is continuously collected and transferred for conversion to digital data in a manner similar to that described above with reference to FIGS. 1A, 1B and 1C. For brevity, the exemplary operations are described with reference only to analog image data values (charges) generated in pixel group 111-1 at a given initial moment, with the understanding that charges are continuously simultaneously generated and processed in the described manner before and after the exemplary operations, and simultaneously performed in the other pixel groups of image sensor 110. In addition, for brevity, the figures only depict charges and clock, reset and control signals utilized during relevant portions of the exemplary operations. Note that the figures, for descriptive purposes, generally depict some image processes as if performed simultaneously and other image processes as if performed sequentially. In a practical implementation, the precise timing of the image processes may differ from that described, where some of the depicted simultaneous processes may be performed at different times, and some of the depicted sequential processes may be performed substantially simultaneously.

Figure 2A:
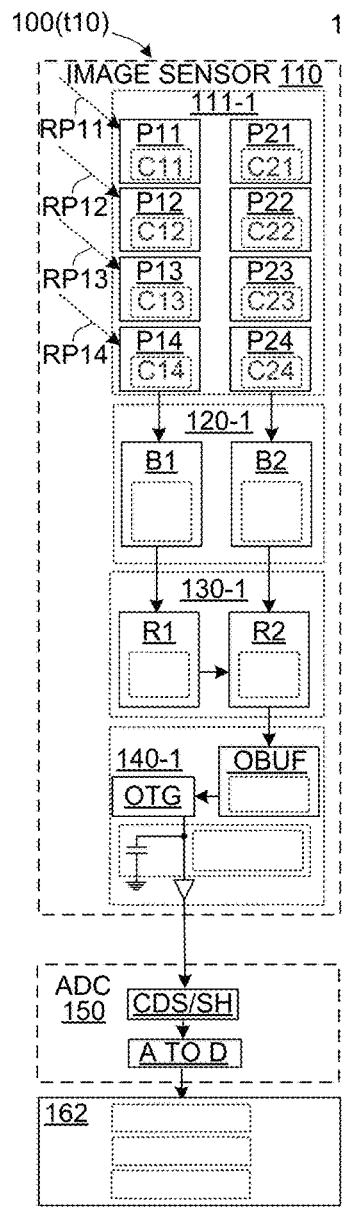
Figure 2B:
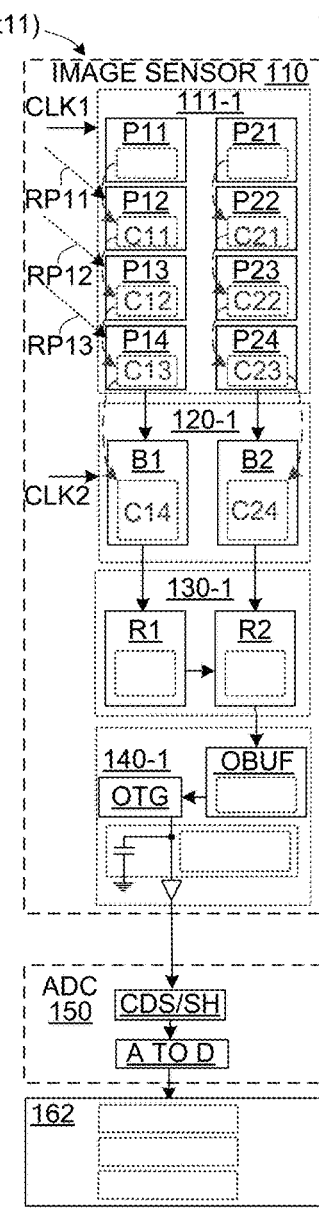
Figure 2C:
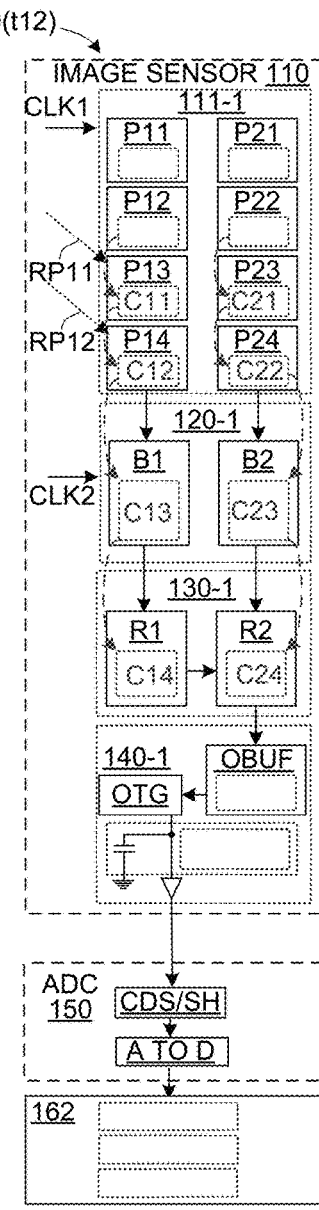

FIGS. 2(A) to 2(C) depict image capture and initial charge transfer operations commonly utilized by the single pixel, output binning and multi-sampling processes described below, and are performed using techniques similar to those known in the art. FIG. 2(A) shows system 100(*t*0) (i.e., system 100 at time t0) when pixels P11 to P24 of pixel group 111-1 are positioned to receive respective radiation portions from a sample (not shown), and generate corresponding analog image data values (charges) C11 to C24 in the manner described above. For example, pixel P11 is positioned to receive radiation portion RP11, thereby capturing/storing charge C11. Similarly, pixel P12 captures/stores charge C12 in response to received radiation portion RP12, pixel P13 captures/stores charge C13 in response to received radiation portion RP13, and pixel P14 captures/stores charge C14 in response to received radiation portion RP14. FIG. 2(B) depicts system 100(*t*11) at subsequent time t11 after the sample has moved incrementally in relation to image sensor 110 and the optics (not shown), and pixel buffer 111-1 is driven to shift charges C11 to C24 in the manner described above with reference to FIGS. 1A to 1C. Specifically, image sensor 110 is driven by clock signals CLK1 to shift charges C11 to C24 downward, whereby charges C11 to C23 are shifted from pixels P11-P23 to pixels P12-P24 (as indicated by the curved dashed arrows in FIG. 2(B)), and charges C14 and C24 are shifted out of pixel group 111-1 and into charge storage cells B1 and B2 of pixel buffer 120-1. At the same time, clock signal CLK2 transfers any pre-existing charges in charge storage cells B1 and B2 to storage cells R1 and R2 of shift register 130-1 (this transfer is not shown as the pre-existing charges are not pertinent to the current explanation). Note that the downward shifting of charges C11 to C23 is coordinated with the movement of a corresponding imaged region (not shown) such that each of these charges continues to be influenced by radiation received from the same sub-section of the inspected sample (not shown). That is, charge C11, which is now stored in pixel P12, is influenced by radiation portion RP11, which is now directed onto pixel P12. Similarly, radiation portions RP12 and RP13 are shifted downward and directed onto pixels P13 and P14, respectively. FIG. 2(C) depicts system 100(*t*11) at subsequent time t12 after charges C14 and C24 are shifted out of pixel buffer 120-1 by way of clock signal CLK2 such that these charges are transferred into storage cells R1 and R2 of shift register 130-1. As depicted in FIG. 2(C), this transfer may be done simultaneously with a vertical transfer similar to that depicted in FIG. 2(B) that transfers charges C13 and C23 into pixel buffer 120-1.

Figure 2F:
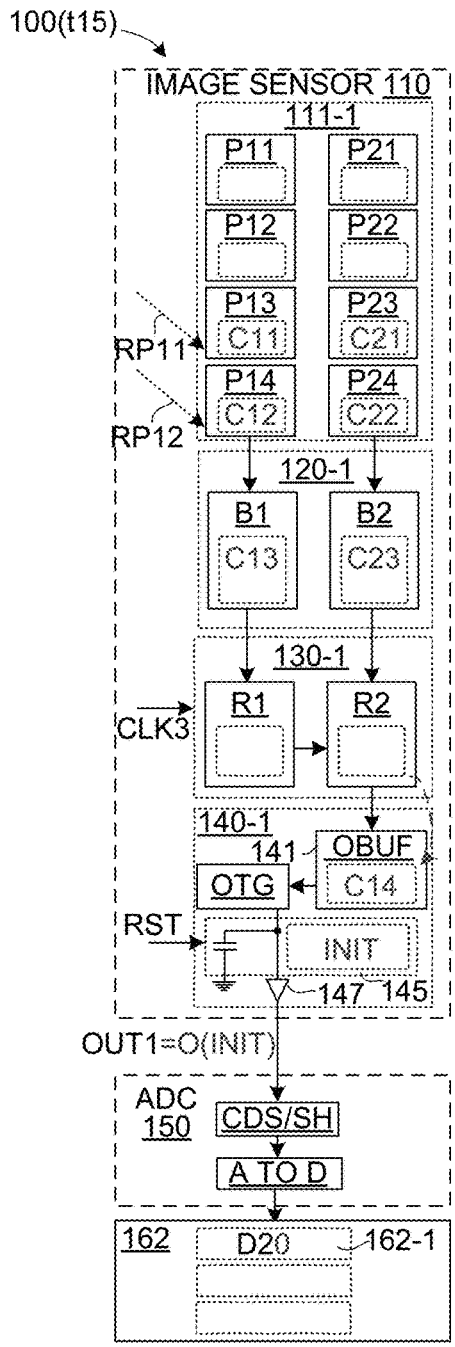
Figure 2G:
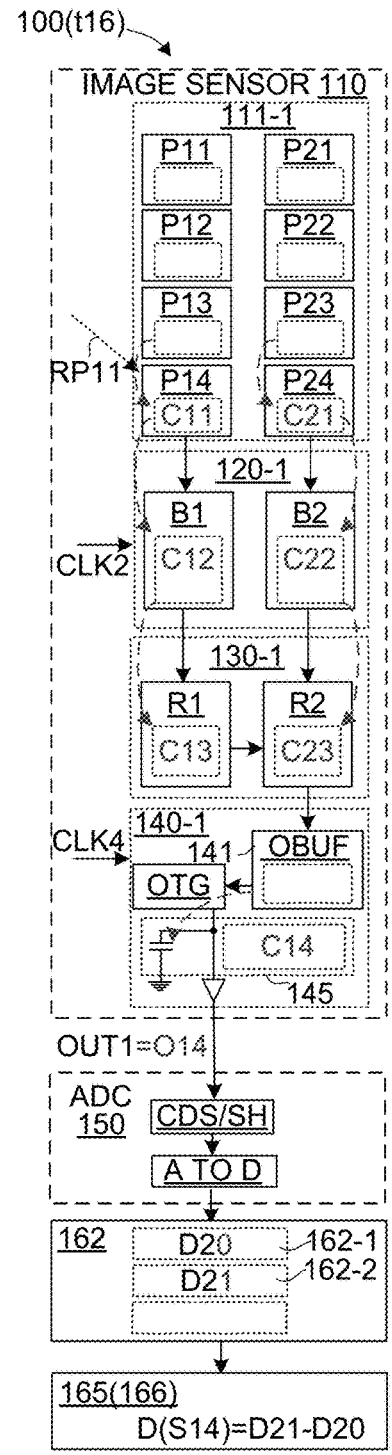

FIGS. 2(D) to 2(G) depict the subsequent transfer and conversion of a row of analog image data values (i.e., charges C14 and C24) into corresponding digital data values utilizing well known correlated double sampling (CDS) techniques. As depicted in FIG. 2(D), at time t13 shift register 130-1 is driven by clock signal CLK3 to shift charge C24 from storage cell R2 of shift register 130-1 into output buffer 141. At approximately the same time, output sensing node 145 is caused to reset by way of actuating reset signal RST, whereby an initial (reset) charge value stored on output sensing node 145 generates a corresponding output signal OUT1 (i.e., by way of amplification by driver 147) having an initial (reset) analog value O(INIT) corresponding to charge INIT. In addition, ADC 150 is driven by way of associated control signals to store output signal analog value O(INIT), for example, on a capacitor in CDS circuit 152, or, alternatively digitized by analog-to-digital converter 154 and stored as digital value D10 in a memory location 162-1 of memory circuit 162. Next, as indicated in FIG. 2(E), output circuit 140-1 is driven by clock signal CLK4 to transfer analog image data value C24 from output buffer 141 to output sensing node 145, thereby generating output signal OUT1 having a voltage O24 corresponding to the level of charge C24, and ADC 150 is driven, for example, to convert output voltage O24 into a digital value D11 that is stored in a memory location 162-2 of memory circuit 162. As indicated at the bottom of FIG. 2(E), in one embodiment, a CDS (final) image data value D(S24) for a corresponding sub-section of the sample (not shown) is then generated by determining a difference between digital values D10 and D11, which is performed, e.g., by way of controlling microprocessor 165 using instructions associated with single pixel process software 166 (i.e., if the subtraction has not been performed in the CDS circuit). As depicted in FIG. 2(F), at time t15 shift register 130-1 is again driven by clock signal CLK3 to shift charge C14 from storage cell R2 into output buffer 141, output sensing node 145 is again reset by reset clock signal RST to initial charge INIT, and ADC 150 is driven, e.g., to digitize and store output signal OUT1 (i.e., signal value O(INIT)) as digital value D20 in a memory location (e.g., location 162-1) of memory circuit 162. At time t6, as indicated in FIG. 2(G), output circuit 140-1 is again driven by clock signal CLK4 to transfer analog image data value C14 from output buffer 141 to output sensing node 145, thereby generating output signal OUT1 having a voltage O24 corresponding to the level of charge C14, ADC 150 is driven, for example, to convert output voltage O14 into a digital value D21 that is stored in a memory location 162-2 of memory circuit 162, and then a CDS image data value D(S14) is generated by determining a difference between digital values D20 and D21. As evidenced by the conversion of the first row to digital values (described above), a characteristic of the single pixel process is that output sensing node 145 is reset between each analog image data value (e.g., between charges C24 and C14).

Once the last analog image data value has been transferred either to output buffer 141 or to output sensing node 145, an additional row of data is shifted downward for processing. For example, as indicated in FIG. 2(G), the next row of charges C13 and C23 are shifted into storage cells R1 and R2 of shift register 130-1. Charges C23 and C13 will be shifted into output circuit 140-1 for generation of CDS image data values in the manner described above for charges C24 and C14.

Figure 3A:
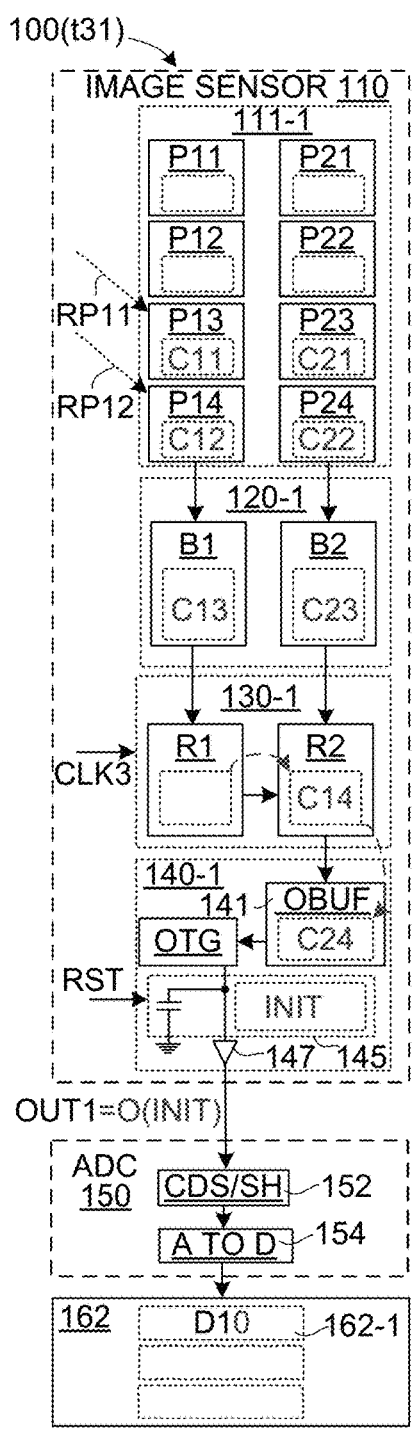
FIGS. 3(A), 3(B), 3(C) and 3(D) are partial block diagrams depicting the inspection system of FIG. 1 during sample inspection using an output binning process according to an exemplary embodiment of the present invention.

FIGS. 3(A) to 3(D) depict the operation of system 100 (FIG. 1) when configured by way of control data to perform output binning process 167 (FIG. 1). To simplify the description, the same charge designations (i.e., C11 to C24) utilized in the description of single pixel processing are also utilized in this example. Note that the output binning process includes image capture operations that are identical to those described above with reference to FIGS. 2(A) to 2(C), and therefore the image capture operations associated with FIGS. 2(A) to 2(C) are omitted below for brevity. That is, the description of the output binning process illustrated in FIGS. 3(A) to 3(D) begins with captured analog image data values C14 and C24 already transferred within image sensor 110, as indicated in FIG. 2(C), where FIG. 3(A) depicts a subsequent charge transfer performed in accordance with the output binning process at a time t31 that is subsequent to time t12 (FIG. 2(C)).

Figure 3B:
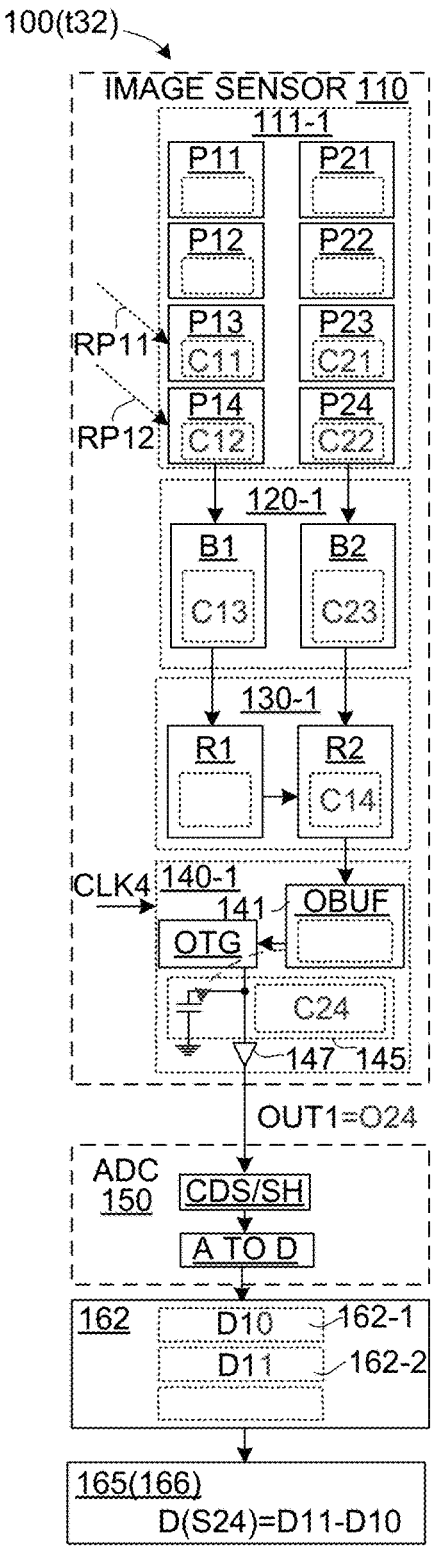
Figure 3C:
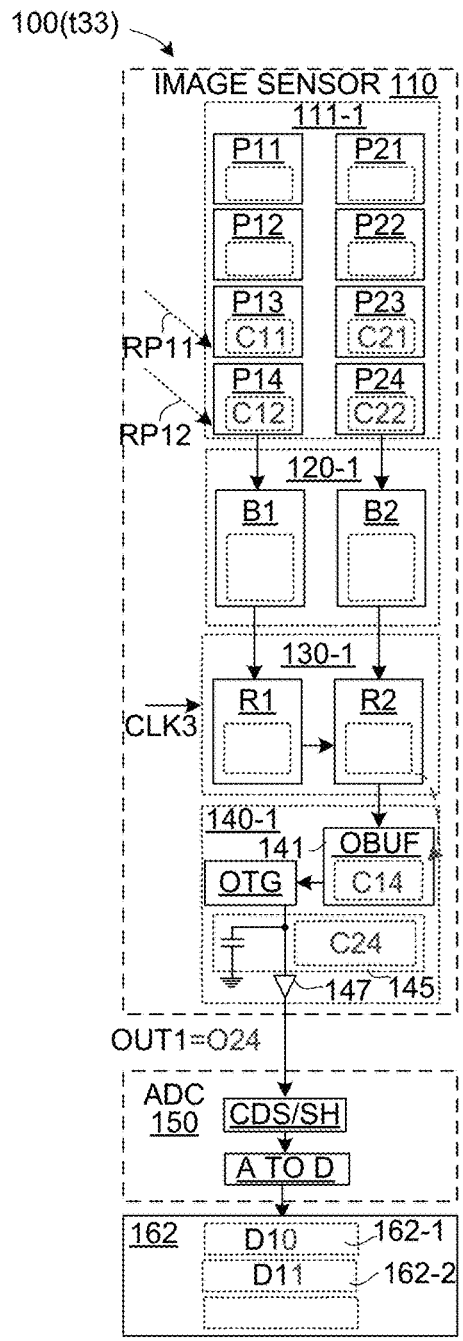
Figure 3D:
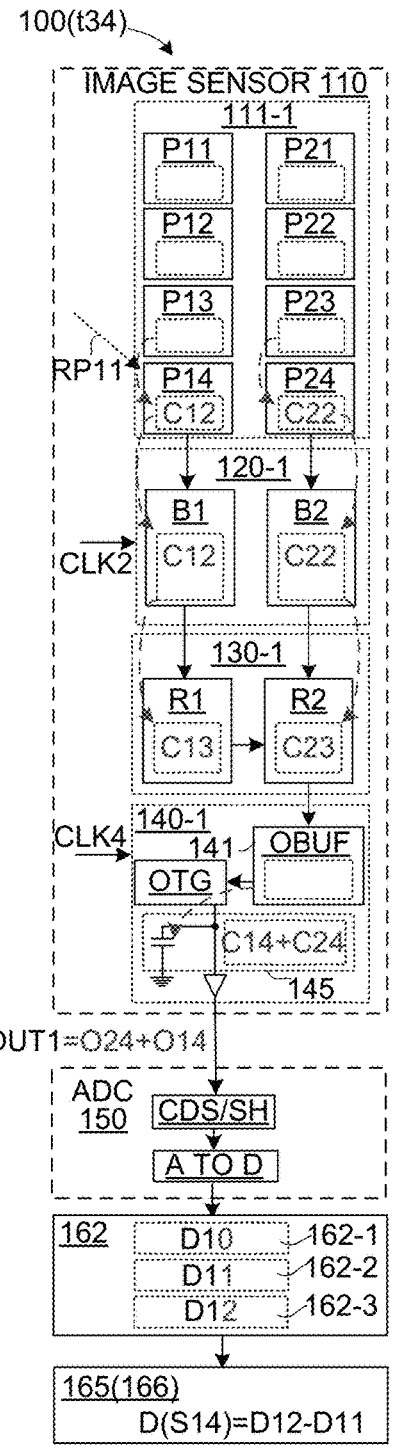

Referring to FIG. 3(A), according to an aspect of the output binning process, image sensor 110(*t*31) is driven to sequentially transfer two analog image data values (i.e., C24 and C14) onto output sensing node 145 such that output sensing node 145 stores a first analog image data value during a first time period (i.e., referring to FIG. 3(A), charge C24 is stored on sensing node 145 at time t31), and stores a sum of the two analog image data values (i.e., the sum of charges C14 and C24, indicated as "C14+C24" in FIG. 3(D)) during a second time period (i.e., subsequent to the first time period). Specifically, output buffer 140-1 is driven using clock signal CLK4 to transfer analog image data value C14 into output sensing node 145 while analog image data value C24 remains stored on output sensing node 145 (i.e., output sensing node 145 was not reset after generating digital data value D11 corresponding to charge C24).

According to this exemplary embodiment, output binning involves controlling ADC 150-1 to generate a first corresponding digital output data value during a first time period while one charge is stored on output sensing node 145, and then generating a second corresponding digital output value during a subsequent (second) time period when a sum of two charges are stored on output sensing node 145. This aspect is illustrated in FIGS. 3(B) and 3(D), where FIG. 3(B) depicts controlling ADC 150-1 to generate a first corresponding digital output data value (i.e., D11) during first time period (time t32) while only charge C24 is stored on output sensing node 145, and FIG. 3(D) depicts controlling ADC 150-1 to generate a second corresponding digital output data value (i.e., D12) during second time period t34 depicted in FIG. 3(D) while the sum of charges C14 and 24 is stored on output sensing node 145. Digital output value D11 is stored in memory location 162-2 in the example of FIG. 3(B), and FIG. 3(D) shows digital value D12 stored in memory location 162-3 of memory 162. Note that the two digital image data values (i.e., D11 and D12) stored in memory 162 at the end of the second time period were generated after the output buffer reset shown in FIG. 3(A).

According to the exemplary embodiment, downstream digital signal processing is utilized to calculate individual pixel values using the progressively generated digital image data values. For example, after calculating CDS image data value D(S24) by way of subtracting reset data value D10 from data value D11 (i.e., as described above with reference to FIG. 2(E), and shown also in FIG. 3(B)), CDS image data value D(S14) is then calculated determining a difference between data values D12 and D11, as indicated at the bottom of FIG. 3(D). In other embodiments, digital data values D10 to D12 may be utilized for other purposes, such as utilizing the calculated differences to determine the reset clock noise component generated at each reset of output buffer 141.

FIG. 3(B) depicts the transfer to the output sensing node and digitization of charge C24. FIG. 3(C) depicts the transfer of charge C14 to the output buffer 141. Note that, in contrast to the corresponding step shown in FIG. 2(F), there is no reset operation at this step. This allows more time for the signal to settle after the transfer to the output sensing node depicted in FIG. 3(B). The digitization of output O24 from charge C24 may be done at time t32 as depicted in FIG. 3(B) or delayed a little until a time between t32 and t33.

According to an aspect of the output binning process, the rate at which output sensing node 145 is reset to initial value INIT is equal to two or more cycles of shift register clock signal CLK3. That is, analog image data values are serially transferred by way of shift register 130-1 into output circuit 140-1 such that one analog image data value is transferred to output sensing node 145 during each cycle of shift register clock signal CLK3 (i.e., output circuit clock signal CLK4 is the same as shift register clock signal CLK3). For example, FIGS. 3(A) and 3(C) depict the transfer of analog image data values C24 and C14 such that charge C24 is transferred onto output sensing node 145 during a first cycle of shift register clock signal CLK3 (as depicted in FIG. 3(A)), and charge C14 is transferred onto output sensing node 145 during a next sequential cycle of shift register clock signal CLK3 (as depicted in FIG. 3(C)). Because two analog image data values C24 and C14 are transferred to output buffer 141 for just the one reset operation depicted in FIG. 3(A), the exemplary embodiment shows that the rate at which output sensing node 145 is reset to initial value INIT is equal to two or more cycles of shift register clock signal CLK3.

Figures 4A, 4B, 4C:
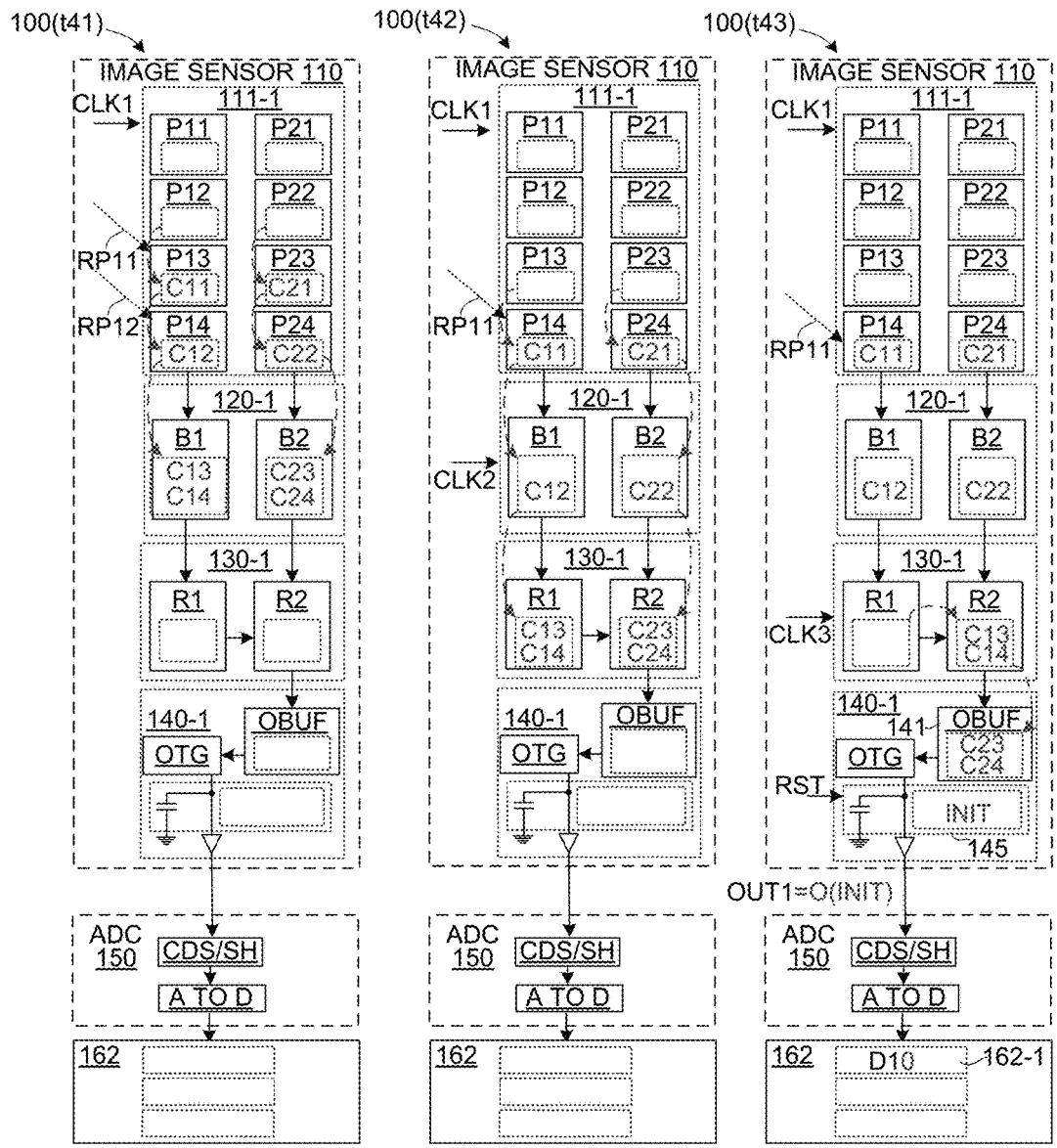
FIGS. 4(A), 4(B), 4(C), 4(D), 4(E), and 4(F) are partial block diagrams depicting the inspection system of FIG. 1 during sample inspection using a multi-sampling process according to another exemplary embodiment of the present invention.

FIGS. 4(A) to 4(F) depict the operation of system 100 (FIG. 1) when configured by way of control data to perform multi-sampling process 168 (FIG. 1). Note that the multi-sampling process begins by performing image capture and initial analog image data transfer operations that are identical to those described above with reference to FIGS. 2(A) and 2(B), and therefore these image capture and initial analog image data transfer operations are omitted below for brevity. That is, the description of the multi-sampling process begins with captured analog image data values already transferred within image sensor 110 at time t11 as indicated in FIG. 2(B), and FIG. 4(A) depicts a subsequent charge transfer performed at a subsequent time t41 in accordance with the multi-sampling process.

According to a first aspect of an exemplary embodiment of the multi-sampling process, multiple pixel charges (analog image data values) are "vertically" binned in pixel buffers B1 and B2 of pixel buffer circuit 120-1 before being passed to shift register 130-1. FIG. 4(A) shows the transfer of charges C13 and C23 into pixel buffers B1 and B2 after charges C14 and C24 were transferred as described above with reference to FIGS. 2(A) and 2(B), whereby summed (combined) charge C13+C14 is stored in pixel buffer B1 and summed charge C23+C24 is stored in pixel buffer B2. Note that binning combined charges in pixel buffers B1 and B2 facilitates transferring charges out of pixel group 111-1 at a faster rate than could be achieved using the single transfer rate described above with reference to FIGS. 2(A) to 2(G) (i.e., clock signal CLK1 can be generated at a higher frequency).

Figure 4D:
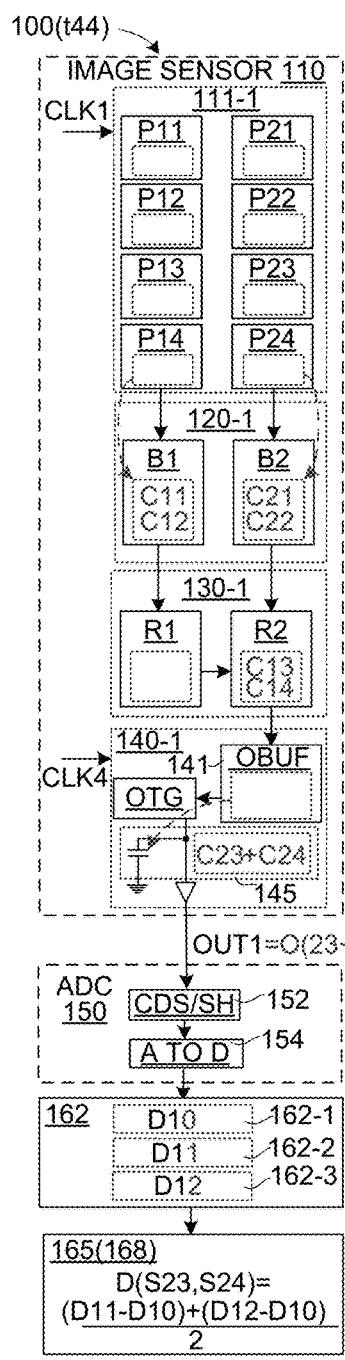

In one embodiment, the subsequent transfer of summed charges to output sensing node 145 for conversion to digital image data values is similar to that utilized in the single pixel process described above. Referring to FIG. 4(B), at time t42 pixel buffer circuit 120-1 is controlled by clock signal CLK2 to transfer summed charge C13+C14 from pixel buffer B1 to register R1 of shift register 130-1, and to transfer summed charge C23+C24 from pixel buffer B2 into register R2. At the same time, a vertical transfer moves all the charges in pixel group 111-1 down one row, resulting in charge C11 transferring from pixel P13 to pixel P14, charge C21 transferring from pixel P23 to pixel P24, and charges C12 and C22 transferring from pixels P14 and P24 to pixel buffer 120-1. Referring to FIG. 4(C), at time t43 shift register is driven by clock signal CLK3 to shift summed charge C13+C14 from register R1 to register R2, and to transfer summed charge C23+C24 from register R2 to output buffer 141. At approximately the same time, output sensing node 145 is reset by way of reset clock signal RST to store initial charge value INIT, and the corresponding output signal OUT1 is converted to generate initial digital image data value D10, which is stored in memory location 162-1 of memory 162. Referring to FIG. 4(D), at time t44 summed C23+C24 is transferred from output buffer 141 to output sensing node 145, thereby generating a corresponding output signal OUT1 corresponding to summed charge C(23+24).

According to another aspect of the multi-sampling process, ADC 150-1 is controlled to generate multiple digital output data values during the given time period based on the same summed charge stored in output sensing node 145 (i.e., such that a first corresponding digital output data is generated during a first portion of the given time period, and a second corresponding digital output value is generated during a second portion of the given time period). Referring to FIG. 4(D), summed charge C23+C24 is stored output sensing node 145 for a given time period, and analog output signal OUT1 has a value O(23+24) corresponding to the summed charge C23+C24 during this time period. During a first portion of this time period, ADC 150-1 is controlled by way of clock signal CLK5 such that output signal OUT1 is stored or converted as set forth above, whereby a digital output value D11 is generated that is stored in memory location 162-2 of memory 162. During a subsequent second portion of this time period, ADC 150-1 is again controlled by way of clock signal CLK5 such that output signal OUT1 is again stored or converted to generate digital output value D12 that is stored in memory location 162-3 of memory 162. Note that the two digital image data values (i.e., D11 and D12) stored in memory 162 at the end of the given (first) time period were generated after the output buffer reset described above with reference to FIG. 4(C), and before a subsequent reset described below with reference to FIG. 4(E). Downstream digital signal processing may then be utilized, for example, to determine final digital image values by way of averaging the duplicate digital image data values. For example, CDS image data values D(S23) and D(S24) may be generated by way of subtracting initial value D10 from each of duplicated image values D11 and D12, and then calculating an average of the two adjusted values. In other embodiments, digital data values D11 and D12 may be averaged without adjustment, or processed using other methods known in the art.

Figure 4E:
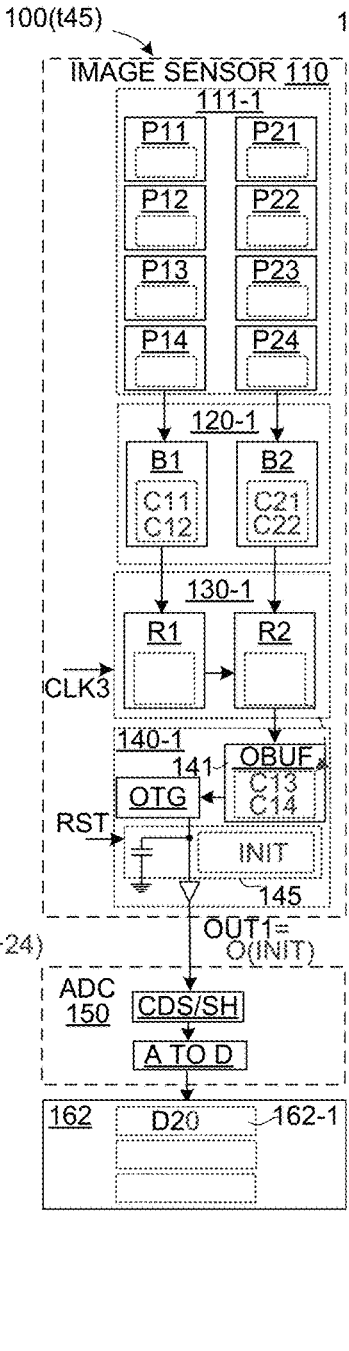
Figure 4F:
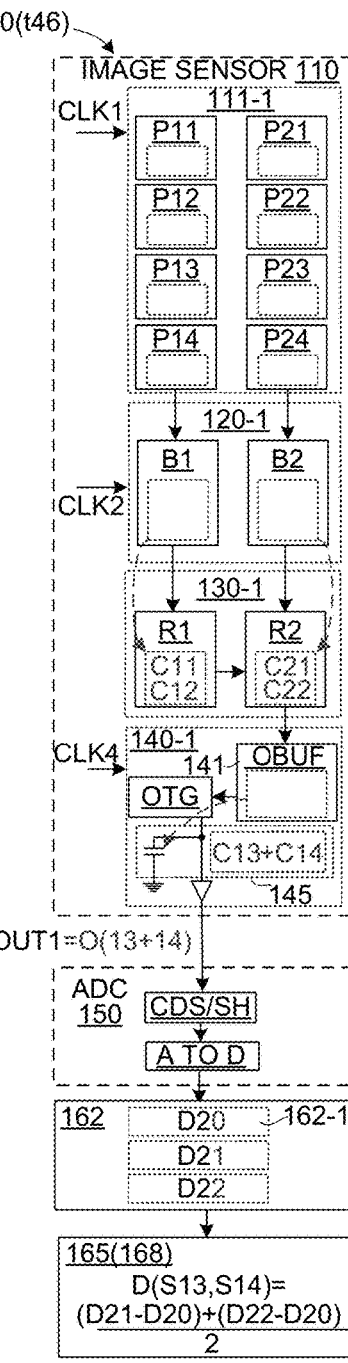

In the disclosed embodiment, referring to FIG. 4(E), output sensing node 145 is reset to the initial value after digital data values are generated for charges C23 and C24, and while shift register 130-1 is controlled by clock signal CLK3 to transfer summed charge C13+C14 into output buffer 141. Referring to FIG. 4(F), output circuit 140-1 is controlled by way of clock signal CLK4 to transfer combined charge C13+14 from output buffer 141 onto output sensing node 145, thereby generating analog output signal OUT1 having a value O(13+14) corresponding to the summed charge C13+C14. ADC 150-1 is then actuated by way of clock signal CLK5 (FIG. 1) in the manner described above to generate duplicate digital output values D21 and D22 during different portions of the time period during which summed charge C13+14 is stored on output sensing node 145, and then downstream digital signal processing is utilized, for example, to determine final digital image values D(S13) and D(S14) by way of averaging the duplicate digital image data values. Referring to the central portion of FIG. 4(F), during this time another vertical transfer, similar to that depicted in FIG. 4(B), is performed causing summed charges C11+C12 and C21+C22 to be transferred from charge storage cells B1 and B2 of pixel buffer 120-1 into shift register 130-1.

Although the above description of an exemplary embodiment of the multi-sampling process included binning the image data two rows at a time and digitizing each analog data value twice, these specific details were chosen to illustrate the principles and should not be interpreted as limiting the scope of the invention. For example, the multi-sampling process may be used without image binning if the vertical clock rate is low enough relative to the speed of the ADC. In another example, horizontal binning may be used instead of vertical binning by, for example, summing analog pixel data in output buffer 141. In another example, vertical and horizontal binning may be combined. In another example, the multi-sampling process may take multiple samples of both the reset value O(INIT) and of the image data values. The average of the multiple samples of the reset value may be computed and subtracted from the average of the image data values. In another example, three rows of image data or three horizontal pixels may be binned. More binning of the data allows more time for data readout, thus enabling the ADC to digitize more than twice each binned image data value.

Additional details regarding the present invention will now be provided with reference to various inspection systems and image sensor types that may be modified to implement the present invention, and to additional specific details regarding use of the present invention in practical settings.

Figure 5:
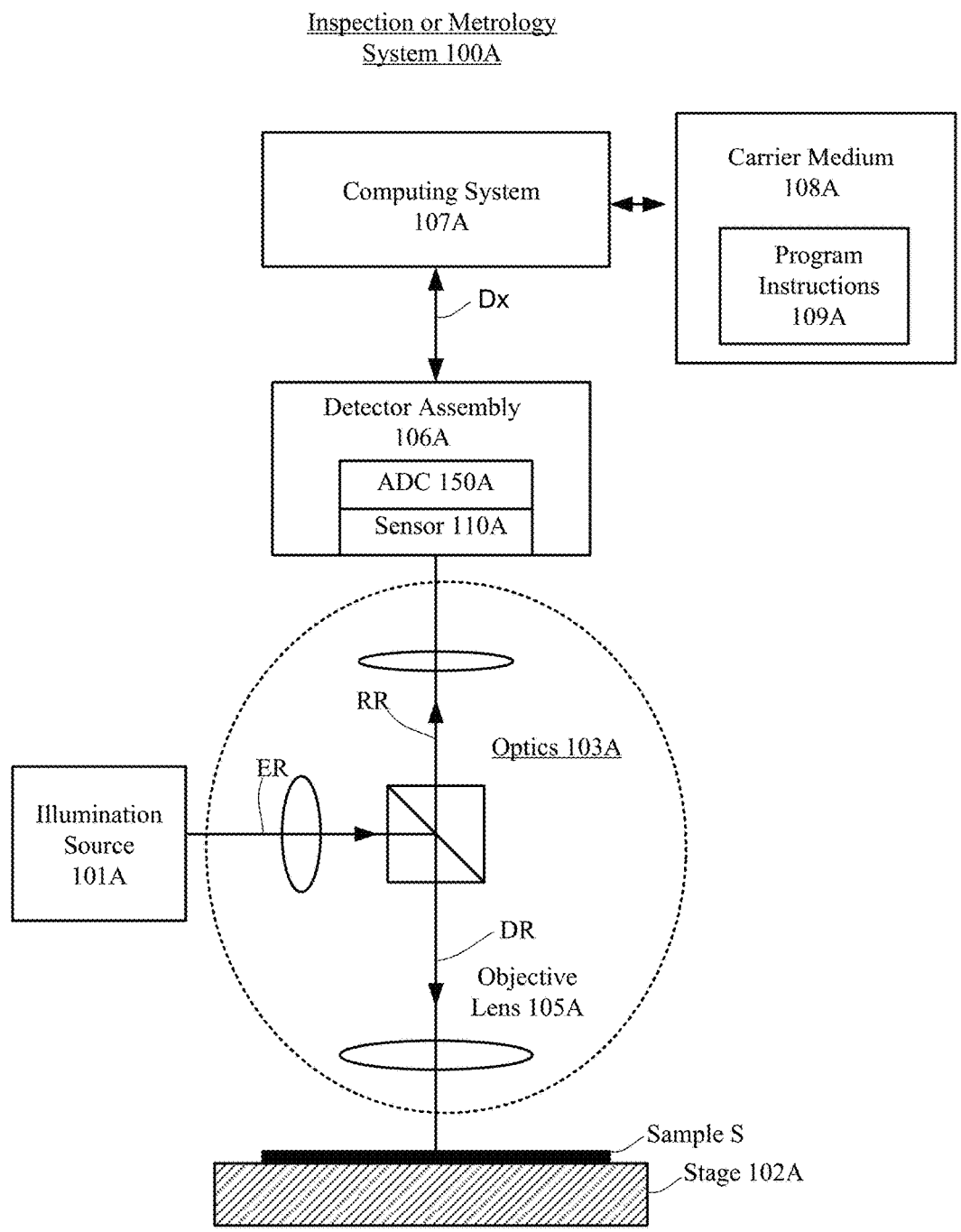
FIG. 5 illustrates an exemplary inspection system in accordance with an embodiment of the present invention.

FIG. 5 illustrates an exemplary inspection system 100A configured to inspect or measure a sample S such as a wafer, reticle, or photomask. Sample S is placed on a stage 102A to facilitate movement to different regions of sample S underneath optical system (optics) 103A. Stage 102A may comprise an X-Y stage or an R-θ stage. In some embodiments, stage 102A can adjust the height of sample S during inspection to maintain focus. In other embodiments, an objective lens 105A of optics 103A can be adjusted to maintain focus.

An illumination source 101A may comprise one or more lasers and/or a broad-band light source. Illumination source 101A may emit DUV and/or VUV radiation as emitted radiation ER. Optics 103A is configured to direct emitted radiation DR toward and focus directed radiation DR on sample S. Optics 103A may also comprise mirrors, lenses, and/or beam splitters configured using techniques known in the art. Portions of directed radiation DR that are reflected or scattered from sample S are collected, directed, and focused by optics 103A as redirected radiation RR onto an image sensor 110A, which is mounted within a detector assembly 106A.

Detector assembly 106A includes image sensor 110A and an ADC 150A that are configured and operated as described herein to implement at least one of the methods described herein for driving, controlling or reading out analog image data captured by image sensor 110A. Image sensor 110A may include a two-dimensional array sensor or a one-dimensional line sensor. In one embodiment, the digital image data values Dx output from image sensor 110A and ADC 150A are provided to a computing system 107A, which stores and processes digital image data values Dx in a manner consistent with the exemplary embodiments described herein. Computing system 107 is configured by program instructions 109A, which in one embodiment are stored on a carrier medium 108A.

In one embodiment, illumination source 101A may be a continuous source such as an arc lamp, a laser-pumped plasma light source, or a CW laser. In another embodiment, illumination source 101A may be a pulsed source such as a mode-locked laser, a Q-switched laser, or a plasma light source pumped by a Q-switched laser. In one embodiment of inspection system 100A incorporating a Q-switched laser, the image sensor 110A is synchronized with the laser pulses. In this embodiment, the image sensor may operate in a TDI mode during the laser pulse and then may read out the data through multiple outputs on both sides of the sensor in between laser pulses.

One embodiment of inspection system 100A illuminates a line on sample S, and collects scattered and/or reflected light in one or more dark-field and/or bright-field collection channels. In this embodiment, the image sensor 110A may include a line sensor or an electron-bombarded line sensor.

Another embodiment of inspection system 100A illuminates multiple spots on sample S, and collects scattered and/or reflected light in one or more dark-field and/or bright-field collection channels. In this embodiment, image sensor 110A may include a two-dimensional array sensor or an electron-bombarded two-dimensional array sensor.

Additional details of various embodiments of inspection system 100A can be found in U.S. Published Application 2016/0097727 by Vazhaeparambil et al., entitled "TDI Sensor in a Darkfield System", published on Apr. 7, 2016, U.S. Published Application 2013/0016346 entitled "WAFER INSPECTION SYSTEM", published on Jan. 17, 2013 by Romanovsky et al., U.S. Published Patent Application 2009/0180176, by Armstrong et al., which published on Jul. 16, 2009, U.S. Published Patent Application 2007/0002465 by Chuang et al., which published on Jan. 4, 2007, U.S. Pat. No. 8,891,079 entitled "Wafer inspection" by Zhao et al., U.S. Pat. No. 5,999,310, by Shafer et al., which issued on Dec. 7, 1999, and U.S. Pat. No. 7,525,649 by Leong et al., which issued on Apr. 28, 2009. All of these patents and patent applications are incorporated by reference herein.

Figure 6A:
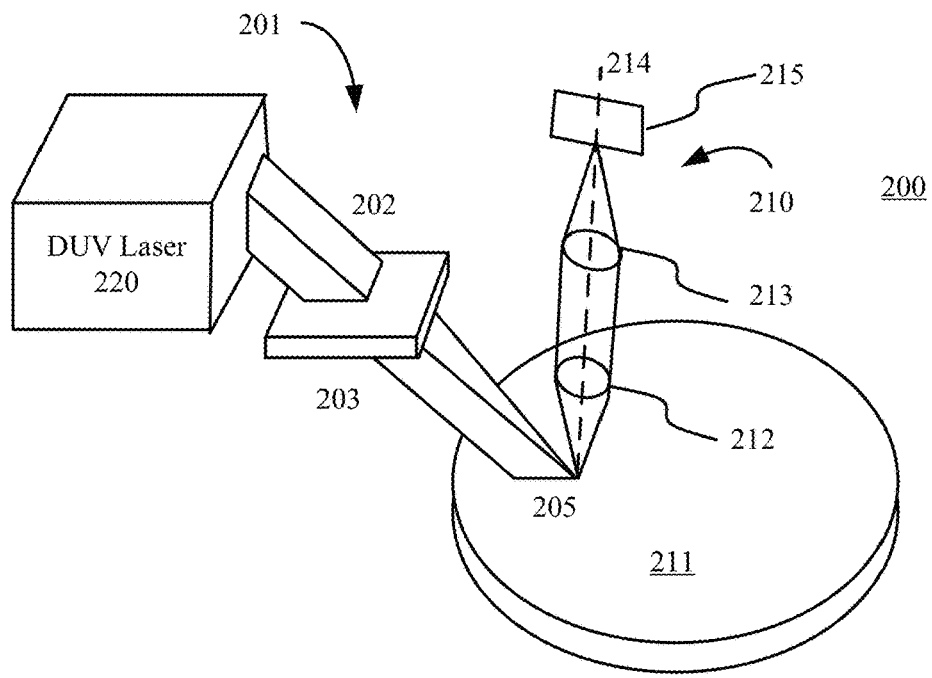
FIGS. 6A and 6B illustrate an exemplary inspection system with line illumination and one, or more, collection channels in accordance with another embodiment of the present invention.
Figure 6B:
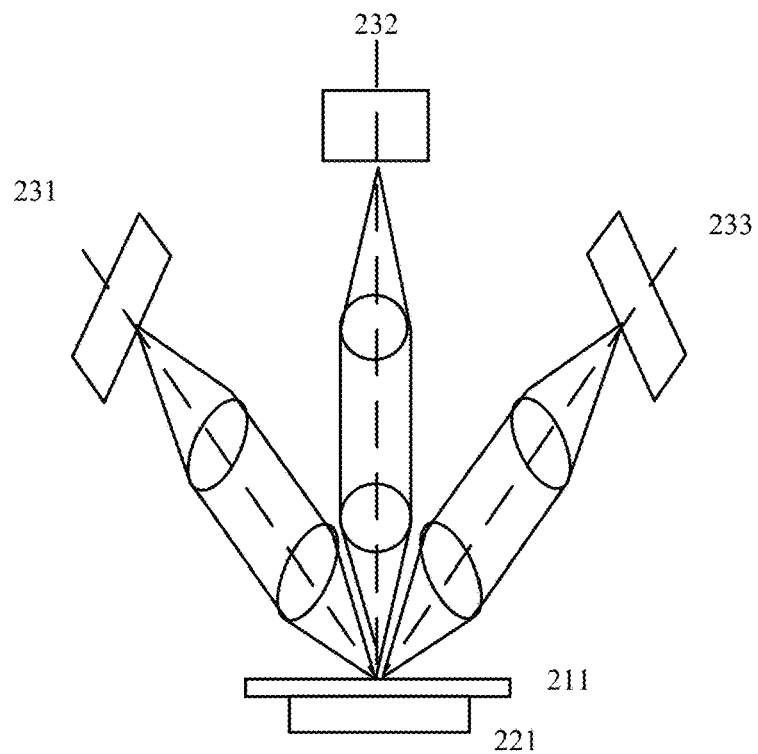

FIGS. 6(A) and 6(B) illustrate aspects of dark-field inspection systems that incorporate the circuits and/or methods described herein in accordance with other exemplary embodiments of the present invention. In FIG. 6(A), illumination optics 201 comprises a laser system 220 generating light 202 that is focused by a mirror or lens 203 into a line 205 on surface of a wafer or photomask (sample) 211 being inspected. Collection optics 210 directs light scattered from line 205 to a sensor 215 using lenses and/or mirrors 212 and 213. An optical axis 214 of collection optics 210 is not in the illumination plane of line 205. In some embodiments, optical axis 214 is approximately perpendicular to line 205. Sensor 215 comprises an array sensor, such as a linear array sensor. One, or more, of the circuits and/or methods described herein are used to drive, control or read out sensor 215.

FIG. 6(B) illustrates one embodiment of multiple dark-field collection systems 231, 232 and 233, each collection system substantially similar to collection optics 210 of FIG. 6(A). Collection systems 231, 232 and 233 may be used in combination with illumination optics substantially similar to illumination optics 201 of FIG. 6(A). Each collection system 231, 232 and 233 incorporates one, or more, of the circuits and/or methods described herein to drive, control or read out its sensor. Sample 211 is supported on stage 221, which moves the areas to be inspected underneath the optics. Stage 221 may comprise an X-Y stage or an R-θ stage, which preferably moves substantially continuously during the inspection to inspect large areas of the sample with minimal dead time.

More details of inspection systems in accordance with the embodiments illustrated in FIGS. 6(A) and 6(B) can be found in U.S. Pat. No. 7,525,649 to Leong et al., and U.S. Pat. No. 6,608,676 to Zhao et al., both of which are incorporated by reference herein.

Figure 7:
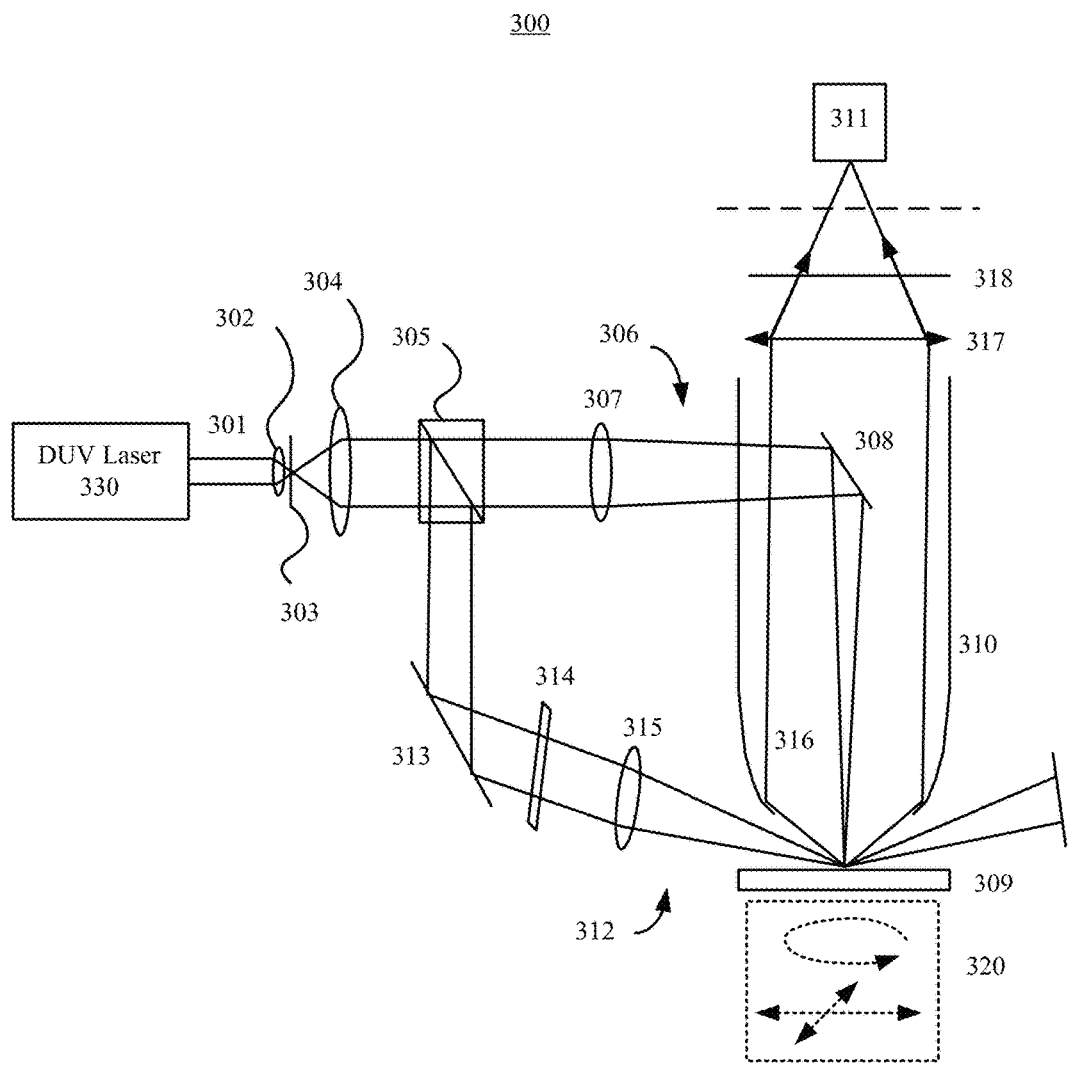
FIG. 7 illustrates an exemplary inspection system with normal and oblique illumination in accordance with yet another embodiment of the present invention.

FIG. 7 illustrates an inspection system 300 configured to detect particles or defects on a sample using both normal and oblique illumination beams. In this configuration, a laser system 330 provides a laser beam 301. A lens 302 focuses beam 301 through a spatial filter 303. Lens 304 collimates the beam and conveys it to a polarizing beam splitter 305. Beam splitter 305 passes a first polarized component to the normal illumination channel and a second polarized component to the oblique illumination channel, where the first and second components are orthogonal. In a normal illumination channel 306, the first polarized component is focused by optics 307 and reflected by a mirror 308 towards a surface of a sample 309. The radiation scattered by sample 309 (such as a wafer or photomask) is collected and focused by a paraboloidal mirror 310 to a sensor 311.

In an oblique illumination channel 312, the second polarized component is reflected by a beam splitter 305 to a mirror 313 which reflects such beam through a half-wave plate 314 and focused by optics 315 to sample 309. Radiation originating from the oblique illumination beam in oblique channel 312 and scattered by sample 309 is collected by paraboloidal mirror 310 and focused to sensor 311. Sensor 311 and the illuminated area (from the normal and oblique illumination channels on sample 309) are preferably at the foci of paraboloidal mirror 310.

Paraboloidal mirror 310 collimates the scattered radiation from sample 309 into a collimated beam 316. Collimated beam 316 is then focused by an objective 317 and through an analyzer 318 to sensor 311. Note that curved mirrored surfaces having shapes other than paraboloidal shapes may also be used. An instrument 320 can provide relative motion between the beams and sample 309 so that spots are scanned across the surface of sample 309. One or more of the circuits and methods described herein are used to drive, control or read out sensor 311. U.S. Pat. No. 6,201,601, which issued on Mar. 13, 2001 and is incorporated by reference herein, describes inspection system 300 in further detail.

Figure 8:
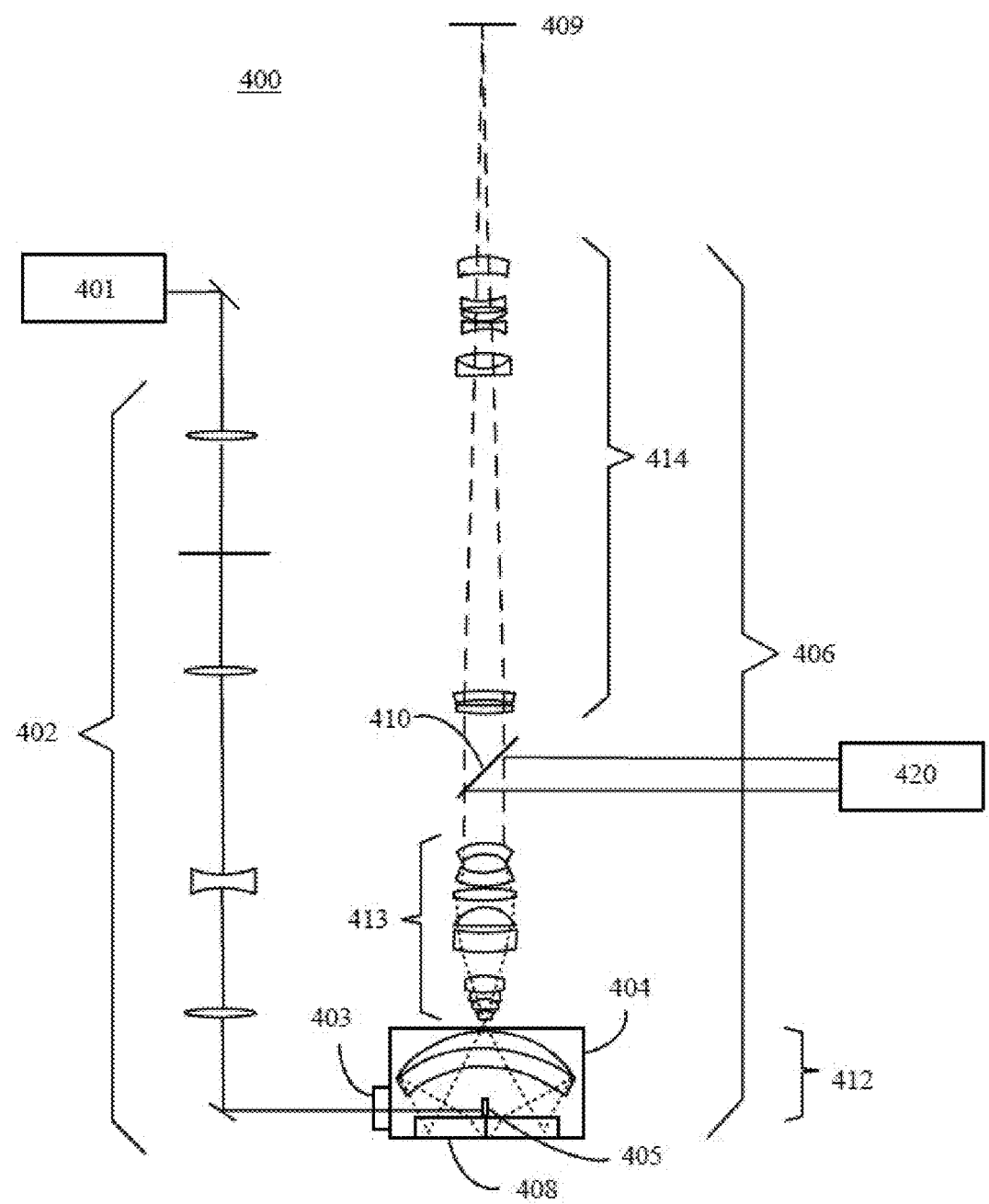
FIG. 8 illustrates an exemplary inspection system with bright-field and dark-field illumination channels in accordance with a further embodiment of the present invention.

FIG. 8 illustrates an exemplary catadioptric imaging system 400 configured as an inspection system with bright-field and dark-field inspection modes. System 400 may incorporate two illuminations sources: a laser 401, and a broad-band light illumination module 420.

In a dark-field mode, adaptation optics 402 control the laser illumination beam size and profile on the surface being inspected. A mechanical housing 404 includes an aperture and window 403, and a prism 405 to redirect the laser along the optical axis at normal incidence to the surface of a sample 408. A prism 405 also directs the specular reflection from surface features of sample 408 out of objective 406. Objective 406 collects light scattered by sample 408 and focuses it on a sensor 409. Lenses for objective 406 can be provided in the general form of a catadioptric objective 412, a focusing lens group 413, and a tube lens section 414, which may, optionally, include a zoom capability. Laser 401 may be a high-repetition-rate pulsed laser, such as a mode locked laser, or a CW laser.

In a bright-field mode, a broad-band illumination module 420 directs broad-band light to a beam splitter 410, which reflects that light towards focusing lens group 413 and catadioptric objective 412. Catadioptric objective 412 illuminates sample 408 with the broadband light. Light that is reflected or scattered from the sample is collected by objective 406 and focused on sensor 409. Broad-band illumination module 420 comprises, for example, a laser-pumped plasma light source or an arc lamp. Broad-band illumination module 420 may also include an auto-focus system to provide a signal to control the height of sample 408 relative to catadioptric objective 412.

One or more of the circuits and methods described herein are used to drive, control or read out sensor 409. System 400 is described in further detail in U.S. Pat. Nos. 7,345,825 and 7,817,260, which are incorporated by reference herein.

Figure 9A:
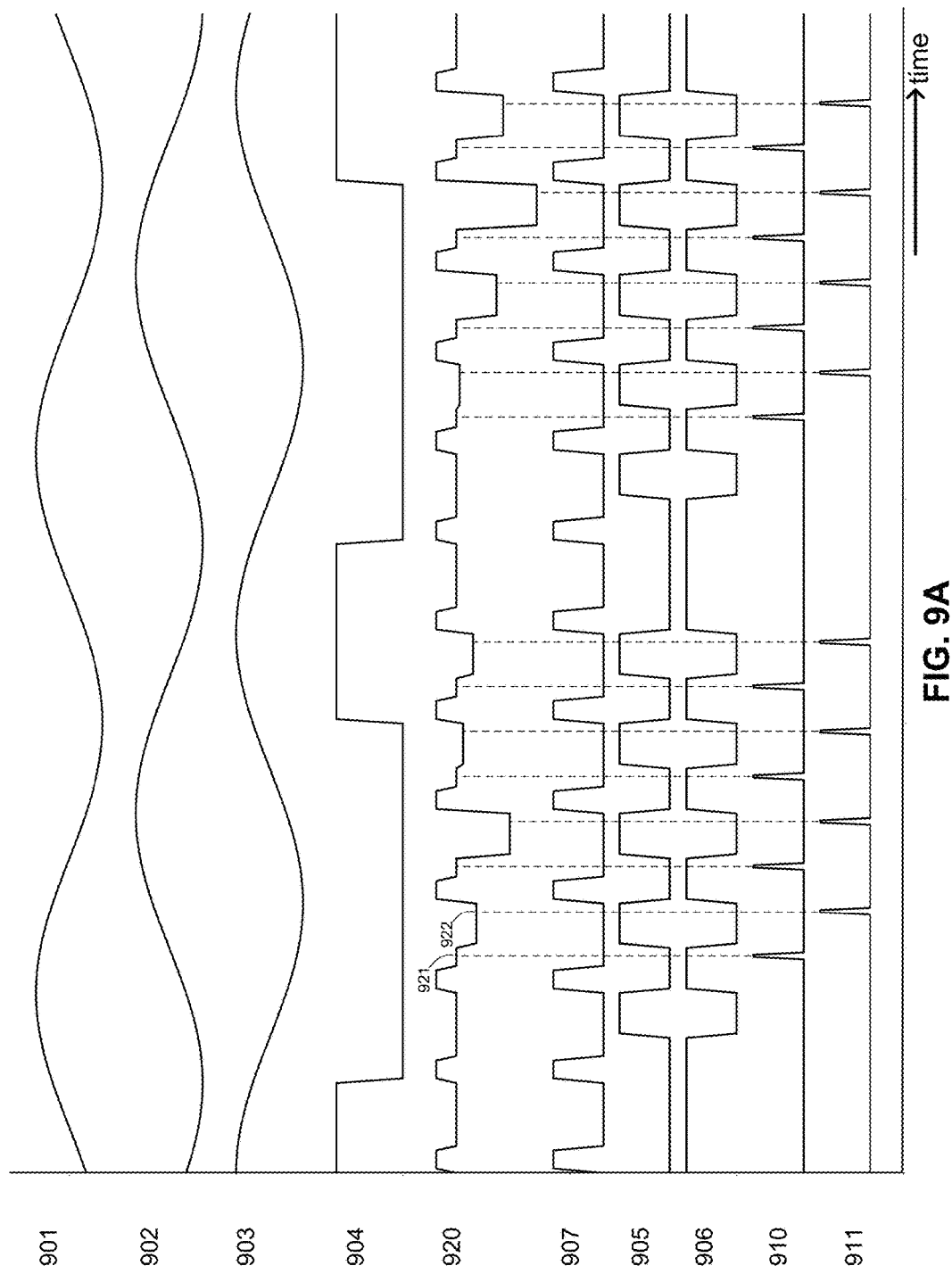
FIGS. 9A and 9B illustrate exemplary driving waveforms for the clock signals in the systems, circuits and methods described herein.

FIG. 9A illustrates exemplary waveforms in image capture and image data transfer operations using techniques similar to those depicted in FIGS. 2(A) to 2(G). Each waveform represents the voltage of a signal (such as a clock or output signal) as a function of time. The vertical axis represents voltage in arbitrary units and the horizontal axis represents time. The vertical scales of the different signals are not necessarily equal. The vertical offsets in the figure between the different signals are simply for clarity and do not imply that one voltage is more positive or more negative than another. Waveforms 901, 902 and 903 represent the voltages of a three phase vertical clock as a function of time. Each clock waveform is substantially 120° shifted in phase with respect to the other clock waveforms. These vertical clocks can perform the function of CLK1 in FIG. 1 that causes the charge stored in one row of pixels to be transferred to the next row, and the last row to be transferred to the pixel buffer 120-1 in FIG. 1. Note that the vertical clock could be a two-phase, three-phase or four-phase clock depending on the design of the pixels of the image sensor. More details on the use of sinusoidal and other clock signals for driving CCD image sensors can be found in U.S. Pat. Nos. 7,952,633 and 7,607,309 cited above. Although the clock waveforms are depicted as sine waves, other waveforms such as trapezoidal or square waves may be used. Waveform 904 represents the voltage of the line clock as a function of time. This line clock can perform the function of CLK2 in FIG. 1 that causes the contents of pixel buffer 120-1 to be transferred to shift registers 130-1 (e.g., as shown in FIG. 2(C)). No vertical binning is performed, so once per cycle of the vertical clocks, the line clock of waveform 904 transfers the contents of the pixel buffer to the shift register.

Waveforms 905 and 906 represent the voltages of a two-phase horizontal clock as a function of time. The two clock waveforms are substantially 180° out of phase with respect to one another. Note that depending on the design of the shift register, a three-phase or four-phase clock could be used. The waveforms might be trapezoidal, as shown, or might use a sine wave or distorted sine wave. These horizontal clocks can perform the function of CLK3 in FIG. 1 that causes the charges stored in the shift register to be transferred to the right, and the last shift register to be transferred to the output buffer 141 (if present), as indicated in FIG. 2(D). In the example shown in FIG. 9A, the horizontal shift register comprises four registers, and the horizontal shift register is followed by an output buffer, so a total of five clock cycles are needed to transfer all the charges to the output. FIGS. 2(A)-2(G) depicted a horizontal shift register comprising only two registers in order to keep the figures simpler.

Waveform 907 represents the voltage of the reset clock as a function of time that can perform the function of RST in FIGS. 2(A) to 2(G). In this example, the reset clock runs all the time, even when no data is being read out. Though not necessarily required, this is convenient to prevent build-up of charge in the output sensing node when no data transfers are happening. Waveform 920 represents the voltage of the sensor output signal as function of time, e.g. OUT1 in FIG. 2(D). Note that, in order to simplify the figure, the glitches and instability on the output signal caused by clock transitions have been omitted. Each pixel is shown as having a different output voltage from the others. Waveform 910 represents a trigger clock waveform to the CDS hardware (152 in FIG. 1) to sample the reset signal level (i.e., the voltage O(INIT) corresponding to charge INIT stored on output sensing node 145 as shown, for example, in FIG. 2(D)). The vertical dotted lines connecting waveforms 910 and 920 indicate the actual reset signal levels sampled on output waveform 920 for each pixel; for example, the first trigger from waveform 910 samples reset signal level 921 on waveform 920 for the first pixel in the line (row). This is followed by a similar trigger and sample for each of the subsequent pixels in the line. This trigger can cause the reset signal level to be stored on a capacitor in the CDS circuit (see the Janesick reference cited above), or it can cause the analog-to-digital converter, i.e. 154 in FIG. 1, to sample and digitize the reset signal level. Waveform 911 represents a trigger clock waveform to the sample-and-hold (within 152 in FIG. 1) and analog-to-digital converter, i.e. 154 in FIG. 1, to sample and digitize the output signal. The vertical dotted lines connecting waveforms 911 and 920 indicate the actual signal levels sampled on output waveform 920 for each pixel; for example, the first trigger from waveform 911 samples the output signal level 922 on waveform 920 for the first pixel in the line. A similar trigger and samples are then issued for each of the subsequent pixels in the line. For each pixel, if the reset signal level is stored on a capacitor within the CDS circuit, then the reset level will be subtracted from the output signal before digitization. If the reset signal level and the output signal are digitized separately, then the subtraction can be performed by a processor as explained above.

Figure 9B:
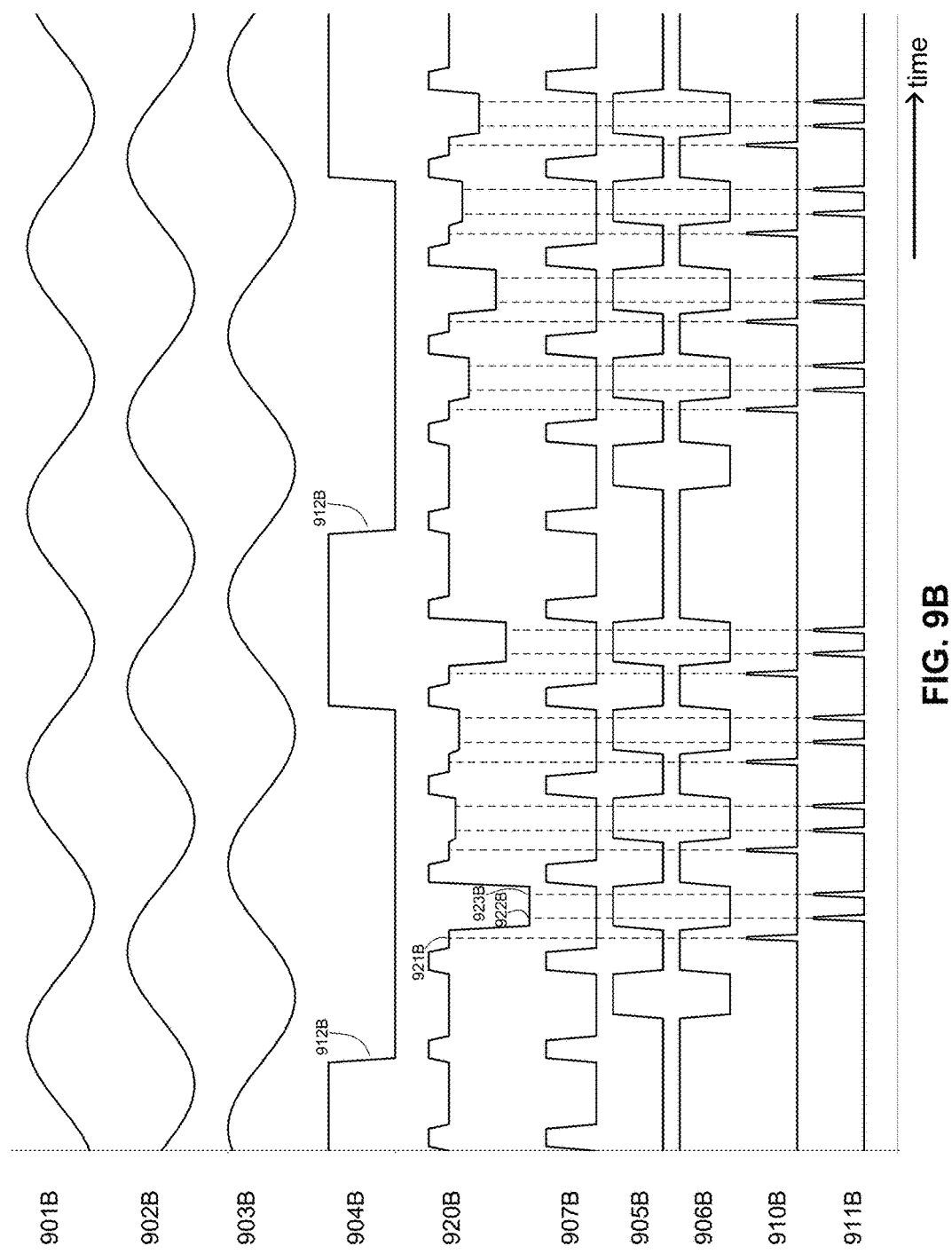

FIG. 9B illustrates exemplary waveforms in image capture and image data transfer operations using techniques similar to those depicted in FIGS. 4(A) to 4(F). Waveforms performing a substantially similar function in FIG. 9B as in FIG. 9A are labeled with the same number but with a letter B appended as a suffix. The waveforms will only be described only to the extent necessary to explain differences between FIGS. 9A and 9B. Details not explicitly described may be assumed to be substantially similar between the two figures.

Waveforms 901B, 902B and 903B represent the voltages of a three phase vertical clock as a function of time. As in FIG. 9A, each clock waveform is substantially 120° shifted in phase with respect to the other clock waveforms. These vertical clocks can perform the function of CLK1 in FIG. 4 that causes the charge stored in one row of pixels to be transferred to the next row, and the charge stored in the last row to be transferred to the pixel buffer 120-1 in FIG. 1. The concurrent charge transfer from one row of pixels to the next, and from the last row of pixels to pixel buffer 120-1 is depicted in FIG. 4(A). As noted above, the vertical clock could be a two-phase, three-phase or four-phase clock; other waveforms such as trapezoidal or square waves may be used. Waveform 904B represents the voltage of the line clock as a function of time. This line clock can perform the function of CLK2 in FIG. 4 that causes the contents of pixel buffer 120-1 to be transferred to shift registers 130-1 (e.g., as shown in FIG. 4(B)).

In one embodiment of the present invention, vertical binning of the pixel charges can be performed by timing line clock 904B so that the charge from two consecutive lines of pixels is transferred to and held under the pixel buffer 120-1. This is equivalent to summing the charges from two consecutive pixels in the same column under the pixel buffer, as depicted in FIG. 4(A). The contents of the pixel buffer is subsequently transferred to the horizontal registers 130-1 on the falling edge 912B of line clock 904B. This charge transfer from pixel buffer 120-1 to horizontal register 130-1 can be performed concurrently with the transfer of new signal charges from the last line (row) of pixels to the pixel buffer, as depicted in FIG. 4(B).

In the example of FIG. 9B describing the vertical binning of two pixels, the line clock is timed so as to have a period which is twice longer than the period of vertical clocks 901B, 902B and 903B; equivalently, the vertical clocks are timed at a frequency that is double the frequency of the line clock. In other embodiments of the present invention, the binning can be performed by summing under pixel buffer 130-1 the charges from more than two pixels, e.g. from three or more pixels, where for a given number of pixel signals being summed, the frequency of the vertical clock will be multiple of the line clock frequency by the same number.

Similarly to the description of FIG. 9A, waveforms 905B and 906B represent the voltages of a two-phase horizontal clock as a function of time. These clocks can perform the function of CLK3 in FIG. 4 that causes the charges stored in the shift register to be transferred first to the right across the register, e.g. from R1 to R2 in FIG. 4(C), and then to the output buffer 141, if present. In the example of FIG. 9B, the horizontal shift register comprises four registers followed by an output buffer, so a total of five clock cycles are needed to transfer all the charges to the output. FIGS. 4(A)-4(F) depicted a horizontal shift register comprising only two registers for simplicity.

Waveform 907B represents the voltage of the reset clock as a function of time. The reset clock can perform the function of RST in FIGS. 4(C) and 4(E). Waveform 920B represent the voltage of the sensor output signal as a function of time, i.e. OUT1 in FIGS. 4(C)-4(F), where in order to simplify the figure, glitches and instabilities caused on the output signal by clock transitions have been omitted. Each of the four pixels in each line is shown to have a different output voltage from the others. The signal in each pixel corresponds to the sum of two pixel signals from the same column (or to the sum of signals from more than two pixels, in the case of vertical binning spanning more than two pixels), where the summing has been performed under the output buffers 130-1 as described above.

Waveform 910B represents a trigger clock waveform to the CDS hardware (152 in FIG. 1) to sample the reset signal level, i.e. the voltage O(INIT) corresponding to charge INIT stored on the output sensing node, as shown for example in FIG. 4(C). The vertical dotted lines connecting waveforms 910B and 920B indicate the actual reset signal levels sampled on output waveform 920 for each pixel; for example, the first trigger from waveform 910B samples reset signal level 921B on waveform 920B for the first pixel in the line, which is followed by a similar trigger and sample for all the other pixels in the line. The trigger from waveform 910B can either cause the reset signal level to be stored on a capacitor in the CDS circuit, or can cause analog-to-digital converter 154 to sample and digitize the reset signal level. Waveform 911B represent a trigger clock waveform to the sample-and-hold circuitry (within 152 in FIG. 1) and analog-to-digital converter (154 in FIG. 1), to sample and digitize the output signal. Sampling and digitization occur at a time after the reset clock when the charges from the horizontal shift register and the output buffer (if present) are transferred to the sensing node by horizontal clocks 905B and 906B.

In the previous description of 9A, only one sample per pixel was triggered by waveform 911. The same sampling timing could be applied to the sensor output signal when vertical binning is performed. In another embodiment illustrated in FIG. 9B, the output signal is sampled twice per pixel by waveform 911B. The vertical dotted lines connecting waveforms 911B and 920B indicate the two actual output signal levels sampled on waveform 920B for each pixel; for example, the first trigger from waveform 911B samples output signal levels 922B and 923B for the first pixel in the line. Two similar triggers and samples are then issued for each of the remaining pixels in the line. With reference to FIGS. 4(D) and 4(F), this is equivalent to output signal OUT1 (corresponding to the sum of pixel charges C23 and C24 in FIG. 4(D), or C13 and C14 in FIG. 4(F)) being sampled twice before another reset is issued, e.g. in FIG. 4(E). If the reset signal level is stored on a capacitor within the CDS circuit, then the reset level will be subtracted from each of the two output signal samples per pixel before digitization. If the reset signal level and both output signal levels are digitized separately, then the subtraction can be performed by a signal processor. The signal processor can also perform the average between the results of the two separate CDS operations performed for each pixel, as illustrated for example in 165(168) in FIGS. 4(D) and 4(F)

The examples of FIGS. 4 and 9B illustrate the simple multi-sampling case in which for each pixel a single sample and digitization are performed for the reset signal level, and two samples and digitizations are performed for the output signal level. In other embodiments, the multi-sampling technique can be applied by having for each pixel more than one sample and digitization for the reset signal level, and two or more samples and digitization for the output signal levels.

Figure 10:
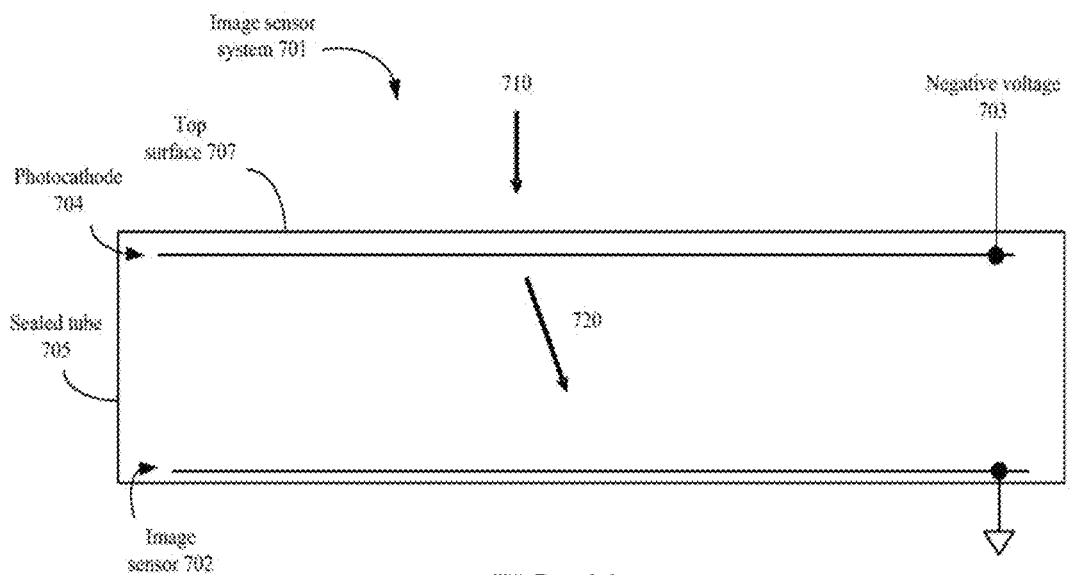
FIG. 10 illustrates an exemplary electron-bombarded image sensor in accordance with an embodiment of the invention described herein.

FIG. 10 illustrates an exemplary electron-bombarded image sensor system 701. In this embodiment, the whole assembly can be contained in a sealed tube 705 (e.g. substantially similar to the sealed tube of standard image intensifier and electron-bombarded CCD (EBCCD) devices). A top surface 707 of the tube 705 can include a window that is transparent at the wavelengths of interest. For UV sensitive electron-bombarded image sensors, this window preferably comprises a very pure grade of quartz, fused silica or alumina (sapphire). In some preferred embodiments, the outside surface of the window is coated with a UV anti-reflection coating. Such a coating might comprise a single layer of a low index material such as $MgF_2$, or might comprise a multi-layer coating.

Coated on the inside surface of the window, or placed immediately adjacent to that inside surface, is a photocathode 704. The photocathode material may be substantially similar to any photocathode material known in the art for use in photomultiplier, image intensifier, or prior-art EBCCD detectors. In preferred embodiments, the photocathode may comprise one or more alkali metals such as cesium, and/or may comprise a semiconductor such GaN, GaAs, or silicon. Photocathode 704 can be held at a negative voltage 703 relative to a solid-state image sensor 702, which is positioned near the bottom surface of sealed tube 705. In some embodiments, negative voltage 703 may be approximately 500 V; in other embodiments, it may be a few hundred volts or approximately 1000 V. In preferred embodiments, negative voltage 703 is between 100 V and 1500 V.

Solid-state image sensor 702 can be a thinned CCD or CMOS image sensor oriented so that the electrons impinge first on its back-side surface. The back-side of solid-state image sensor 702 includes a layer of boron deposited directly on the epitaxial layer of the image array as described in references cited herein. In some embodiments, a thin (few nm) layer of a conductive material, such as a refractory metal, is deposited on the boron layer to prevent charge-up of the sensor surface. A refractory metal such as titanium, tungsten, tantalum, rhodium, ruthenium, vanadium or chromium, has advantages compared with non-refractory metals because refractory metals' hardness makes them resistant to sputtering by the electrons, and they are relatively resistant to oxidation at room temperature. In some embodiments, solid-state image sensor 702 is a time-delay integration (TDI) CCD. In some embodiments, solid-state image sensor 702 comprises a linear array of electron-sensitive elements. In other embodiments, solid-state image sensor 702 comprises a two-dimensional array of electron sensitive elements. In some preferred embodiments, solid-state image sensor 702 is held close to ground potential (shown).

When light 710 is incident on electron-bombarded image sensor system 701, one or more photoelectrons 720 are emitted from photocathode 704. These photoelectrons are emitted in substantially all directions, but they are accelerated towards solid-state image sensor 702 by the potential difference between photocathode 704 and solid-state image sensor 702. In preferred embodiments, the gap between photocathode 704 and solid-state image sensor 702 is less than 1 mm. In some embodiments, the gap is approximately 500 µm.

Incorporating solid-state image sensor 702 having one of the structures described herein enables electron-bombarded image sensor system 701 to operate with a low potential difference between photocathode 704 and solid-state image sensor 702, and yet have high gain because electrons are more easily able to penetrate through the boron layer than through a silicon dioxide layer. Because boron-doped silicon, boron silicide, and boron are all at least partially conductive, charging of the surface under electron bombardment is minimized or avoided. The sensitivity to charge-up can be further reduced by a conductive or metallic layer on top of the boron layer as described herein.

In prior art EBCCD sensors, the gap between the photocathode and the image sensor is typically 1-2 mm. Such a large gap allows significant transverse motion of the electrons as they travel from the photocathode to the image sensor due to the energy of the electrons as they emerge from the photocathode. A gap of 1-2 mm or more is necessary because of the large potential difference between the photocathode and the image sensor (typically about 2000 V or more). Reducing the potential difference between the photocathode and the image sensor allows a smaller gap to be used. Furthermore, the lower energy of the electrons means that there is less spreading of the electrons created within the solid-state image sensor.

The low energy of the electrons arriving at solid-state image sensor 702 means that the probability of atoms being ablated from the surface of solid-state image sensor 702 is low to zero. Furthermore, the energy of the electrons arriving at solid state image sensor 702 is not enough to generate X-rays from the silicon, thereby avoiding the generation of spurious signal in nearby pixels of image sensor 702.

Collisions of low energy electrons with residual gas atoms in the vacuum created in sealed tube 705 will generate fewer ions as compared with high energy electrons. Furthermore, due to the low potential difference between photocathode 704 and solid-state image sensor 702, those ions will have less kinetic energy when they strike the photocathode and will ablate less photocathode material.

Additional details of electron-bombarded image sensors that can be incorporated into the electron-bombarded image sensor system 701 can be found in U.S. patent application Ser. No. 13/710,315, entitled "ELECTRON-BOMBARDED CHARGE-COUPLED DEVICE AND INSPECTION SYSTEMS USING EBCCD DETECTORS", filed by Chuang et al. on Dec. 10, 2012, and incorporated by reference herein. A photocathode structure suitable for use in electron-bombarded image sensor system 701 is described in U.S. patent application Ser. No. 13/947,975 entitled "PHOTOCATHODE INCLUDING SILICON SUBSTRATE WITH BORON LAYER", filed on Jul. 22, 2013 by Chuang et al., which claims priority to U.S. Provisional Patent Application 61/679,200, filed by Chuang et al. on Aug. 3, 2012. These applications are incorporated by reference herein.

Electron-bombarded image sensors are particularly suited for use with the circuits and methods described herein because electron-bombarded image sensors can operate with very low light levels, such as a few photons per pixel per integration period. Because of these low signal levels, the circuits and methods described herein are advantageous in detecting and preparing for digitization the low-level electrical signals resulting from such low light levels.

Figure 11:
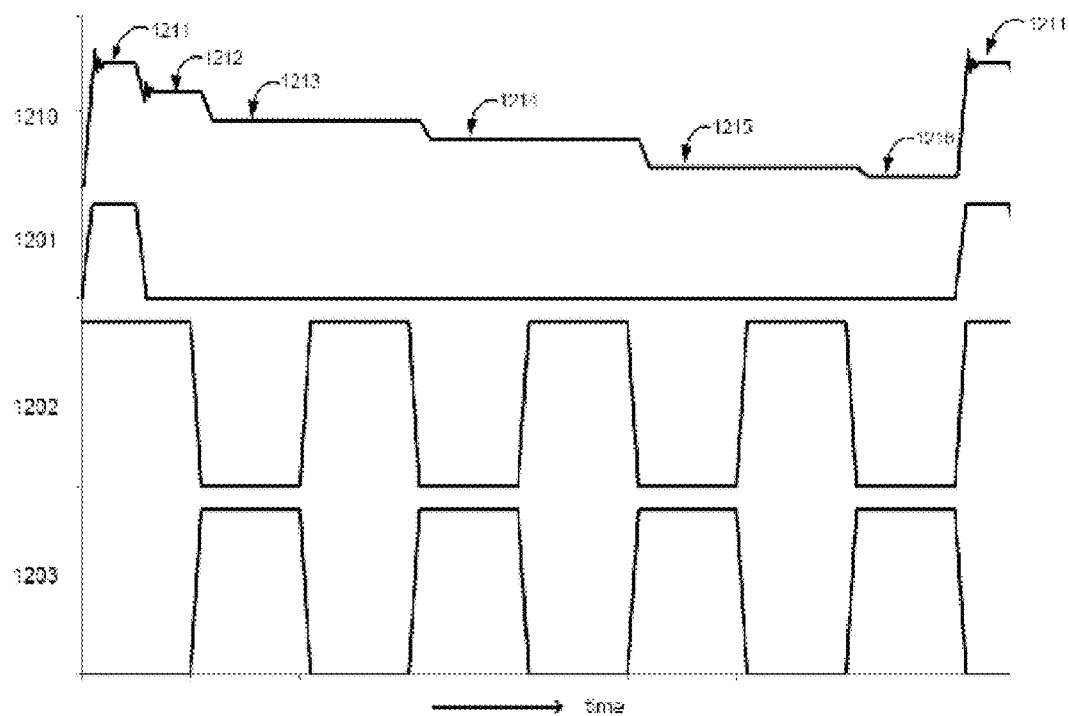
FIG. 11 illustrates an exemplary waveform in accordance with an embodiment of the invention described herein.

FIG. 11 illustrates exemplary waveforms in accordance with one embodiment of the present invention. 1201 represents the voltage of the reset clock as a function of time. 1202 and 1203 represent the voltage of the charge transfer clocks used to transfer the signal charge to the sensor output node, also called horizontal clocks as they typically drive a serial register (such as register 130-1 in FIG. 1) which transfers the charge in a direction which is perpendicular to the vertical charge transfer along the columns of pixels in the sensor imaging area. 1210 represents the voltage of the sensor output signal as a function of time. The vertical axis represents voltage in arbitrary units and the horizontal axis represents time. The vertical scales of the output signal voltage 1210, the reset clock 1201 and the horizontal clocks 1202 and 1203 are not necessarily equal. The vertical offsets in the figure between the output signal voltage 1210, the reset clock voltage 1201, and the horizontal clocks 1202 and 1203, are simply for clarity and do not imply that one voltage need be more positive or more negative than the other.

Figure 20:
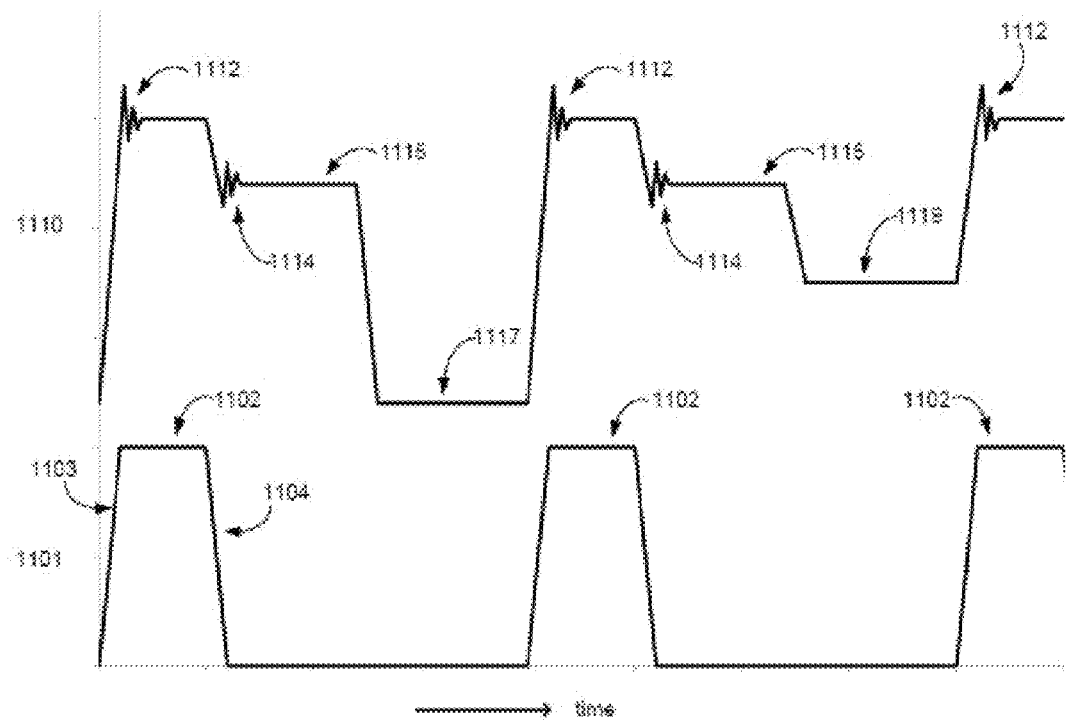
FIG. 20 illustrates typical reset clock and signal waveforms used with prior art inspection systems, sensors and electronics.

As explained in the description of prior art FIG. 20 above, the reset clock 1101 causes instability on the sensor output signal by having to be pulsed very fast and within a pixel time period. This causes problems for the sensor performance because of the noise introduced in the output signal voltage by the fast reset operation, which leaves very little time for the output signal to settle after the reset and after the charge from each pixel is transferred to the output sensing node.

In the embodiment of the present invention illustrated in FIG. 11, the reset pulse of reset clock 1201 is applied only at the beginning of a group of horizontal clock cycles, corresponding to multiple pixel readings. The horizontal clocks 1202 and 1203 clock the signal charge from each pixel onto the output sensing node, which is a small floating diffusion capacitance that collects the signal charge. The transfer of the pixel signal charges typically happens in two phases, as illustrated by the opposite phases of horizontal clocks 1202 and 1203. In the absence of a reset operation before each pixel transfer, and until the next reset occurs, each cycle of the horizontal clocks accumulates charge signals from consecutive pixels on the floating diffusion capacitance; this results in a decrease of the voltage at the sensor output which is proportional to the accumulated charge. 1210 is an exemplary output signal waveform resulting from this readout scheme. After the glitch 1211 in the waveform due to the reset pulse, the voltage settles at level 1212. The successive switching of horizontal clocks 1202 and 1203 transfers the charge from each pixel. 1212 represents the output signal level corresponding to the reset state of the floating diffusion capacitor, 1213 the signal level of the first pixel read out after reset, and similarly 1214, 1215, 1216 represent the output signal voltages of the second and subsequent pixels. At each transfer, the output signal voltage decreases by an amount which is proportional to the charge in the corresponding pixel. The amount of charge in each pixel can be reconstructed from the difference between the output signal voltage for the pixel itself and for the previous pixel. Thus, the charge in the first pixel can be reconstructed from the difference between voltages 1213 and 1212; the charge in the second pixel can be reconstructed from the difference between voltages 1214 and 1213, and so on for the following pixels, until another reset pulse is applied. Under this readout scheme, each pixel signal except for the first pixel after reset will thus be free of the interference introduced by the reset pulse, and will have more time to settle for efficient, low noise readout operation.

This readout mode is enabled by the physical properties of a typical image sensor output node (such as sensor output node 145 shown in FIG. 1), which features a small floating diffusion capacitance that holds the charge transferred onto it by the horizontal clocks. In typical operating conditions, physical effects such as leakage of charge carriers from the sensor substrate that can discharge the floating diffusion when charge is held onto it for long times (such as milliseconds or longer), are typically occurring with time constants that are much longer than the time needed to read out several pixel signals, especially at the high readout speeds used in modern inspection systems to enable high throughput. The number of pixel readouts that can be encompassed by a single reset in the present invention ranges from two pixels to as large a number of pixels as allowed by the sensor full well, that is the maximum charge signal that can be read out by the sensor, limited either by the charge capacity of the output sensing node, or by the dynamic range of the readout electronics chain, including signal processors for Correlated Double Sampling (CDS) and/or a digitizer. In one embodiment of a dark-field inspection with a low background noise level, an entire output tap of the sensor (typically 8 to 16 pixels) can be read out with a single reset.

Figure 12:
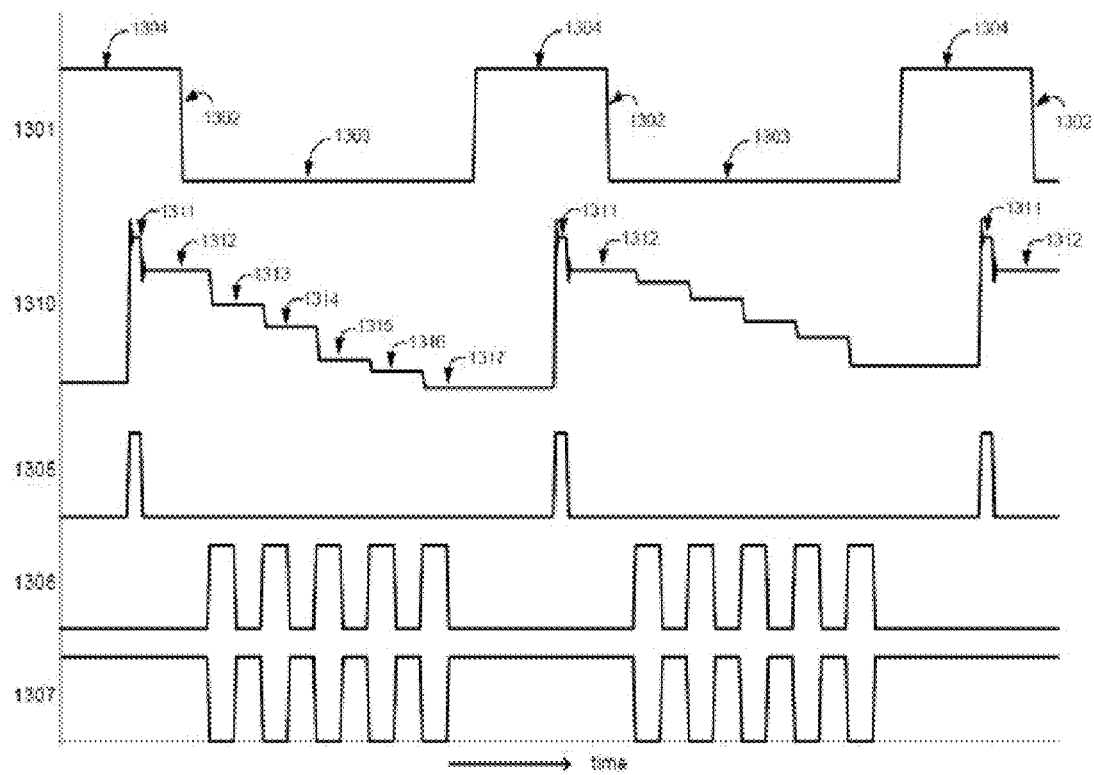
FIG. 12 illustrates exemplary clock waveforms used to read out an image sensor and the resulting sensor output signal waveform, in accordance with an embodiment of the invention described herein.

FIG. 12 illustrates another embodiment of the present invention. In a typical image sensor used in inspection systems, pixel data is transferred to the sensor output in groups of pixels that belong to a horizontal line of the imaging area, and are readout by the same output sensing node (or "tap"). In general, a physical line of pixels may be read out by multiple output sensing nodes or taps, each of them reading out a subset of pixels in the line. For simplicity, in the following we will use the expression "line of pixels" and its derivatives to indicate a group of pixels, belonging to the same physical line of the image sensor, that are read out by the same output sensing node. The number of pixels in said "line of pixels" need not be equal to the number of pixels in one physical line of the image sensor. 1301 is a clock waveform that controls the transfer of the pixel data from one pixel line to the sensor output, and will be hereby referred to as a line clock. The line clock can perform the same function as clock CLK2 in FIG. 1. 1305 is the voltage of the reset clock as a function of time, while 1306 and 1307 are the voltages of the horizontal clocks waveforms that transfer charge to the sensor output sensing node. 1310 is the resulting voltage of the sensor output signal. The vertical axis represents voltage in arbitrary units and the horizontal axis represents time. The vertical scales of the output signal voltage 1310, the line clock 1301, the reset clock 1305 and the horizontal clocks 1306 and 1307 are not necessarily equal. The vertical offsets in the figure between the output signal voltage 1310, the line clock 1301, the reset clock 1305 and the horizontal clocks 1306 and 1307, are simply for clarity and do not imply that one voltage is more positive or more negative than the other.

Line clock 1301 controls the transfer of the charge signals from the imaging pixels to the sensor output structure at a frequency which is synchronized with the movement of the object being inspected. Signal charges from a line of pixels are transferred to the sensor horizontal serial register on the falling edge 1302 of the line clock. Time interval 1303 is used by horizontal clocks 1306 and 1307 to sequentially transfer pixel signal charges from the horizontal serial register to the output sensing node. During time interval 1303, data from subsequent lines of pixels are prevented from being transferred to the horizontal serial register. After the signals for all the pixels of one line have been transferred to the output sensing node and read out, data for a subsequent line of pixels is transferred to the horizontal serial register on the next falling edge 1302 of the line clock. Before the signals from the next line of pixels are transferred, a time interval 1304 is typically allowed for the sensor output structure to fully complete the readout of the incumbent line, and for preparing the driving signals to read out the next line.

In the embodiment of the present invention illustrated in FIG. 12, the reset pulse 1305 is applied to the sensor output sensing node during time interval 1304, after the data from a line of pixels has been fully read out, and before the data from the next line of pixels are transferred to the horizontal serial register. The sensor output voltage 1310 will exhibit the typical glitch 1311 due to the reset pulse, which will cause instability to the signal and introduce noise. However, by anticipating the reset pulse well in advance of the falling edge 1302 of line clock 1301, which will transfer the data from the next line of pixels, the output voltage will have a relatively long time to settle to a stable level 1312, before the pixel data are clocked out. In typical operating conditions, the reset clock 1305 may be anticipated by a few ns to a few tens of ns before the transfer of charge from a line of pixels on the falling edge 1302 of line clock 1301. Subsequently, at each cycle of horizontal clocks 1306 and 1307, the signal charges from the pixels in the line are transferred to and accumulated on the floating diffusion capacitance at the sensor output sensing node. The signal in each pixel can be reconstructed by the difference between the voltage level corresponding to that pixel and the reference voltage level 1312, which as explained above will be fully settled after reset and thus more immune to interference from the reset operation. In the illustration in FIG. 12, the signal in the first pixel may be reconstructed from the difference between voltage level 1313 and the reference level 1312; the signal in the second pixel may be reconstructed from the difference between voltage level 1314 and the voltage level of the previous pixel 1313, and so on for all the following pixel voltages 1315, 1316 and 1317. The total charge accumulated on the sensor floating diffusion at the end of the readout of one line of pixels will be discharged by the next reset pulse, which will happen during the next wait time interval 1304 before the data from the next line of pixels is transferred to the horizontal serial register. The number of pixels that can be read out in this method between reset operations depends on the actual architecture of the image sensor (e.g. how many pixels per line are read out) and can be as long as allowed by the full well capacity of the output sensing node and/or by the dynamic range of the readout electronics chain.

Figure 13:
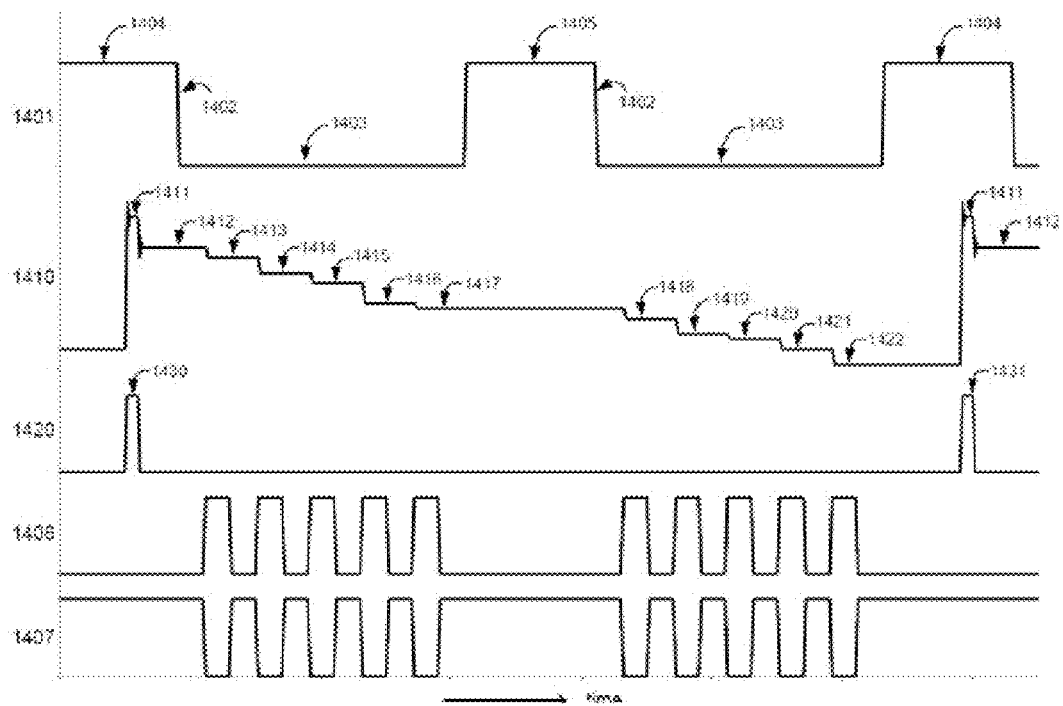
FIG. 13 illustrates exemplary clock waveforms used to read out an image sensor and the resulting sensor output signal waveform, in accordance with another embodiment of the invention described herein.

FIG. 13 illustrates another embodiment of the present invention. 1401 is the voltage of the line clock that controls the transfer of pixel data to the sensor horizontal serial register. 1420 is the voltage of the reset clock waveform, 1406 and 1407 are the voltages of the horizontal clocks. 1410 is the resulting voltage of the sensor output signal. The vertical axis represents voltage in arbitrary units and the horizontal axis represents time. The vertical scales of the output signal voltage 1410, the line clock 1401, the reset clock 1420 and the horizontal clocks 1406 and 1407 are not necessarily equal. The vertical offsets in the figure between the output signal voltage 1410, the line clock 1401, the reset clock 1420 and the horizontal clocks 1406 and 1407, are simply for clarity and do not imply that one voltage is more positive or more negative than the other.

In the embodiment of the present invention illustrated in FIG. 13, a first reset pulse 1430 is applied during time interval 1404, used to prepare the sensor output structure before the data from a first line of pixels is transferred to the horizontal serial register. After the reset glitch 1411, output signal voltage 1410 is allowed to settle to a stable level 1412 before the signal charges from a line of pixels are transferred to the horizontal serial register on the falling edge 1402 of line clock 1401. During line readout time 1403, horizontal clocks 1406 and 1407 subsequently clock the charge signals from the pixels in the incumbent line to the floating diffusion capacitance at the sensor output sensing node, where charge is accumulated until the next reset pulse is applied. At each horizontal clock cycle, output signal voltage 1410 settles at voltages 1413 for the first pixel after reset, 1414 for the second pixel, 1415 for the third pixel, 1416 and 1417 for the subsequent pixels in the first line. The signal for the first pixel may be reconstructed from the difference between voltage level 1413 and voltage level 1412, the signal for the second pixel may be reconstructed from the difference between voltage level 1414 and voltage level 1413, and so on the signals for the remaining pixels may be reconstructed from the difference between voltage levels 1415, 1416 and 1417, measured for each pixel at the time of pixel readout, and the voltage level for the previous pixel.

If the capacitance of the sensor floating diffusion is not saturated and full well has not been reached, a reset operation is not needed at the end of the first line of pixels. Another line of pixel data can be transferred to the sensor horizontal serial register without first resetting the output sensing node. The time interval 1405 during which the line clock prevents data from another line of pixels to be transferred to the horizontal serial register may be used to fully complete the readout of the first line of pixels and/or for other settling operations of the readout electronics, but may not necessarily include a reset pulse and may be made as short a practically achievable, thus improving the readout speed and consequently the throughput of the inspection system.

After the next falling edge 1402 of the line clock 1401 transfers the charge signals from the next line of pixels to the horizontal serial register, horizontal clocks 1406 and 1407 resume and clock the signal charges to the output floating diffusion, which accumulates the charge for each new pixel on top of the charge received from all the pixels in the previous line and the preceding pixels in the same line, if any. The signal for the first pixel in the second line may be reconstructed from the difference between voltage level 1418 and the voltage level 1417 corresponding to the last pixel of the previous line; the signal for the second pixel in the second line may be reconstructed from the difference between voltage level 1419, measured at the time the pixel is read out, and voltage level 1418 measured at the time the first pixel in the second line is read out; similarly, the signals for the remaining pixels in the second line may be reconstructed from the difference between voltage levels 1420, 1421 and 1422, measured at the time each pixel is read out, and the voltage level measured for the preceding pixels.

This methodology can continue for a number of successive pixel lines as high as allowed by the full well of the sensor output node and/or by the dynamic range of the readout electronics. After the pixel data for a number of desired lines has been transferred to the horizontal serial register and clocked to the output sensing node floating diffusion after the initial reset pulse 1430, a second reset pulse 1431 may be applied to the output sensing node and the transfer of data from another set of pixel lines to the sensor output may begin.

Horizontal clocks 1202 and 1203 in FIG. 11, horizontal clocks 1306 and 1307 in FIG. 12, and horizontal clock 1406 and 1407 in FIG. 13 are illustrated as square waves. In practice, the fast rising and falling edges of square clocks may cause glitches (not shown) in the image sensor output signal, introducing instability in the signal and possibly affecting noise performance. According to other embodiments of the present invention, the horizontal clocks may be driven by substantially sinusoidal voltages, as mentioned above in the description of FIGS. 9A and 9B. This minimizes the horizontal clocks ground return currents, and prevents glitches in the sensor output signal, thus improving the image sensor noise performance. In the case of a 2-phase horizontal register such as illustrated in FIGS. 11, 12 and 13, two driving sinusoidal clock voltages will have a phase delay of 180°. This phase value is the optimal phase difference between the two clock signals. In accordance with embodiments of the present invention, the clocks may be generated with relative phases that differ by a few degrees from the above value in order to compensate for different path lengths or impedances of conductors and connections between the drive electronics and the image sensor, such that the clock signals arrive at the active circuits of the image sensor with the desired relative phase relationship.

Figure 14:
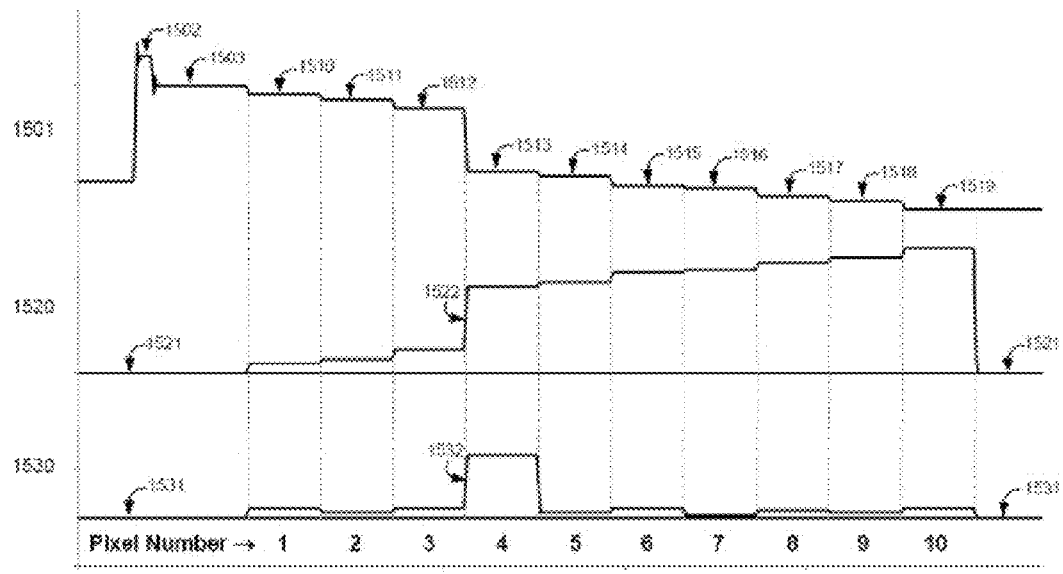
FIG. 14 illustrates an exemplary sensor output signal waveform and the corresponding pixel signals obtained by using two possible embodiments of the present invention.

FIG. 14 illustrates an embodiment of the present invention with two possible methodologies for measuring the pixel charge signals. 1501 is an exemplary output signal voltage waveform at the sensor output, for a readout time that encompasses a line of ten pixels. 1520 represents the pixel signals as reconstructed by the sensor readout chain using one of the methodologies described herein. 1530 represents the signals for the same pixels as reconstructed by the sensor readout chain using another methodology described herein. The vertical axis represents voltage in arbitrary units and the horizontal axis represents time. The vertical dotted lines illustrate the readout time for each pixel. For clarity, the pixel number as read out as a function of time is also indicated close to the horizontal axis. The vertical scales of the output signal voltage 1501 and of the pixel signals 1520 and 1530 are not necessarily equal. The vertical offsets in the figure between the output signal voltage 1501 and the pixel signals 1520 and 1530 are simply for clarity and do not imply that one voltage is more positive or more negative than the other. A single reset pulse is applied at the beginning of the line, which results in glitch 1502 on output signal waveform 1501. After a time interval 1503 during which the waveform voltage after reset is allowed to settle, the charge signals for each pixel in the line are successively accumulated on the floating diffusion capacitance at the sensor output sensing node. These signals appear as voltage levels 1510, 1511, 1512, 1513, 1514, 1515, 1516, 1517, 1518, and 1519 for the ten pixels in the line. A number of ten pixels in the line is here chosen simply for illustration purposes. According to embodiments of the present invention, an arbitrary number of pixels or lines of pixels, as large as practically allowed by the sensor full well or by the dynamic range of the readout electronics, may be used between reset operations with the methodologies described herein. In practical applications for very high speed sensors, each sensor output tap may typically have between about 2 to about 16 pixels.

In one embodiment of the present invention, the signal read out for each pixel will be equal to the amount of charge that has been accumulated on the sensor floating diffusion between the reset operation and the time at which the pixel is read out, as a result of successive charge transfers from the horizontal serial register. This continues until the following reset operation is performed. Each pixel is thus assigned a signal that equals the amount of charge collected by the same pixel, plus the charge accumulated on the floating diffusion during the previous pixel readings after reset. This methodology is illustrated by plot 1520. 1521 is the reference voltage which corresponds to zero signals, i.e. no charge is present in a pixel other than the very small charges that result from noise fluctuations. The signal for each pixel is determined by the difference between the voltage level measured on the output signal waveform 1501 at the readout time of the pixel itself, and the reference voltage level 1503 as measured on the output waveform after the reset operation. The signal for the first pixel will thus be equal to the difference between voltage level 1510 and the reference voltage 1503; the signal for the second pixel will be equal to the difference between voltage level 1511 and the reference voltage 1503, and correspond to the charge collected in the second pixel plus the charge collected in the first pixel; the signal for the third pixel will be equal to the difference between voltage 1512 and the reference voltage 1503, and correspond to the charge collected in the third pixel plus the charges collected in the first and in the second pixels; and so on for all the remaining pixels which are read out after reset and until another reset pulse is applied.

The methodology illustrated by plot 1520 may be beneficial for the detection of very small signals such as those originating for example from small background levels, e.g. the haze due to incoherent light scattering from the rough surface of a bare wafer being inspected. When most of the pixels contain small, quasi-constant signals, the noiseless integration of charge performed pixel by pixel at the sensor floating diffusion enables a more efficient detection of the background signals above the sensor noise floor. At each pixel readout after reset, the small signals keep accumulating and are more likely to be detectable than within a single pixel reading. At the same time, if a signal larger than background is present within the group of pixels being read out in between resets, for example originating from particles or scratches on the wafer, it can be resolved by abrupt variations in the signals of consecutive pixels. This is illustrated in the exemplary output signal waveform 1501 in FIG. 14, where all the pixels read out after reset except one contain a relatively small signal, and one pixel contains a relatively large signal, e.g. from a particle on the wafer being inspected. The presence of the background signals is enhanced by their being integrated pixel after pixel, for example in the first three pixels or in pixels five to ten, and after readout of a few pixels the total background signal is more easily detectable above the sensor noise floor. The particle signal can still be resolved by the signal variation 1522 measured in the fourth pixel.

In another embodiment of the present invention, the signal read out from each pixel is determined by applying a modified Correlated Double Sampling (CDS) technique. This methodology is illustrated by plot 1530, which applies the methodology to the exemplary output signal waveform 1501. 1531 is the reference voltage which corresponds to zero signals, i.e. no charge is present in a pixel other than the very small charges that result from noise fluctuations. The signal for the first pixel after reset (pixel one) is calculated as the difference between the voltage level 1510 measured at the readout time of the first pixel, and the reference voltage level 1503 measured after reset. For all the other pixels after the first one, the signal is calculated as the difference between the voltage level measured on the output signal waveform at the pixel readout time, and the voltage level measured for the previous pixel. The signal in the second pixel after reset will thus be determined by the difference between voltage level 1511 and voltage level 1510; the signal in the third pixel will be determined by the difference between voltage level 1512 and voltage level 1511; and so on for all the remaining pixels being read out after reset, and until another reset is applied. In the example of output signal waveform 1501 and plot 1530, the signal 1532 from a particle being detected on the fourth pixel is clearly resolved above the smaller background signals in all the other pixels.

The methodology illustrated by plot 1530 may be particularly suited for low noise imaging of wafers with large pixel to pixel variations or patterned wafers: the charge signals in each pixel are resolved individually, while retaining the benefits of Correlated Double Sampling for noise reduction, as the time interval between the two pixel samples is kept as short as a single pixel readout time.

Figure 15:
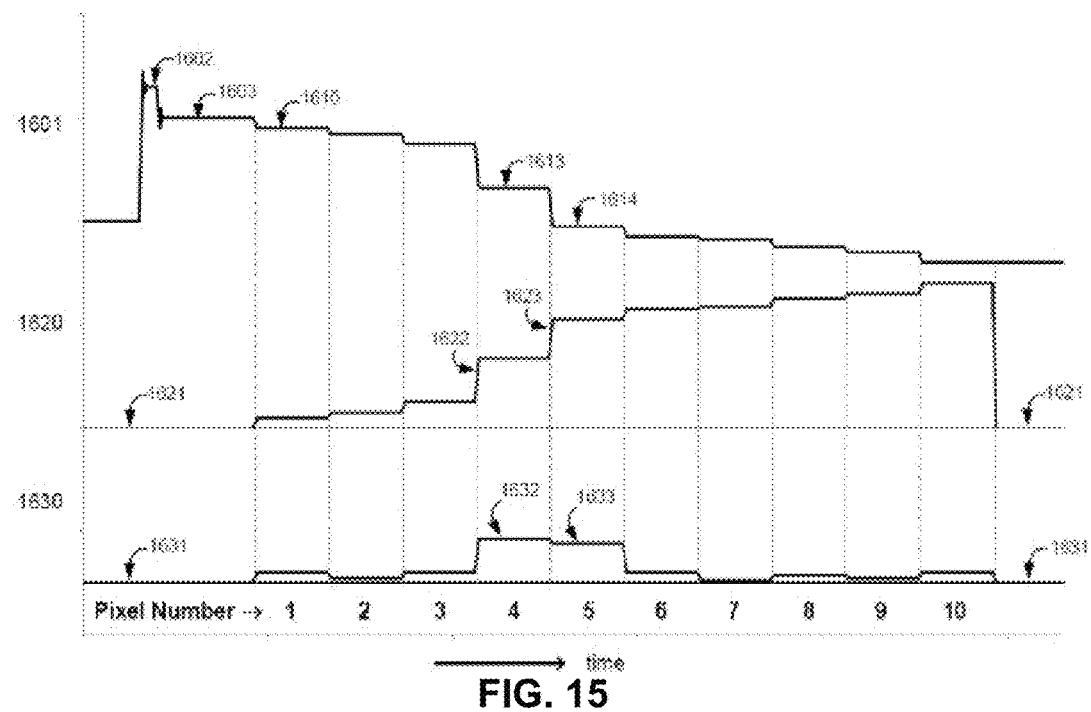
FIG. 15 illustrates an exemplary sensor output signal waveform and the resulting pixel signals, in accordance with an embodiment of the invention described herein.

FIG. 15 illustrates another embodiment of the present invention, in which the methodology described herein is used for the detection of signals from particles or other defects that are located between two image sensor pixels instead than on a single pixel. The vertical axis represents voltage in arbitrary units and the horizontal axis represents time. The vertical scales of output signal 1601 and of plots 1620 and 1630 are not necessarily equal, and the vertical offsets between them are simply for clarity and do not imply that one voltage is more positive or more negative than the other. Similarly to the description of FIG. 14 above, 1601 is an exemplary sensor output signal voltage waveform; after a reset clock at a time identifiable by the glitch 1602, the waveform settles at the reference voltage level 1603, and ten pixels are subsequently read out. 1620 plots the pixel signals as measured from the accumulation of the charge signals for consecutive pixels, where each pixel is assigned the sum of the signal collected by the pixel itself and the signals in all the previous pixels. 1630 plots the pixel signals as reconstructed by the modified Correlated Double Sampling methodology introduced in the description of FIG. 14, in which the signal for each pixel is determined from the difference between the voltage sampled at the time of readout of the pixel itself, and the voltage sampled for the previous pixels (or, in the case of the first pixel, from the difference between the voltage 1610 sampled for the first pixel and the reference voltage 1603 sampled after reset). 1621 and 1631 are the reference voltages for plots 1620 and 1630, respectively, which correspond to zero signals, i.e. no charge is present in a pixel other than the very small charges that result from noise fluctuations.

While most pixels contain small signals coming from either background illumination or noise fluctuations, the signal from a single particle or defect situated between two pixels (the fourth and the fifth pixel in this example) will appear as voltage variations larger than background that are sampled on both pixels, as voltages 1613 and 1614 on output signal waveform 1601, and will be reconstructed as signals 1622 and 1623 in the charge accumulation methodology illustrated by plot 1620, or as signals 1632 and 1633 in the modified Correlated Double Sampling methodology illustrated by plot 1630. The benefit of the charge accumulation methodology is evident when comparing signals 1622 and 1623 with signals 1632 and 1633: rather than detecting the smaller signals (1632 and 1633) resulting from the split of the total signal over the two pixels, accumulating the split signals over the two pixels (1622 and 1623) yields the same total signal and thus the same sensitivity as if the particle were located within a single pixel.

Figure 16:
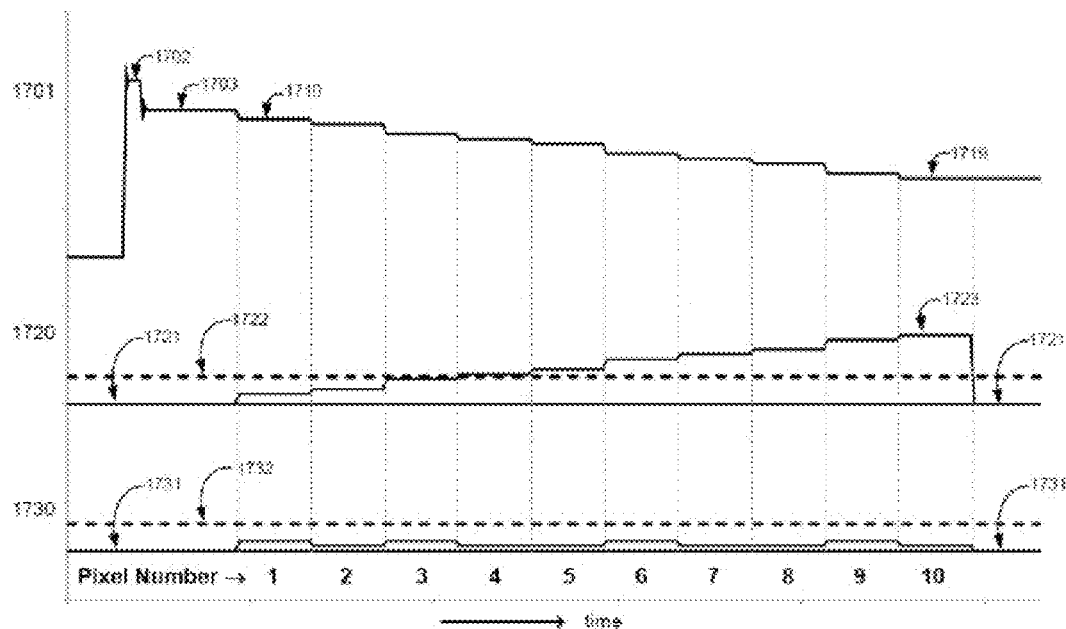
FIG. 16 illustrates an exemplary sensor output signal waveform and the resulting pixel signals, in accordance with another embodiment of the invention described herein.

FIG. 16 illustrates another embodiment of the present invention, in which the methodology described herein is used for the detection and measurement of small background signals whose amplitudes are smaller than or comparable with the readout noise level of an image sensor. The vertical axis represents voltage in arbitrary units and the horizontal axis represents time. The vertical scales of output signal 1701 and of plots 1720 and 1730 are not necessarily equal, and the vertical offsets between them are simply for clarity and do not imply that one voltage is more positive or more negative than the other. Similarly to the description of FIGS. 14 and 15 above, 1701 is an exemplary sensor output signal voltage waveform, corresponding to the readout of ten pixels after a single reset operation is performed; 1720 plots the pixel signals as measured from the accumulation of charge signals for consecutive pixels, as introduced in FIG. 14 above; 1730 plots the pixel signals as reconstructed by the modified Correlated Double Sampling methodology, also introduced in the description of FIG. 14, in which the signal for each pixel is determined by the difference between the voltage sampled at the time of readout of the pixel itself, and the voltage sampled for the previous pixel (or, in the case of the first pixel, from the difference between the voltage 1710 sampled for the first pixel and the reference voltage 1703 to which the waveform settles after the reset glitch 1702). 1721 and 1731 are the reference voltages for plots 1720 and 1730, respectively, which correspond to zero signals, i.e. no charge is present in a pixel other than the very small charges that result from noise fluctuations. 1722 and 1732 indicate the readout noise level for the signals reconstructed in plot 1720 and 1730, respectively, and referred to reference voltage levels 1721 and 1731, respectively. The two methodologies illustrated by plots 1720 and 1730 may introduce different readout noise levels, depending on the specific implementation of the readout electronics and its associated noise components.

The pixel signals measured by exemplary output signal waveform 1701 are all of comparable amplitude, which is lower than the readout noise level. In a wafer inspection system, this can occur when a uniform, low intensity background is present across the wafer image due for example to the haze generated by incoherent light scattering from the wafer surface roughness. In embodiments of the present invention, it is important to detect the presence of the background and measure its amplitude. In the example of FIG. 16, it is evident from plot 1730 that Correlated Double Sampling is not adequate to do so, as the pixel signals thus reconstructed will not be detectable above the noise floor 1732 of the readout electronics. However, plot 1720 shows that using charge accumulation can instead provide a detectable signal above the noise floor 1722, after the signals for a certain amount of pixels have been read out. Further, the charge accumulation methodology allows the measurement of the average intensity of the background signal, by sampling the total charge sum 1723 for all the pixels read out in between resets, and by dividing this value by the number of said pixels.

Figure 17:
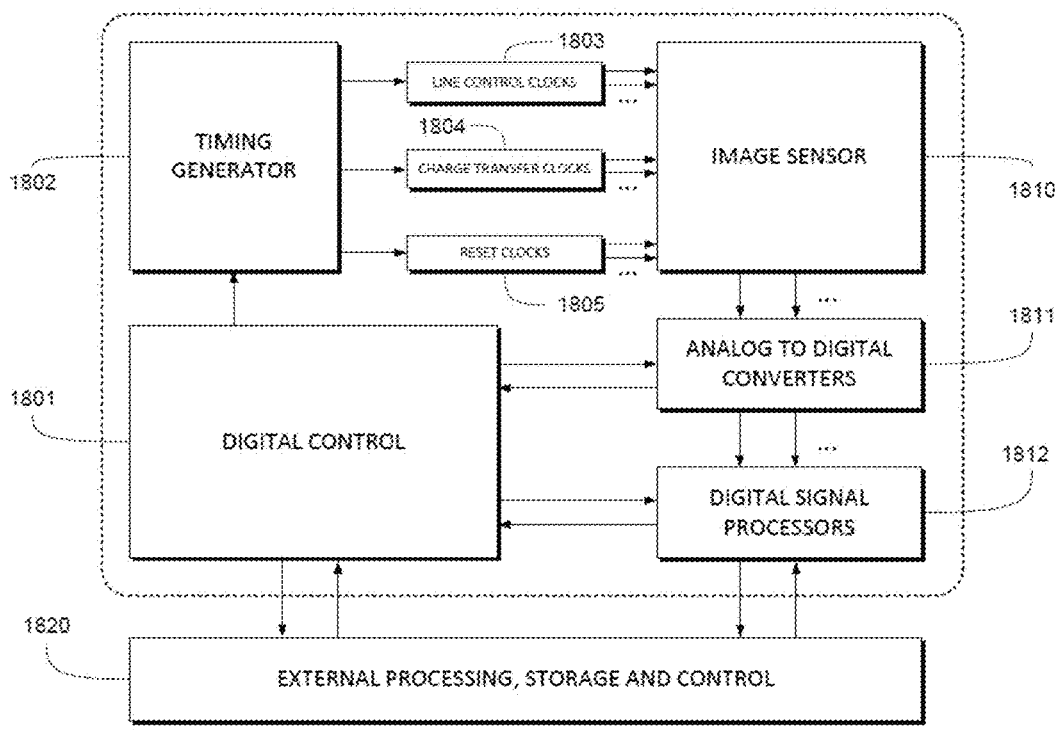
FIG. 17 illustrates an imaging apparatus in accordance with one embodiment of the present invention, comprising an image sensor, analog-to-digital conversion, digital signal processing, a digital control unit that controls the timing and the data acquisition for the whole apparatus, and an external unit for data processing, storage and control.

FIG. 17 illustrates one embodiment of an imaging apparatus implementing features and methodologies described in the present invention. The apparatus includes an Image Sensor 1810, whose output signal voltages are digitized by Analog-to-Digital Converters (ADCs) 1811. The digital image data at the output of the ADCs may be further processed by Digital Signal Processors (DSPs) 1812. A Digital Control section 1801 organizes the timing of the signals (clocks) needed to drive Image Sensor 1810 by controlling a Timing Generator (TG) section 1802 that generates said signals or clocks. Clock sections may comprise line control clocks 1803, charge transfer clocks 1804, and reset clocks 1805. Clock sections 1803, 1804 and 1805 may include circuits to buffer and amplify the digital signals received from the Timing Generator 1802, so as to drive Image Sensor 1810 using optimized voltages for the clock signals. Clock sections 1803, 1804 and 1805 may also include circuitries and methods to modulate the clock signals into waveforms of arbitrary shape and time relations between each other, so as to drive Image Sensor 1810 using optimized timing for the clock signals. Digital Control section 1801 also generates signals needed to control ADCs 1811 and DSPs 1812, determines the time relation between said signals and the clocks that drive Image Sensor 1810, and synchronizes the whole apparatus so as to acquire the digital image data read out by the ADCs and/or the digital image data processed by the DSPs.

Digital Signal Processors (DSPs) section 1812 receives digital image data from ADCs section 1811 and performs a plurality of operations on it, such as but not limited to: comparing said digital image data against a predetermined threshold, and enabling or disabling a data valid flag depending on the result of the comparison; determining the amplitude of background signals by quickly evaluating the sum of the signals accumulated for a plurality of pixels or a plurality of lines of pixels read out by the same output sensing node, using a methodology similar to the one illustrated in FIG. 16 above; determining the presence of signals of interest above background, such as signals coming from particles or defects on a wafer being inspected, and counting the number of these occurrences within a plurality of pixels or a plurality of lines of pixels, or within the entire image captured by the image sensor, using methodologies similar to those illustrated in FIGS. 14 and 15 above; generating and controlling feedback signals to Digital Control section 1801 that provide the possibility to dynamically change and adapt the timing control of Image Sensor 1810 and its readout, comprising ADCs 1811 and DSPs 1812, depending on the results of one or more of the functions and evaluations described above, or of other functions and evaluations performed by the DSPs 1812 not described herein.

In one example, in cases in which most of the pixels contain small background signals, and a limited occurrence of signals of interest is expected within a certain number of pixels, DSPs 1812 may instruct Digital Control section 1801 to modify the timing of the clocks driving Image Sensor 1810 so as to read out a larger number of pixels in between resets, in a manner similar to the one illustrated in FIG. 12 above, and so as to optimize the use of the charge accumulation methodology described in the present invention. In another example, and also depending on the amplitude or other features of the signals being detected, DSPs 1812 may instruct Digital Control section 1801 to modify the timing of the imaging apparatus so as to read a plurality of lines of pixels in between resets, in manners similar to those illustrated in FIGS. 13 and 14 above.

The imaging apparatus illustrated in FIG. 17 further includes a section 1820 for External Processing, Storage and Control. Section 1820 receives and stores digital image data and other signals from DSPs 1812 and/or Digital Control section 1801, such as but not limited to signals that identify the nature and format of the data, or signals that determine if the data is valid or not and is therefore to be permanently stored or not. Section 1820 may also implement software that provides user interfaces to control the operation of the imaging apparatus, and manages other functions such as retrieval and processing of image data.

Implementations of the imaging apparatus described in FIG. 17 may take varying forms. In preferred embodiments, the Digital Control and Timing Generator functions are performed within a Field Programmable Gate Array (FPGA) device, while the ADCs and the DSPs may be implemented by one or more Application Specific Integrated Circuits (ASICs).

Figure 18:
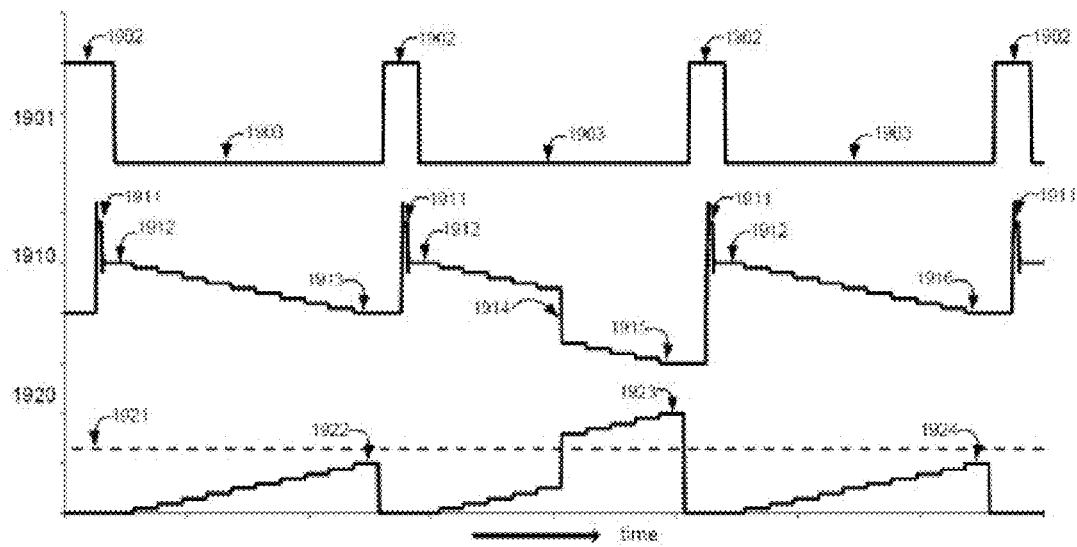
FIG. 18 illustrates an exemplary clock signal, an exemplary sensor output signal waveform and the resulting pixel signals, in accordance with embodiments of the present invention.

FIG. 18 illustrates another embodiment of the present invention. This embodiment can be implemented in an imaging apparatus similar to the one described in FIG. 17 above, comprising an image sensor, its driving signals, and Digital Signal Processors (DSPs) that evaluate the pixel data sampled by Analog-to-Digital Converters (ADCs). 1901 is a clock signal that controls the transfer of pixel data to the sensor output structure, in a manner similar to the line clock described in FIGS. 12 and 13 above. 1910 is an exemplary output signal voltage waveform of the image sensor. 1920 plots the pixel signals as measured from output signal 1910 according to the charge accumulation methodology introduced in FIG. 14. The vertical axis represents voltage in arbitrary units and the horizontal axis represents time. The vertical scales of line clock 1901, of output signal 1910 and of plot 1920 are not necessarily equal, and the vertical offsets between them are simply for clarity and do not imply that one voltage is more positive or more negative than the other.

Similarly to the descriptions of FIGS. 12 and 13 above, during time interval 1902 charge signals from the image sensor pixels are prevented from being transferred to the sensor horizontal serial register; during this time, the floating diffusion at the output sensing node is reset, causing glitch 1911 in output signal 1910, which then settles at voltage level 1912. During time intervals 1903, pixel data is transferred to the sensor horizontal serial register, and charge signals read out from consecutive pixels in a line are clocked to the sensor output (the horizontal clocks not being shown in FIG. 18 for simplicity) and are accumulated on the floating diffusion. After readout of one line is completed, the floating diffusion is reset again and charge signals from the following line of pixels are transferred to the sensor horizontal serial register, and subsequently clocked to the output sensing node. Exemplary output signal 1910 corresponds to the readout of three lines of ten pixels each. In this example, all pixels in the first and in the third line contain small noise or background signals; in the second line, a relatively large voltage variation 1914 is sampled for the sixth pixel, and corresponds to a particle or a defect on the wafer being inspected. Output signal 1910 settles at voltage 1913 at the end of the first line, at voltage 1915 at the end of the second line, and at voltage 1916 at the end of the third line.

The accumulated pixel signals, reconstructed from the difference between the voltage sampled for each pixel and the reference voltage level 1912, are illustrated in plot 1920. In embodiments of the present invention, the pixel signals thus measured are compared by DSPs against a predetermined voltage threshold 1921, aimed at resolving pixel data with signals of interest from pixel data with background signals. In one embodiment of the present invention, the DSPs first evaluate the total signal at the end of each line as measured from voltages 1922, 1923 and 1924 for the three lines, respectively, against threshold 1921. If the total signal for a line is below the threshold, the DSPs will transfer to the output of the imaging apparatus only the signal for the last pixel, containing the sum of all the pixel signals in the line, so that the background signal can be measured, in a manner similar to the one illustrated in FIG. 16. If the total signal for a line is instead above threshold 1921, pixel data for that line is flagged as valid and sent to the output of the imaging apparatus in its entirety, so that signals of interest within the line can be resolved by further processing. In the example of FIG. 18, the first and the third line contain only background signals, and only signals 1922 and 1924 for the last pixels of these two lines will be sent to the output of the imaging apparatus. However, the total signal 1923 for the second line of pixels is above threshold 1921 due to the presence of a large signal on the sixth pixel, and data for all the pixels in the line will be sent to the output of the imaging apparatus.

In another embodiment of the present invention, DSPs send pixel data to the output of the imaging apparatus only for pixel lines whose total signal is above a predetermined threshold (e.g. the second line of the example in FIG. 18), and do not send any pixel data to the output of the imaging apparatus if the total signal in a line of pixels is below the threshold, so as to exclude background signals in their entirety from further processing or storage.

The methodologies illustrated above can be effective in improving the speed of the data processing and consequently the throughput of a wafer inspection system. The comparison with a predetermined threshold can be performed very quickly by the DSPs as only the total signal for a line of pixels is evaluated at first. Furthermore, only pixels or lines of pixels with relevant data may be preserved for further processing or storage, thus decreasing the amount of data that needs to be transferred to the output of the imaging apparatus and further contributing to increase the speed of wafer inspection.

Transmitting the total signal for a line of pixels and/or pixel data for that line only when the total signal or an individual pixel exceeds a threshold is particularly useful for the inspection of unpatterned wafers, such as wafers with a native oxide film or deposited film on their surface. Unpatterned wafers typically have few particles or defects on their surface, so transmitting only pixels or lines of pixels that exceed a threshold can reduce the quantity of data that needs to be transmitted by an order of magnitude or more. The haze signal that provides information about the surface condition or roughness is often also of interest. The haze signal is typically a weak signal because the surface of unpatterned wafers is usually very smooth (such as roughness less than about 1 nm). The total line signal provides information about haze with better signal-to-noise ratio than the individual pixel signals. Transmitting only the total line signal, or transmitting the total line signal and only individual pixels where a threshold is exceeded, can reduce the amount of data that needs to be transmitted by a large factor (a factor that is almost equal to the number of pixels in a line if the defect density is low).

Figure 19:
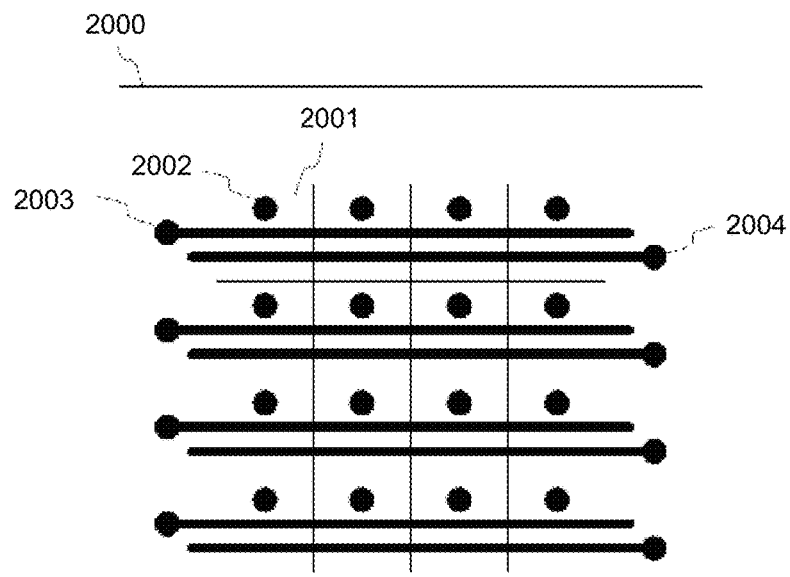
FIG. 19 illustrates an exemplary image sensor comprising multiple pixels with one output per pixel in accordance with an embodiment of the invention described herein.

FIG. 19 illustrates key features of an exemplary image sensor comprising multiple pixels in accordance with an embodiment of the invention described herein. Image sensor 2000 comprises an array of pixels 2001. The 4×4 pixel array illustrated in FIG. 19 is for illustration purposes only. In embodiments of the present invention, the size of the array may be as large as practically achievable or needed depending on the specifics of the application, e.g. the total size of the image sensor imaging area and/or the pixel size. The two dimensions of the image sensor need not be equal. Individual pixels 2001 are typically square, but may be of other shapes, e.g. rectangular or hexagonal. Each pixel may have its own output 2002, and multiple signals or electrical connections such as gates, control signals, power supplies and ground. For practical reasons, most or all of these signals (except the pixel output signals) may be connected together between neighboring pixels and may be driven from the edges of the image sensor, where an electrical connection is more easily made than if the signals were to be connected to each pixel individually. FIG. 19 shows only two such signals 2003 and 2004 as an illustration, but in a practical device there may be more than two signals shared between pixels.

In one embodiment of the present invention, each pixel 2001 features a floating diffusion capacitance as its output sensing node; the pixel driving signals, that may be shared between neighboring pixels, comprise at least a signal to reset the floating diffusion, and a signal to transfer the charge collected in the pixel to said floating diffusion. The charge accumulation methodology introduced in FIG. 11 may be applied to image sensor 2000, with a timing diagram very similar to the one illustrated in FIG. 11: a reset clock is applied to each pixel only at time intervals that encompass multiple samplings of the pixel output signal, while the charge collected by said pixel is transferred to the pixel output sensing node before each sample. Using this methodology, charge signals for an arbitrary number of transfer cycles can be accumulated at the pixel output, resulting in an output signal waveform which is immune from the interference introduced by the reset clock, and thus enabling low noise read out at high sample speed.

Similarly, other embodiments of the present invention using image sensor 2000 may implement methodologies such as those described in FIGS. 12, 14, 15, 16 and 18, where repeated samples of the output signal of individual pixels may be performed between resets.

The various embodiments of the structures and methods of this invention that are described above are illustrative only of the principles of this invention and are not intended to limit the scope of the invention to the particular embodiments described. For example, an arbitrary number of pixels or pixel samples may be read out after each reset operation in manners similar to the ones depicted in FIGS. 11, 12, 13, 14, 15, 16, and 18, or an arbitrary number of pixels read out by the same output sensing node, or lines of pixels, may be read out between resets in a manner similar to the one depicted in FIG. 13. Thus, the invention is limited only by the following claims and their equivalents.

The invention claimed is:

1. A method of inspecting a sample using an image sensor and an analog-to-digital converter (ADC), the image sensor including multiple pixels disposed in at least one column and an output sensing node, the ADC being configured to convert analog output signals on said output sensing node into corresponding digital image data values, the method comprising:

driving the image sensor such that a plurality of analog image data values are generated in the multiple pixels, each said analog image data value corresponding to a radiation portion directed onto said multiple pixels from a corresponding region of the sample, said driving including systematically transferring said analog image data values along said at least one column from said multiple pixels to said output sensing node while translating said sample relative to said image sensor such that each said analog image data value is shifted from a first said pixel to a second said pixel in said at least one column in coordination with said corresponding region of the sample, whereby said each analog image data value is influenced by said corresponding radiation portion from said corresponding region during a first time period when said each analog image data value is in said first pixel, and said each analog image data value is influenced by said corresponding radiation portion during a second time period when said each analog image data value is in said second pixel, and wherein said systematically transferring is performed such that said output sensing node stores charge values determined by said systematically transferred analog image data values and generates said analog output signals in accordance with said stored charge values, wherein driving the image sensor further includes periodically resetting the output sensing node to an initial charge value according to a reset clock signal; and controlling the ADC to sequentially convert one or more of said analog output signals generated on said output sensing node into two or more said corresponding digital data values during each cycle of said reset clock signal.

2. The method of claim 1, wherein driving the image sensor further comprises transferring two or more analog image data values to said output sensing node during each cycle of said reset clock signal such that a charge value stored on said output sensing node includes a sum of said two or more of said analog image data values.

3. The method of claim 2,
wherein driving the image sensor further comprises sequentially transferring said two or more analog image data values to said output sensing node such that said output sensing node stores a first said analog image data value during a first time period, and said output sensing node stores a sum of said first analog image data value and a second said analog data image value during a second time period, and
wherein controlling the ADC further comprises generating a first corresponding digital output data value during said first time period, and generating a second corresponding digital output value during said second time period.

4. The method of claim 3, further comprising determining at least one digital image data value by determining a difference between said first and second digital output values.

5. The method of claim 2,
wherein driving the image sensor further comprises driving a shift register using a shift register clock signal such that one of said analog image data values is serially transferred from said shift register to said output sensing node during each cycle of said shift register clock signal, and
wherein periodically resetting the output sensing node to said initial value comprises resetting said output sensing node every two or more cycles of said shift register clock signal.

6. The method of claim 2,
wherein driving the image sensor further comprises simultaneously transferring said two or more analog image data values to said output sensing node such that said output sensing node stores a sum of said two or more analog image data values during a first time period, and
wherein controlling the ADC further comprises generating a first corresponding digital output data value during a first portion of said first time period, and generating a second corresponding digital output value during a second portion of said first time period.

7. The method of claim 6, determining at least one digital image data value by determining an average of said first and second digital output values.

8. A method of inspecting a sample, the method comprising:
directing and focusing radiation onto the sample;
receiving radiation from the sample and directing received radiation to an image sensor, the image sensor comprising at least a first pixel, a second pixel and an output sensing node;
driving the image sensor such that analog image data values captured by the first and second pixels are sequentially transferred to the output sensing node in accordance with at least one first clock signal, said analog image data values being captured while translating said sample relative to said image sensor such that each said analog image data value is shifted from the first pixel to the second said pixel in coordination with a corresponding region of the sample, whereby said each analog image data value is influenced by said corresponding radiation portion from said corresponding region during a first time period when said each analog image data value is in said first pixel, and said each analog image data value is influenced by said corresponding radiation portion during a second time period when said each analog image data value is in said second pixel, and wherein said driving is performed such that the output sensing node is periodically reset in accordance with a reset clock signal, whereby a charge stored on the output sensing node incrementally increases with each sequentially transferred analog image data value; and
generating digital image data values associated with the sample by controlling a converter to digitize an output signal generated by an associated said incrementally increasing charge stored on the output sensing node in accordance with a second clock signal such that at least two digital image data values are generated between each periodic reset of the output sensing node.

9. The method of claim 8, wherein driving the image sensor further comprises transferring two or more analog image data values to said output sensing node during each cycle of said reset clock signal such that said two or more of said analog image data values are stored simultaneously on said output sensing node.

10. The method of claim 9,
wherein driving the image sensor further comprises sequentially transferring first and second analog image data values to said output sensing node such that said output sensing node stores a first charge value generated by said first analog image data value during a first time period, and said output sensing node stores a second charge value equal to a sum of said first analog image data value and said second analog data image value during a second time period, and
wherein generating said digital image data values comprises generating a first digital output value during said first time period by digitizing a first output signal generated in accordance with said first charge value, and generating a second digital output value during said second time period by digitizing a second output signal generated in accordance with said second charge value.

11. The method of claim 10, further comprising determining at least one digital image data value by determining a difference between said first and second digital output values.

12. The method of claim 9,
wherein driving the image sensor further comprises simultaneously transferring said two or more analog image data values to said output sensing node such that said output sensing node stores a corresponding charge value generated by a sum of said two or more analog image data values during a first time period, and
wherein generating said digital image data values comprises generating a first corresponding digital output value by digitizing said corresponding charge value during a first portion of said first time period, and generating a second corresponding digital output value by digitizing said corresponding charge value during a second portion of said first time period.

13. The method of claim 12, determining at least one digital image data value by determining an average of said first and second digital output values.

14. The method of claim 8,
wherein directing and focusing said radiation comprises generating at least one of electromagnetic radiation and charged particles, and
wherein receiving said radiation comprises directing at least one of scattered radiation and reflected radiation received from the sample to the image sensor.

15. The method of claim 8,
wherein the image sensor comprises a plurality of pixels disposed in a line, and
wherein driving the image sensor comprises transferring a plurality of analog image data values respectively captured by the plurality of pixels to the output sensing node such that a total output signal generated by a sum of said plurality of analog image data values is stored on said output sensing node when said converter is controlled to digitize said output signal, whereby an associated digital image data value is generated corresponding to said total output signal.

16. The method of claim 15, further comprising:
comparing said associated digital image data value with a predetermined threshold value; and
transmitting said associated digital image data value to one of a processor and a data storage device only when said associated digital image data value exceeds said threshold value.

17. A system for inspecting a sample, the system comprising:
an illumination source;
an imaging device comprising an image sensor including a plurality of pixels disposed in at least one column and at least one output sensing node;
optics configured to direct light from the illumination source to the sample, and to direct light from the sample to the imaging apparatus;
at least one Analog-to-Digital Converter (ADC) configured to generate digital image data values by digitizing corresponding output signals generated on said at least one output sensing node;
at least one Digital Signal Processor (DSP) configured to receive and evaluate said digital image data values;
a stage configured to facilitate translation of the sample relative to the optics; and
a digital control device configured to generate clock, reset and control signals utilized to drive the image sensor, the ADC and the DSP in coordination with translation of said sample by said stage such that:

a plurality of analog image data values are generated in the multiple pixels, each said analog image data value corresponding to a radiation portion directed from a corresponding region of the sample, wherein each said analog image data value is shifted from a first said pixel to a second said pixel in said at least one column in coordination with translation of said corresponding region of the sample, whereby said each analog image data value is influenced by said corresponding radiation portion from said corresponding region during a first time period when said each analog image data value is in said first pixel, and said each analog image data value is influenced by said corresponding radiation portion during a second time period when said each analog image data value is in said second pixel;

said analog image data values are systematically transferred from said multiple pixels to said output sensing node in accordance with at least one first clock signal;

said output sensing node stores charge values determined by said systematically transferred analog image data values and generates said analog output signals in accordance with said stored charge values;

said output sensing node is periodically reset to an initial value according to a reset clock signal; and the ADC generates at least two digital image data values between each periodic reset of the output sensing node.

18. The system of claim 17, wherein the digital control device is configured such that a number of said digital image data values generated between each periodic reset of the output sensing node is determined by stored mode control data.

19. The system of claim 18,
wherein said at least one Digital Signal Processor (DSP) is configured to compare each of said digital image data values against predetermined condition value, and to generate one or more feedback signals in accordance with at least one said comparison, and
wherein said digital control device is configured such that said stored mode control data is determined by said one or more feedback signals, whereby said number of said digital image data values generated between each periodic reset of the output sensing node is adjustable by way of said comparison between said digital image data values and said predetermined condition value.

20. A system for inspecting a sample, the system comprising:
an illumination source;
an imaging device comprising an image sensor including a plurality of pixels and at least one output sensing node;
optics configured to direct light from the illumination source to the sample, and to direct light from the sample to the imaging apparatus;
at least one Analog-to-Digital Converter (ADC) configured to generate digital image data values by digitizing corresponding output signals generated on said at least one output sensing node;
at least one Digital Signal Processor (DSP) configured to receive and evaluate said digital image data values;
a digital control device configured to generate clock, reset and control signals utilized to drive the image sensor, the ADC and the DSP such that:

a plurality of analog image data values are generated in the multiple pixels, each said analog image data value corresponding to a radiation portion directed onto said multiple pixels from a corresponding region of the sample;

said analog image data values are systematically transferred from said multiple pixels to said output sensing node in accordance with at least one first clock signal;

said output sensing node generates said analog output signals in accordance with one or more of said plurality of analog image data values;

said output sensing node is periodically reset to an initial value according to a reset clock signal; and the ADC generates at least two digital image data values between each periodic reset of the output sensing node, wherein the DSP is configured to measure an amplitude of background signals by evaluating the output signals accumulated at said at least one output node for a plurality of pixels read out in between reset operations; and wherein the digital control logic is configured to vary the reset clock signal, based on feedback signals received from the DSP, to change the number of said digital image data values generated between each periodic reset of the output sensing node.

21. A system for inspecting a sample, the system comprising:
an illumination source;
an imaging device comprising an image sensor including a plurality of pixels and at least one output sensing node;
optics configured to direct light from the illumination source to the sample, and to direct light from the sample to the imaging apparatus;
at least one Analog-to-Digital Converter (ADC) configured to generate digital image data values by digitizing corresponding output signals generated on said at least one output sensing node;
at least one Digital Signal Processor (DSP) configured to receive and evaluate said digital image data values;
a digital control device configured to generate clock, reset and control signals utilized to drive the image sensor, the ADC and the DSP such that:

a plurality of analog image data values are generated in the multiple pixels, each said analog image data value corresponding to a radiation portion directed onto said multiple pixels from a corresponding region of the sample;

said analog image data values are systematically transferred from said multiple pixels to said output sensing node in accordance with at least one first clock signal;

said output sensing node generates said analog output signals in accordance with one or more of said plurality of analog image data values;

said output sensing node is periodically reset to an initial value according to a reset clock signal; and the ADC generates at least two digital image data values between each periodic reset of the output sensing node, wherein the DSP is configured to count the occurrences of signals of interest above said background signals within a plurality of pixels read out in between reset operations; and wherein the digital control logic is configured to vary the reset clock signal, based on said count received from the DSP, to change the number of said digital image data values generated between each periodic reset of the output sensing node.

\* \* \* \* \*